US008852320B2

(12) United States Patent
Yaghi et al.

(10) Patent No.: US 8,852,320 B2
(45) Date of Patent: Oct. 7, 2014

(54) PREPARATION OF METAL-TRIAZOLATE FRAMEWORKS

(75) Inventors: Omar M. Yaghi, Los Angeles, CA (US); Fernando J. Uribe-Romo, Ithaca, NY (US); Felipe Gandara-Barragan, Los Angeles, CA (US); David K. Britt, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 202 days.

(21) Appl. No.: 13/354,574

(22) Filed: Jan. 20, 2012

(65) Prior Publication Data

US 2012/0186449 A1    Jul. 26, 2012

Related U.S. Application Data

(60) Provisional application No. 61/434,936, filed on Jan. 21, 2011.

(51) Int. Cl.
*B01D 53/04* (2006.01)
*C07D 249/04* (2006.01)
*C07F 1/00* (2006.01)
*C07F 3/00* (2006.01)
*C07F 13/00* (2006.01)
*C07F 15/02* (2006.01)
*C07F 15/04* (2006.01)
*B01J 20/22* (2006.01)

(52) U.S. Cl.
CPC ............ *C07F 1/005* (2013.01); *B01D 2253/204* (2013.01); *C07D 249/04* (2013.01); *C07F 3/003* (2013.01); *C07F 13/005* (2013.01); *C07F 15/025* (2013.01); *C07F 15/045* (2013.01); *B01J 20/226* (2013.01); *Y02C 20/10* (2013.01)
USPC .............................. 95/90; 548/101; 548/255

(58) Field of Classification Search
CPC ..... B01J 20/226; C07D 249/04; Y02C 20/10; B01D 2253/204; C07F 13/005; C07F 1/005; C07F 15/025; C07F 15/045; C07F 30/03
USPC ......... 95/90, 900; 96/108; 502/400; 548/101, 548/255
See application file for complete search history.

(56) References Cited

U.S. PATENT DOCUMENTS 2,684,967 A    7/1954    Clyde Berg
4,532,225 A    7/1985    Tsao et al.
(Continued)

FOREIGN PATENT DOCUMENTS

DE    102005023856 A1    11/2006
DE    102005054523 A1    5/2007
(Continued)

OTHER PUBLICATIONS

Zhang, Jie Peng et al, "Crystal engineering of binary metal imidazolate and triazolate frameworks", Chem. Commun., 2006, 1689-1699.*
(Continued)

*Primary Examiner* — Frank Lawrence
(74) *Attorney, Agent, or Firm* — Gavrilovich, Dodd & Lindsey LLP; Joseph R. Baker, Jr.

(57) ABSTRACT

The disclosure provides for novel metal-triazolate frameworks, methods of use thereof, and devices comprising the frameworks thereof.

26 Claims, 23 Drawing Sheets

(56) References Cited

U.S. PATENT DOCUMENTS

| | | |
|---|---|---|
| 5,064,804 A | 11/1991 | Soo et al. |
| 5,160,500 A | 11/1992 | Chu et al. |
| 5,208,335 A | 5/1993 | Ramprasad et al. |
| 5,648,508 A | 7/1997 | Yaghi |
| 5,733,505 A | 3/1998 | Goldstein et al. |
| 6,479,447 B2 | 11/2002 | Bijl et al. |
| 6,501,000 B1 | 12/2002 | Stibrany et al. |
| 6,617,467 B1 | 9/2003 | Mueller et al. |
| 6,624,318 B1 | 9/2003 | Mueller et al. |
| 6,893,564 B2 | 5/2005 | Mueller et al. |
| 6,929,679 B2 | 8/2005 | Mueller et al. |
| 6,930,193 B2 | 8/2005 | Yaghi et al. |
| 7,196,210 B2 | 3/2007 | Yaghi et al. |
| 7,202,385 B2 | 4/2007 | Mueller et al. |
| 7,279,517 B2 | 10/2007 | Mueller et al. |
| 7,309,380 B2 | 12/2007 | Mueller et al. |
| 7,343,747 B2 | 3/2008 | Mueller et al. |
| 7,411,081 B2 | 8/2008 | Mueller et al. |
| 7,524,444 B2 | 4/2009 | Hesse et al. |
| 7,582,798 B2 | 9/2009 | Yaghi et al. |
| 7,637,983 B1 | 12/2009 | Liu et al. |
| 7,652,132 B2 | 1/2010 | Yaghi et al. |
| 7,662,746 B2 | 2/2010 | Yaghi et al. |
| 7,799,120 B2 | 9/2010 | Yaghi et al. |
| 7,815,716 B2 | 10/2010 | Mueller et al. |
| 8,343,260 B2 * | 1/2013 | Omary et al. ............. 95/116 |
| 2003/0004364 A1 | 1/2003 | Yaghi et al. |
| 2003/0078311 A1 | 4/2003 | Mueller et al. |
| 2003/0148165 A1 | 8/2003 | Mueller et al. |
| 2003/0222023 A1 | 12/2003 | Mueller et al. |
| 2004/0081611 A1 | 4/2004 | Mueller et al. |
| 2004/0225134 A1 | 11/2004 | Yaghi et al. |
| 2004/0249189 A1 | 12/2004 | Mueller et al. |
| 2004/0265670 A1 | 12/2004 | Mueller et al. |
| 2005/0004404 A1 | 1/2005 | Mueller et al. |
| 2005/0014371 A1 | 1/2005 | Tsapatsis |
| 2005/0124819 A1 | 6/2005 | Yaghi et al. |
| 2005/0154222 A1 | 7/2005 | Mueller et al. |
| 2005/0192175 A1 | 9/2005 | Yaghi et al. |
| 2006/0057057 A1 | 3/2006 | Mueller et al. |
| 2006/0135824 A1 | 6/2006 | Mueller et al. |
| 2006/0154807 A1 | 7/2006 | Yaghi et al. |
| 2006/0185388 A1 | 8/2006 | Mueller et al. |
| 2006/0252641 A1 | 11/2006 | Yaghi et al. |
| 2006/0252972 A1 | 11/2006 | Pilliod et al. |
| 2006/0287190 A1 | 12/2006 | Eddaoudi et al. |
| 2007/0068389 A1 | 3/2007 | Yaghi et al. |
| 2007/0202038 A1 | 8/2007 | Yaghi et al. |
| 2007/0248575 A1 | 10/2007 | Connor et al. |
| 2008/0017036 A1 | 1/2008 | Schultink et al. |
| 2008/0184883 A1 | 8/2008 | Zhou et al. |
| 2009/0155588 A1 | 6/2009 | Hesse et al. |
| 2009/0183996 A1 * | 7/2009 | Richter et al. ............. 205/424 |
| 2010/0132549 A1 | 6/2010 | Yaghi et al. |
| 2010/0143693 A1 | 6/2010 | Yaghi et al. |
| 2010/0186588 A1 | 7/2010 | Yaghi et al. |
| 2010/0286022 A1 | 11/2010 | Yaghi et al. |
| 2011/0137025 A1 | 6/2011 | Yaghi et al. |
| 2011/0282071 A1 * | 11/2011 | Shi ............................. 548/255 |

FOREIGN PATENT DOCUMENTS

| | | |
|---|---|---|
| EP | 1674555 A1 | 6/2006 |
| WO | 2004101575 A2 | 11/2004 |
| WO | 2006047423 A2 | 5/2006 |
| WO | 2006072573 A2 | 7/2006 |
| WO | 2006116340 A1 | 11/2006 |
| WO | 2007101241 A2 | 9/2007 |
| WO | 2007111739 A2 | 10/2007 |
| WO | 2008091976 A1 | 7/2008 |
| WO | 2008138989 A1 | 11/2008 |
| WO | 2008140788 A1 | 11/2008 |
| WO | 2009020745 A9 | 2/2009 |
| WO | 2009042802 A1 | 4/2009 |
| WO | 2009056184 A1 | 5/2009 |
| WO | 2009149381 A3 | 12/2009 |
| WO | 2010056092 A9 | 5/2010 |
| WO | 2010078337 A1 | 7/2010 |
| WO | 2010080618 A1 | 7/2010 |
| WO | 2010083418 A1 | 7/2010 |
| WO | 2010088629 A1 | 8/2010 |
| WO | 2010090683 A1 | 8/2010 |
| WO | 2010148276 A3 | 12/2010 |
| WO | 2010148296 A3 | 12/2010 |
| WO | 2010148374 A3 | 12/2010 |
| WO | 2011014503 A1 | 2/2011 |
| WO | 2011038208 A2 | 3/2011 |
| WO | 2011146155 A9 | 11/2011 |
| WO | 2012012495 A3 | 1/2012 |
| WO | 2012082213 A2 | 6/2012 |
| WO | 2012100224 A3 | 7/2012 |
| WO | 2012106451 A2 | 8/2012 |

OTHER PUBLICATIONS

Zhu, Ali-Xin et al, "Izomeric Zinc (II) Triazolate Frameworks with 3-Connected Networks: Syntheses, Structures, and Sorption Properties", Inorg. Chem., 2009, 48, 3882-3889.*
Zhou, Xin-Hui et al, "Hydrothermal syntheses and structures of three novel coordination polymers assembled from 1,2,3-triazolate ligands", CrystEngComm, 2009, 11, 1964-1970.*
Demessence, Aude et al, "Strong CO2 Binding in a Water-Stable, Triazolate-Bridged Metal-Organic Framework Functionalized with Ethylenediamine", J. Am. Chem. Soc. 2009, 131, 8784-8786.*
Young, Jung Doo, International Search Report and Written Opinion, Korean Intellectual Property Office, PCT/US2012/022114, Aug. 22, 2012.
Bai, Lingfei, International Preliminary Report on Patentability and Written Opinion, The International Bureau of WIPO, PCT/US2012/022114 Jul. 23, 2013.
Zhou, X., et al., "Hydrothermal Syntheses and Structures of Three Novel Coordination Polymers Assembled from 1, 2, 3-Triazolate Ligands" CrystEngComm, 2009, vol. 11, pp. 1964-1970.
Yang, E. et al., Four Novel Three-Dimensional Triazole-Based Zinc(II) Metal-Organic Frameworks Controlled by the Spacers of Dicarboxylate Ligands, Cryst. Growth & Design, 2007, vol. 7, pp. 2009-2015.
Park H. et al., "Synthesis, Structure Determination, and Hydrogen Sorption Studies of New Metal-Organic Frameworks Using Triazole and Naphthalenedicarobylic Acid", Chem. Mater., 2007. vol. 19, pp. 1302-1308.
Li, Y. et al., "Hydrogen Storage in Metal-Organic and Covalent-Organic Frameworks by Spillover", AIChE J., 2008, pp. 269-279.
Demessence, A. et al., "Strong CO2 Binding in a Water-Stable, Triazolate-Bridged Metal-Organic Framework Functionalized with Ethylenediamine", J. Am. Chem. Soc., 2009, vol. 131, pp. 8784-8786.
Goto, Y. et al., "Clickable Metal-Organic Framework," J. Am. Chem. Soc., 2008, vol. 130, pp. 1354-1355.
Gadzikwa, T. et al., "Selective Bifunctional Modification of a Non-catenated Metal-Organic Framework Material via Click Chemistry," J. Am. Chem. Soc., 209, vol. 131, pp. 13613-13615.
Zhang, J. et al., "Exceptional Framework Flexibility and Sorption Behavior of a Multifunctional Porous Cuprous Triazolate Framework," J. Am. Chem. Soc., 2008, vol. 130, pp. 6010-6017.
Zhu, A. et al., "Isomeric Zinc(II) Triazolate Frameworks with 3-Connected Networks: Syntheses, Structures, and Sorption Properties," Inorg. Chem., 2009, Vol. 48, pp. 3882-3889.
Llabres et al., "MOFs as catalysts: Activity, reusability and shape-selectivity of a Pd-containing MOF," Journal of Catalysis 250(2):294-298.
Loeb, SJ, "Rotaxanes as ligands: from molecules to materials" Chemical Society reviews, 2007, 36, pp. 226-235.
Long et al., "The Pervasive Chemistry of Metal-Organic Frameworks," Chem. Soc. Rev. 38:1213-1214 (2009).
Lu et al., "Synthesis and Structure of Chemically Stable Metal-Organic Polyhedra," J. Am. Chem. Soc. 131:(35) 12532-12533 (2009).

(56) References Cited

OTHER PUBLICATIONS

Mendoza-Cortes et al., "Adsorption Mechanism and Uptake of Methane in Covalent Organic Frameworks: Theory and Experiment," J. Phys. Chem. 114:10824-10833 (2010).
Michalitsch, Richard. International Search Report and Written Opinion for PCT/US2009/069700. Date of Mailing: May 7, 2010.
Millward et al., "Metal-Organic Frameworks with Exceptionally High Capacity for Storage of Carbon Dioxide at Room Temperature," J. Am. Chem. Soc. 127:17998-17999 (2005).
Morris et al., "Crystals as Molecules: Postsynthesis Covalent Functionalization of Zeolitic Imidazolate Frameworks," J. Am. Chem. Soc. 130:12626-12627 (2008).
Morris et al., "A Combined Experimental—Computational Investigation of Carbon Dioxide Capture in a Series of Isoreticular Zeolitic Imidazolate Frameworks," J. Am. Chem. Soc. 132:11006-11008 (2010).
Morris et al., "Postsynthetic Modification of a Metal-Organic Framework for Stabilization of a Hemiaminal and Ammonia Uptake," Inorg. Chem. 50:6853-6855 (2011).
Moyse, Ellen, International Preliminary Report on Patentability and Written Opinion, Date of Issuance of Report: Nov. 17, 2009, International Application No. PCT/US081006008.
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing Jul. 28, 2011.
Ni et al,. "Porous Metal-Organic Truncated Octahedron Constructed from Paddle-Wheel Squares and Terthiophene Links," J. Am. Chem. Soc. 127:12752-12753 (2005).
Nickitas-Etienne, Athina, International Preliminary Report on Patentability and Written Opinion, Date of Issuance of Report: Jan. 19, 2010, International Application No. PCT/US08/70149.
Nickitas-Etienne, Athina. International Preliminary Report on Patentability for PCT/US2008/07741. Date of issuance of this report: Mar. 30, 2010.
Nickitas-Etienne, Athina. International Preliminary Report on Patentability for PCT/US2009/068849. Date of Mailing: Jun. 30, 2011.
Niu et al., "Synthesis and structural characterization of the one dimensional polymers [Rh2(OAc)4(NCPhCN)S, S = CH3COCH3, CH3OH, C2H5OH, C4H8O, and C6H6," Polyhedron 17(23-24):4079-89 (1998).
Novoa, Carlos, International Search Report and Written Opinion for PCT/US2010/021201, European Patent Office. Date of Mailing: Apr. 27, 2010.
Oisaki et al., "A Metal-Organic Framework with Covalently Bound Organometallic Complexes," J. Am. Chem. Soc. 132:9262-9264 (2010).
Wu et al., "Structural Study of New Hydrocarbon Nano-Crystals by Energy-Filtered Electron Diffraction," Ultramicroscopy 98:145-150 (2004).
O'Keefe et al., "Germanate Zeolites: Contrasting the Behavior of Germanate and Silicate Structures Built from Cubic T8O20 units (T = Si or Ge)," Chem. Eur. J. 5:2796-2801 (1999).
O'Keefe et al., "Frameworks for Extended Solids: Geometrical Design Principles," J. Solid State Chem. 152:3-20 (2000).
Okeeffe et al., "Reticular Chemistry—Present and Future Prospects—Introduction,"J. Solid State Chem.178:V-VI (2005).
O'Keeffe et al., "The Reticular Chemistry Structure Resource (RCSR) Database of, and Symbols for, Crystal Nets," Acc. Chem. Res. 41:1782-1789 (2008).
Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.
Park, Jae Woo. International Search Report for PCT/US2010/039123. Date of Mailing: Feb. 24, 2011.
Patteux, Claudine. International Search Report for PCT/US2010/043373. Date of Mailing: Oct. 10, 2010.
Pawsey et al., "Hyperpolarized 129Xe Nuclear Magnetic Resonance Studies of Isoreticular Metal-Organic Frameworks," Phys. Chem. 111:6060-6067 (2007).

Phan et al., "Synthesis, Structure, and Carbon Dioxide Capture Properties of Zeolitic Imidazolate Frameworks," Acc. Chem. Res 43:58-67 (2009).
Phan et al., "Metal-Organic Frameworks of Vanadium as Catalysts for Conversion of Methane to Acetic Acid," Inorg. Chem. 50:7388-7390 (2011).
Plevert et al., "A Flexible Germanate Structure Containing 24-Ring Channels With Very Low Framework Density," J. Am. Chem. Soc. 123:12706-12707 (2001).
Plevert et al., "Synthesis and Characterization of Zirconogermanates," Inorg. Chem., 42:5954-5959 (2003).
Plevert et al., "Layered Structures Constructed from New Linkages of Ge7(O,OH,F)19 Clusters," Chem. Mater. 15:714-718 (2003).
Reineke et al., "From Condensed Lanthanide Coordination Solids to Microporous Frameworks Having Accessible Metal Sites," J. Am. Chem. Soc 121:1651-1657 (1999).
Reineke et al., "A Microporosity of Lanthanide-Organic Frameworks," Angew. Chem. Int. Ed. 38:2590-2594 (1999).
Reineke et al., "Large Free Volume in Interpenetrating Networks: The Role of Secondary Building Units Exemplified by Tb2(ADB)3[(CH3)2SO]4-16[(CH3)2SO]," J. Am. Chem. Soc. 122:4843-4844 (2000); Featured in Science Magazine, Editors Choice (Nov. 2000).
Rosi et al., "Infinite Secondary Building Units and Forbidden Catenation in Metal-Organic Frameworks," Angew. Chem. Int. Ed. 41:294-297 (2002).
Rosi et al., "Advances in the Chemistry of Metal-Organic Frameworks," CrystEngComm 4:401-404 (2002).
Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.
Rosi et al., "Rod-Packings and Metal-Organic Frameworks Constructed from Rod-Shaped Secondary Building Units," J. Am. Chem. Soc. 127:1504-1518 (2005).
Rowsell et al., "Hydrogen Sorption in Functionalized Metal-Organic Frameworks," J. Am. Chem. Soc.126: 5666-5667 (2004).
Rowsell et al., "Metal-Organic Frameworks: A New Class of Porous Materials," Microporous Mesoporous Mater. 73:3-14 (2004).
Rowsell et al., "Strategies for Hydrogen Storage in Metal-Organic Frameworks," Angew. Chem. Int. Ed. 44:4670-4679 (2005).
Rowsell et al., "Gas Adsorption Sites in a Large-Pore Metal-Organic Framework," Science 309:1350-1354 (2005).
Rowsell et al., "Characterization of H2 Binding sites in prototypical metal-organic frameworks by inelastic neutron scattering," J. Am. Chem. Soc. 127:14904-14910 (2005).
Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).
Siberio-Perez, "Raman Spectroscopic Investigation of CH4 and N2 Adsorption in Metal-Organic Frameworks," Chem. Mater. 19:3681-3685 (2007).
Smaldone et al., "Metal-Organic Frameworks from Edible Nature Products," Angew. Chem. Int. Ed. 49:8630-8634 (2010).
Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.
Costa et al., "Chemical Modification of a Bridging Ligand Inside a Metal-Organic Framework while Maintaining the 3D Structure," Eur. J. Inorg. Chem. 10:1539-1545 (2008).
Cui et al., "IIn Situ Hydrothermal Growth of Metal-Organic Framework 199 Films on Stainless Steel Fibers for Solid-Phase Microextraction of Gaseous Benzene Homologues," Anal. Chem. 81(23):9771-9777 (2009).
Dugan et al., "Covalent modification of a metal-organic framework with isocyanates: probing substrate scope and reactivity," 29:3366-3368 (2008).
Luo et al., "Two new metal-triazole-benzenedicarboxylate frameworks affording an uncommon 3,4-connected net and unique 4,6-connected rod packing: hydrothermal synthesis, structure, thermostability and luminescence studies," CrystEngComm 11(6):1097-1102 (2009).

(56) References Cited

OTHER PUBLICATIONS

Galli et al., "Adsorption of Harmful Organic Vapors by Flexible Hydrophobic Bis-pyrazolate Based MOFs," Chem. Mater. 22(5):1664-1672 (2010).

Ingleson et al., "Framework fractionalization triggers metal complex binding," Chem. Comm. 23:2680-2682 (2008).

Li et al., "Synthesis and Structural Characterization of a New 3D Lead Coordination Polymer with a Tetrazole-1-acetate Ligand, " Chinese J. Struct. Chem. 30(7):1049-1053 (2011).

Ling et al., "A zinc(II) metal-organic framework based on triazole and dicarboxylate ligands for selective adsorption of hexane isomers," Chem. Comm. 47:7197-7199 (2011).

Natarajan et al., "Non-carboxylate based metal-organic frameworks (MOFs) and related aspects," Current Opinion in Solid State and Materials Science 13(3-4):46-53 (2009).

Nickitas-Etienne, Athina, International Preliminary Report on Patentability for PCT/US2009/068731. Date of Issuance of the Report: Jun. 21, 2011.

Peterson et al., "Ammonia Vapor Removal by Cu3(BTC)2 and Its Characterization by MAS NMR," J. Phys. Chem. C. 113(32):13906-13917 (2009).

Seo et al., "A homochiral metal-organic porous material for enantioselective separation and catalysis," Nature 404:982-986 (2000).

Sigma-Aldrich, Basolite C300 (MOF-199), catalog No. 688614; http://www.sigmaaldrich.com/catalog/ProductDetail.do?D7=0 &N5=SEARCH_CONCAT_PNO%7CBRAND_KEY &N4=688614%7CALDRICH&N25=0&Qs=ON&F=SPEC.

Song et al., "Hydrothermal Synthesis and Structural Characterization of Three-dimensional Metal-organic Framework [Zn3(C2H2N3)2(C7H5O2)4]," Chem. Res. Chinese Universities 25(1):1-4 (2009).

Tanabe et al., "Systematic Functionalization of a Metal-Organic Framework via a Postsynthetic Modification Approach," J. Am. Chem. Soc. 130(26):8508-8517 (2008).

Vitillo et al., "Role of Exposed Metal Sites in Hydrogen Storage in MOFs," J. Am. Chem. Soc. 130(26):8386-8396 (2008).

Wang et al., "Postsynthetic Covalent Modification of a Neutral Metal-Organic Framework," J. Am. Chem. Soc. 129 (41):12368-12369 (2007).

Wang et al., "Tandem Modification of Metal-Organic Frameworks by a Postsynthetic Approach," Angew. Chem. Int. 47:4699-4702 (2008).

Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.

Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.

Yang et al. "Two Novel Triazole-Based Metal-Organic Frameworks Consolidated by a Flexible Dicarboxylate Co-ligand: Hydrothermal Synthesis, Crystal Structure, and Luminescence Properties," Australian Journal of Chemistry 61 (10):813-820 (2008).

Zhang et al., "Syntheses, Structures, and Porous/Luminescent Properties of Silver 3-Alkyl-1,2,4-Triazolate Frameworks with Rare 3-Connected Topologies," Crystal Growth and Design 11:796-802 (2011).

Adkins, Chinessa T. Nonfinal Office Action for U.S. Appl. 12/524,205. Mail Date Apr. 17, 2012.

Adkins, Chinessa T. Final Office Action for U.S. Appl. 12/524,205. Mail Date Sep. 27, 2012.

Barman et al., "Incorporation of active metal sites in MOFs via in situ generated ligand deficient metal-linker complexes" Chem. Commun. 47:11882-11884 (Oct. 11, 2011).

Bork, Ana-Marie., International Search Report for PCT/US2011/24671, European Patent Office, Nov. 30, 2011.

Chen et al., "Noncovalently Netted, Photoconductive Sheets with Extremely High Carrier Mobility and Conduction Anisotropy from Triphenylene-Fused Meetal Trigon Conjugates," In. J. Am. Chem. Soc. 131:7287-7297 (2009).

Choi et al., "Reversible Interpenetration in a Metal-Organic Framework Triggered by Ligand Removal and Addition," Angew. Chem. Int. Ed. 51:8791—8795 (2012).

Coskun et al., "Metal—Organic Frameworks Incorporating Copper-Complexed Rotaxanes," Angew. Chem. Int. Ed., 51:2160-2163 (2012).

Chun et al., "Concomitant Formation of N-Heterocyclic Carbene-Copper Comlexies within a Supramolecular Network in the Self-Assembly of Immidzolium Dicarboxylate with Metal Ions," Inorganic Chemistry, Jul. 20, 2009, pp. 6353-6355, vol. 48, No. 14.

Chun et al., "Cu2O: A versatile Reagent for Base-Free Direct Synthesis of NHC-Copper Complexes and Decoration of 3D-MOF with Coordinatively Unsaturated NHC-Copper Species," Organometallics, Mar. 16, 2010, pp. 1518-1521, vol. 29, No. 7.

Cordero Garcia, Marcela M. Nonfinal Office Action for U.S. Appl. No. 12/680,141. Mail Date Nov. 2, 2012.

Crees et al., "Synthesis of a Zinc(II) Imidazolium Dicarboxylate Logand Metal-Organic Framework (MOF): a Potential Precursor to MOF-Tethered N-Heterocyclic Carbene Compounds," Inorganic Chemistry, pp. 1712-1719, vol. 49, No. 4.

Deng et al., "Large-Pore Apertures in a Series of Metal-Organic Frameworks," Science 336:1018-1023 (May 25, 2012).

Fei et al., "A Nearly Planar Water Sheet Sandwiched between Strontium-Imidazolium Carboxylate Coordination Polymers," Inorg. Chem., 2005, pp. 5200-5202, vol. 44.

Fracaroli et al., "Isomers of Metal-Organic Complex Arrays," Inorg. Chem. 51: 6437-6439 (Jun. 5, 2012).

Furukawa et al., "Isoreticular Expansion of MetalOrganic Frameworks with Triangular and Square Building Units and the Lowest Calculated Density for Porous Crystals," Inorg. Chem. 50:9147-9152 (2011).

Gandara et al., "Porous, Conductive Metal-Triazolates and Their Structural Elucidation by the Charge-Flipping Method," Chem. Eur. J. 18:10595-10601 (2012).

Gassensmith et al., "Strong and Reversible Binding of Carbon Dioxide in a Green Metal-Organic Framework," J. Am. Chem. Soc. 133:15312-15315 (Aug. 30, 2011).

Hmadeh et al., "New Porous Crystals of Extended Metal-Catecholates," J. Chem. Mater. 24:3511-3513 (Aug. 28, 2012).

Jones, Christopher. Nonfinal Office Action for U.S. Appl. No. 12/598,855. Mail Date Jun. 14, 2012.

Jones, Christopher. Nonfinal Office Action for U.S. Appl. No. 12/598,855. Mail Date Oct. 12, 2012.

Koh et al., "A Crystalline Mesoporous Coordination Copolymer with High Microporosity," Angew Chem Int'l, 2008, pp. 677-680, vol. 47.

Li et al., "Docking in Metal-Organic Frameworks", Science, 325, 855 (2009).

Burrows et al., "Post-Synthetic Modification of Tagged MOFs," Angew. Chem. Int. Ed. 47:8482-8486 (2008).

Ashton, Peter R. et al., "Hydrogen-Bonded Complexes of Aromatic Crown Ethers with (9-Anthracenyl) methylammonium Derivatives" J. Am. Chem. Soc., 1997, 119 (44), pp. 10641-10651.

Baharlou, Simin. International Preliminary Report on Patentability for PCT/US2009/046463. Date of Mailing: Dec. 16, 2010.

Banerjee et al., "High-Throughput Synthesis of Zeolitic Imidazolate Frameworks and Application to CO2 Capture," Science 319:939-943 (2008).

Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).

Barman et al., "Azulene Based Metal-Organic Frameworks for Strong Adsorption of H2," Chem. Commun. 46:7981-7983 (2010).

Barton et al., "Tailored Porous Materials," Chem. Mater. 11:2633-2656 (1999).

Bloch et al., "Metal Insertion in a Microporous Metal-Organic Framework Lined with 2,2'-Bipyridine" J. Am. Chem. Soc. 132:14382-14384 (2010).

(56) References Cited

OTHER PUBLICATIONS

Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Highly efficient separation of carbon dioxide by a metal-organic framework replete with open metal sites," Proc. Natl. Acad. Sci. USA 106:20637-20640 (2009).
Britt et al., "Ring-Opening Reactions Within Metal-Organic Frameworks," Inorg. Chem. 49:6387-6389 (2010).
Carlucci et al., "Nanoporous three-dimensional networks topologically related to cooperite from the self-assembly of copper(I)centres and 1,2,4,5-tetracyanobenzene," New J. Chem. 23(23):397-401 (1999).
Carlucci, Lucia et al., "Polycatenation, polythreading and polyknotting in coordination network chemistry" Coordination Chemistry Reviews 246, 2003, pp. 247-289.
Caskey et al., "Dramatic Tuning of CO2 Uptake via Metal Substitution in a Coordination Polymer with Cylindrical Pores," JACS 130(33):10870-10871 (2008).
Caskey et al., "Selected Applications of Metal-Organic Frameworks in Sustainable Energy Technologies," Material Matters 4.4:111 (2009).
Centrone et al., "Raman Spectra of Hydrogen and Deuterium Adsorbed on a Metal-Organic Framework," Chem. Phys. Lett. 411:516-519 (2005).
Chae et al., "Tertiary Building Units: Synthesis, Structure, and Porosity of a Metal-Organic Dendrimer Framework (MOD-1)," J. Am. Chem. Soc. 123:11482-11483 (2001).
Chae et al., "Design of Frameworks with Mixed Triangular and Octahedral Building Blocks Exemplified by the Structure of [Zn4O(TCA)2] Having the Pyrite Topology," Angew. Chem. Int. Ed. 42:3907-3909 (2003).
Chae et al., "A Route to High Surface Area, Porosity and Inclusion of Large Molecules in Crystals," Nature427, 523-527 (2004); Featured in (1) Chemical & Engineering News magazine, Feb. 9, 2004, (2) BBC World Service, Feb. 4, (3) New Scientist, Feb. 4.
Chen et al., "Cu2(ATC)6H2O: Design of Open Metal Sites in Porous Metal-Organic Crystals (ATC: 1,3,5,7-adamantane tetracarboxylate)," J. Am. Chem. Soc. 122:11559-11560 (2000).
Chen et al., "Interwoven Metal-Organic Framework on a Periodic Minimal Surface with Extra-Large Pores," Science 291:1021-1023 (2001); Featured in Chemical and Engineering News, Feb. 21, 2001.
Chen et al., "Transformation of a Metal-Organic Framework from the NbO to PtS Net," Inorg. Chem. 41:181-183 (2005).
Chen et al., "High H2 Adsorption in a Microporous Metal-Organic Framework with Open-Metal Sites," Angew. Chem. Int. Ed. 44:4745-4749 (2005).
Chen et al., "A Microporous Metal-Organic Framework for Gas-Chomatographic Separation of Alkanes," Angew. Chem. Int. Ed. 45:1390-1393 (2006).
Cho et al., "A metal-organic framework material that functions as an enantioselective catalyst for olefin epoxidation," Chem. Comm. 24:2563-2565 (2006).
Choi et al., "Heterogeneity within Order in Crystals of a Porous Metal Organic Framework," J. Am. Chem. Soc. 133:11920-11923 (2011).
Cote et al., "Porous, Crystalline, Covalent Organic Frameworks," Science 310:1166-1170 (2005).
Cote et al., "Reticular Synthesis of Microporous and Mesoporous 2D Covalent Organic Frameworks," J. Am. Chem. Soc. 129:12914-12915 (2007).
Czaja et al., "Industrial applications of metal-organic frameworks," Chemical Society Reviews 38(5):1284-1293 (2009).
Delgado-Friedrichs et al., "Three-Periodic Nets and Tilings: Regular and Quasiregular Nets," Acta Cryst. A59:22-27 (2003).
Delgado-Friedrichs et al., "Three-Periodic Nets and Tilings: Semiregular Nets," Acta Cryst. A59:515-525 (2003).
Delgado-Friedrichs et al., "The CdSO4, Rutile, Cooperate and Quartz Dual Nets: Interpenetration and Catenation," Solid State Sciences 5:73-78 (2003).
Ockwig et al., "Reticular Chemistry: Occurrence and Taxonomy of Nets, and Grammar for the Design of Frameworks," Acc. Chem. Res. 38:176-182 (2005).
Delgado-Friedrichs et al. "What Do We Know About Three-Periodic Nets?," J. Solid State Chem. 178:2533-2554 (2005).
Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Demir et al., "Role of Copper Species in the Oxidative Dimerization of Arylboronic Acids: Synthesis of Symmetrical Biaryls," Journal of Organic Chemistry 68(26):10130-10134 (2003).
Deng et al., "Multiple Functional Groups of Varying Ratios in Metal-Organic Frameworks," Science 327:846-850 (2010).
Deng et al., "Robust dynamics" Nature Chem. 2:439-443 (2010).
Doonan et al., "Isoreticular Metalation of Metal-Organic Frameworks," J. Am. Chem. Soc. 131:9492-9493 (2009).
Doonan, C., "Hydrogen Storage in Metal-Organic Frameworks," Annual Merit Review Proceedings of DOE Hydrogen Program, May 22, 2009.
Doonan et al., "Exceptional ammonia uptake by a covalent organic framework," Nature Chem. 2:235-238 (2010).
Duren et al., "Design of New Materials for Methane Storage," Langmuir 20:2683-2689 (2004).
Eddaoudi et al., "Design and Synthesis of Metal-Organic Frameworks with Permanent Porosity," In Topics in Catalysis, G. A. Somorjai and J. M. Thomas, Eds., 9:105 (1999).
Eddaoudi et al., "Highly Porous and Stable Metal-Organic Framework: Structure Design and Sorption Properties," J. Am. Chem. Soc. 121:1391-1397 (2000).
Eddaoudi et al., "Porous Metal-Organic Polyhedra: 25 Å Cuboctahedron Constructed from Twelve Cu2(CO2)4 Paddle-Wheel Building Blocks," J. Am. Chem. Soc. 123:4368-4369 (2001).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Geometric Requirements and Examples of Important Structures in the Assembly of Square Building Blocks," Proc. Natl. Acad. Sci. 99:4900-4904 (2002).
Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Eddaoudi et al., "Cu2[o-Br-C6H3(CO2)2](H2O)2•(DMF)8(H2O)2: A Framework Deliberately Designed to have the NbO Structure Type," J. Am. Chem. Soc.124:376-377 (2002).
Ferragut et al., "Positronium Formation in Porous Materials for Antihydrogen Production,"J. Phys. Conf. Ser. 225:1-8 (2010).
Furukawa et al., "Crystal Structure, Dissolution, and Deposition of a 5 nm Functionalized Metal-Organic Great Rhombicuboctahedron," J. Am. Chem. Soc. 128:8398-8399 (2006).
Furukawa et al., "Independent verification of the saturation hydrogen uptake in MOF-177 and establishment of a benchmark for hydrogen adsorption in metal-organic frameworks," J. Mater. Chem. 17:3197-3204 (2007).
Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).
Furukawa et al., "Storage of Hydrogen, Methane, and Carbon Dioxide in Highly Porous Covalent Organic Frameworks for Clean Energy Applications," J. Am. Chem. Soc. 25:8876-8883 (2009).
Furukawa et al., "Ultra-High Porosity in Metal-Organic Frameworks," Science 239:424-428 (2010).
Glover et al., "MOF-74 building unit has a direct impact on toxic gas adsorption," J. Chem. Eng. Sci. 66:163-170 (2011).
Gould et al., "The Amphidynamic Character of Crystalline MOF-5: Rotational Dynamics in a Free-Volume Environment," J. Am. Chem. Soc. 130:3246-3247 (2008).
Goebel, Matthias, Supplemental European Search Report and Written Opinion for EP08826913. Date of Completion of Search and Written Opinion: Nov. 10, 2010.

(56) References Cited

OTHER PUBLICATIONS

Goebel, Matthias, Supplemental European Search Report and Written Opinion for EP08754337. Date of Completion of Search and Written Opinion: Dec. 3, 2010.

Gonzalez-Arellano et al., "Homogeneous and heterogeneous Au(III) Schiff base-complexes as selective and general catalysts for self-coupling of aryl boronic acids," Chem. Comm. 15:1990-1992 (2005).

Grzesiak et al., "Polymer-Induced Heteronucleation for the Discovery of New Extended Solids," Angew. Chem. Int. Ed. 45:2553-2556 (2006).

Halper et al., "Topological Control in Heterometallic Metal-Organic Frameworks by Anion Templating and Metalloligand Design," J. Am. Chem. Soc. 128:15255-15268 (2006).

Han, Ss et al., "Improved designs of metal-organic frameworks for hydrogen storage" Angew. Chem. Int. Ed. 2007, 46, pp. 6289-6292.

Han et al., "Covalent Organic Frameworks as Exceptional Hydrogen Storage Materials," J. Am. Chem. Soc. 130: 11580-11581 (2008).

Hayashi et al., "Zeolite A Imidazolate Frameworks," Nature Materials 6:501-506 (2007).

Hexiang et al., "Multiple Functional Groups of Varying Rations in Metal-Organic Frameworks," Science 327 (5967):846-850 (2010).

Holler et al., "The first dinitrile frameworks of the rare earth elements: [LnCl3(1,4-Ph(CN)2] and [Ln2Cl6(1,4Ph(CN)2], Ln = Sm, Gd, Tb, Y; Access to novel metal-organic frameworks by solvent free synthesis in molten 1,4-benodinitrile," Inorganic Chemistry 47(21): 10141-9 (2008).

Honda, Masashi, International Preliminary Report on Patentability for PCT/US2008/051859. Date of Issuance of the Report: Jul. 28, 2009.

Howe, Patrick. International Search Report and Written Opinion for PCT/US2009/068849. Date of Mailing of the Search Report: Jun. 4, 2010.

Howe, Patrick. International Search Report and Written Opinion for PCT/US2010/022777. Date of Mailing: Jun. 7, 2010.

Huang et al., "Thermal Conductivity of Metal-Organic Framework 5 (MOF-5): Part II. Measurement," Int. J. Heat Mass Transfer 50:405-411 (2007).

Hunt et al., "Reticular Synthesis of Covalent Organic Borosilicate Frameworks," J. Am. Chem. Soc. 130: 11872-11873 (2008).

Isaeva et al., "Metal-organic frameworks-new materials for hydrogen storage," Russian Journal of General Chemistry 77(4):721-739 (2007).

Jeong et al., "Asymmetric Catalytic Reactions by NbO-Type Chiral Metal-Organic Frameworks," Chem. Sci. 2:877-882 (2011).

Kaderi et al., "Designed Synthesis of 3D Covalent Organic Frameworks," Science 316:268-272 (2007).

Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).

Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).

Kim, Su Mi, International Search Report and Written Opinion for PCT/US2009/068731. Date of Mailing: Aug. 19, 2010.

Kim, Su Mi, International Search Report and Written Opinion, Date of Mailing: Feb. 24, 2010, International Application Number: PCT/US09/46463.

Kim, Su Mi. International Search Report for PCT/US2010/039154. Date of Mailing: Feb. 23, 2011.

Kirai et al., "Homocoupling of arylboronic acids catalyzed by 1,10-phenanthroline—ligated copper complexes in air," European Journal of Organic Chemistry 12:1864-1867 (2009).

Klaes, Daphne. International Search Report and Written Opinion for PCT/US2010/021201. Date of Mailing: Apr. 27, 2010.

Koza et al., "An efficient High Yielding Approach for the Homocoupling of Aryl Boronic Acids," Synthesis 15:2183-2186 (2002).

Kyoungmoo et al., "A Crystalline Mesoporous Coordination Copolymer with High Microporosity," Angew. Chem. Int. Ed. 47(4):677-680 (2008).

Lee, Ji Min. International Search Report for PCT/US2010/039284. Date of Mailing: Feb. 22, 2011.

Li et al., "Coordinatively Unsaturated Metal Centers in the Extended Porous Framewokr of Zn3(BDC)3-6CH3OH (BDC=1,4-Benzenedicarboxylate)," J. Am. Chem. Soc. 2186-2187 (1998).

Li et al., "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).

Li et al., "Porous Germanates: Synthesis, Structure and Inclusion Properties of Ge7O14.5F2-[(CH3)2NH2]3(H2O)O.86," J. Am. Chem. Soc. 120:8567-8568 (1998).

Li et al., "Transformation of Germanium Dioxide to 4-Connected Porous Germanate Net," J. Am. Chem. Soc. 10569-10570 (1998).

Li et al., "An Open-Framework Germanate with Polycubane-Like Topology," Angew. Chem. INt. Ed., 38:653-655 (1999).

Li et al., "Supertetrahedral Sulfide Crystals with Giant Cavities and Channels," Science 283:1145-1147 (1999).

Li et al., "Non-interpenetrating Indium Sulfide with a Supertetrahedral Cristobalite Famework," J. Am. Chem. Soc. 121:6096-6097 (1999).

Li et al., "Design and Synthesis of an Exceptionally Stable and Highly Porous Metal-Organic Framework," Science 402:276-279 (1999); Featured in (1) Chemical and Engineering News (Nov. 22, 1999) and (2) Science News (Nov. 20, 1999).

Li et al., "Ge2ZrO6F2 (H2DAB)H2O: A 4-Connected Microporous Material with "Bow Tie" Building Units and an Exceptional Proportion of 3-Rings," J. Am. Chem. Soc. 122:12409-12410 (2000).

Li et al., "20 A [Cd4In16S35]14-Supertetrahedral T4 Clusters as Building Units in Decorated Cristobalite Frameworks," J. Am. Chem Soc. 123:4867-4868 (2001).

Li et al., "[Cd16In64S134]44-: 31-Å Tetrahedron with a Large Cavity," Angew. Chem. Int. Ed 42:1819-1821 (2003).

Li et al., "A metal-organic framework replete with ordered donor-acceptor catenanes," Chem. Commun. 46:380-382 (2010).

Li et al., "A Catenated Strut in a Catenated Metal-Organic Framework," Angew. Chem. Int. Ed. 49:6751-6755 (2010).

Linder, Nora. International Preliminary Report on Patentability for PCT/US2010/022777. Date of Mailing: Aug. 11, 2011.

Stallmach et al., "NMR Studies on the Diffusion of Hydrocarbons on the Metal-Organic Framework Material MOF-5," Angew. Chem. Int. Ed. 45:2123-2126 (2006).

Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).

Sudik et al., "Metal-Organic Frameworks Based on Trigonal Prismatic Building Blocks and the New "acs" Topology," Inorg. Chem. 44:2998-3000 (2005).

Sudik et al., "A Metal-Organic Framework with a Hierarchical System of Pores and Tetrahedral Bbuilding Blocks," Angew. Chem. Int. Ed. 45:2528-2533 (2006).

Tranchemontagne et al. "Metal-Organic Frameworks with High Capacity and Selectivity for Harmful Gases," Proc. Natl. Acad. Sci. USA 105:11623-11627 (2008).

Tranchemontagne et al., "Reticular Chemistry of Metal-Organic Polyhedra," Angew. Chem. Int. Ed., 2008, 47:5136-5147 (2008).

Tranchemontagne et al., "Room Temperature Synthesis of Metal-organic Frameworks: MOF-5, MOF-74, MOF-177, MOF-199, and IRMOE-0," Tetrahedron 64:8553-8557 (2008).

Tranchemontagne et al. "Secondary Building Units, Nets and Bonding in the Chemistry of Metal-Organic Frameworks," Chem. Soc. Rev. 38:1257-1283 (2009).

Uribe-Romo et al., "A Crystalline Imine-Linked 3-D Porous Covalent Organic Framework," J. Am. Chem. Soc. 131:4570-4571 (2009).

Uribe-Romo et al., "Crystalline Covalent Organic Frameworks with Hydrazone Linkages," J. Am. Chem. Soc. 133: 11478-11481 (2011).

Vairaprakash et al., "Synthesis of Metal-Organic Complex Arrays," J. Am. Chem. Soc. 133:759-761 (2011).

Valente et al., "Metal-organic Frameworks with Designed Chiral Recognition Sites," Chem. Commun. 46:4911-4913 (2010).

(56) References Cited

OTHER PUBLICATIONS

Vodak et al., "Metal-Organic Frameworks Constructed from Pentagonal Antiprismatic and Cuboctahedral Secondary Building Units," Chem. Commun. 2534-2535 (2001).
Vodak et al., "One-Step Synthesis and Structure of an Oligo(spiro-orthocarbonate)," J. Am. Chem. Soc.124 (18):4942-4943 (2002).
Vodak et al., "Computation of Aromatic C3N4 Networks and Synthesis of the Molecular Precursor N(C3N3)3C16," Chem. Eur. J. 9:4197-4201 (2003).
Walton et al., "Understanding Inflections and Steps in Carbon Dioxide Adsorption Isotherms in Metal-Organic Frameworks," J. Am. Chem. Soc.130:406-407 (2008).
Wang et al., "Colossal Cages in Zeolitic Imidazolate Frameworks as Selective Carbon Dioxide Reservoirs," Nature 453:207-211 (2008).
Wong-Foy, AG et al., "Exceptional H2 saturation uptake in microporous metal-organic frameworks" J. Am. Chem. Soc., 2006, 128, pp. 3494-3495.
Yaghi et al., "Selective binding and removal of guests in a microporous metal-organic framework," Nature, Dec. 1995, pp. 703-706, vol. 378.
Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.
Yaghi et al., "Presence of Mutually Interpenetrating Sheets and Channels in the Extended Structure of Cu(4,4'-Bipyndine)Cl," Angew. Chem. Int. Ed. Engl., 1995, 34, 207-209.
Yaghi et al., "The Utility of Polymeric Matrices in the Preparation of Single Crystals of Coordination Solids: Synthesis and Structure of CuII(1,4-C4H4N2)(C4O4)(OH2)4," J. Solid State Chem., 1995, 117, 256-260.
Yaghi et al., "Open-Framework Solids with Diamond-Like Structures Prepared from Clusters and Metal-Organic Building Blocks,"Mater. Res. Soc. Symp. Proc., 1995, 371, 15.
Yaghi et al., "Hydrothermal Synthesis of a Metal-Organic Framework Containing Large Rectangular Channels," J. Am. Chem. Soc., 1995, 117, 10401-10402.
Yaghi et al., "Construction of Microporous Materials from Molecular Building Blocks," Fundamental Materials Research, T. J. Pinnavaia and M. F. Thorpe, eds., vol. II, Plenum: New York, p. 111 (1995).
Yaghi et al., "T-Shaped Molecular Building Units in the Porous Structure of Ag(4,4'-bpy) NO3," J. Am. Chem. Soc., 1996, 118, 295-296.
Yaghi et al., "Construction of Porous Solids from Hydrogen-Bonded Metal Complexes of 1,3,5-Benzenetricarboxylic Acid," J. Am. Chem. Soc., 1996, 118, 9096-9101.
Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).
Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.
Yaghi et al., "Crystal Growth of Extended Solids by Nonaqueous Gel Diffusion," Chem. Mater., 1997, 9, 1074-1076.
Yaghi et al., "A Molecular Railroad with Large Pores: Synthesis and Structure of Ni(4,4'-bpy)2.5(H2O)2(ClO4)2.1.5(4,4'-bpy)2(H2O)," Inorg. Chem., 1997, 36, 4292-4293.
Yaghi et al., "Construction of a New Open-Framework Solid form 1,3,5-Cyclohexanetricarboxylate and Zinc(II) Building Blocks," J. Chem. Soc. Dalton Trans. 2383-2384 (1997).
Yaghi et al., "Synthesis and Structure of a Metal-Organic Solid Having the Cadmium (II) Sulfate Net," Mater. Res. Soc. Symp. Proc. 453:127, (1997).
Yaghi et al., "Designing Microporosity in Coordination Solids," Modular Chemistry, J. Michl, Ed., Kluwer: Boston, p. 663 (1997).
Yaghi et al., "Synthetic Strategies, Structure Patterns, and Emerging Properties in the Chemistry of Modular Porous Solids," Acc. Chem. Res. 31:474-484 (1998).

Yaghi et al., "Transformation of Germanium Dioxide to 4-Connected Porous Germanate Net," J. Am. Chem. Soc., 20:10569-10570 (1998).
Yaghi et al., "Design of Solids from Molecular Building Blocks: Golden Opportunities for Solid State Chemistry," J. Solid State Chem. 152, 1-2 (2000).
Yaghi et al., "A Molecular World Full of Holes," Chem. Innov. p. 3 (2000).
Yaghi et al., "Reticular Synthesis and the Design of New Materials," Nature 423:705-714 (2003).
Yaghi et al., "Metal-Organic Frameworks: A Tale of Two Entanglements," Nature materials 6:92-93 (2007).
Yaghi et al., "Reticular Chemistry and Metal-Organic Frameworks for Clean Energy," MRS Bulletin 34:682-690 (2009).
Young, Lee W., International Search Report and Written Opinion, Date of Mailing of Report: May 7, 2008, International Application No. PCT/US08/51859.
Young, Lee W., "International search Report and Written Opinion," PCT/US08/06008, United States Patent & Trademark Office, Aug. 20, 2008.
Young, Lee W., International Search Report and Written Opinion, Date of Mailing: Dec. 2, 2008, International Application No. PCT/US08/77741.
Young, Lee W., International Search Report and Written Opinion, Date of Mailing: Jan. 12, 2009, International Application No. PCT/US08/70149.
Young, Jung Doo. International Search Report for PCT/US2010/050170. Date of Mailing: Jun. 8, 2011.
Zhang et al., "Docking in Metal-Organic Frameworks," Science 325:855-859 (2009).
Zhao et al., "Rigid-Strut-Containing Crown Ethers and [2]Catenanes for Incorporation into Metal-Organic Frameworks," Chem. Eur. J. 15:13356-13380 (2009).
Zhao, Wei. The First Office Action for Chinese Application No. 200880003157.2. The State Intellectual Property Office of the People's Republic of China. Issue Date: Aug. 5, 2011.
Zhofu et al., "A Nearly Planar Water Sheet Sandwiched between Strontium-Imidazolium Carboxylate Coordination Polymers," Inorg. Chem. 44:5200-5202 (2005).
Lawrence, Frank M. Nonfinal Office Action for U.S. Appl. No. 12/699,616. Mail Date Apr. 10, 2012.
Lawrence, Frank M. Nonfinal Office Action for U.S. Appl. No. 12/699,616. Mail Date Aug. 3, 2012.
Lee et al., "Synthesis and Gas Sorption Properties of a Metal-Azolium Framework (MAF) Material," Inorganic Chemistry, Nov. 2, 2009, pp. 9971-9973, vol. 48, No. 21.
McKeown et al., "Phthalocyanine-Based Nanoporous Network Polymers," Chem. Comm. 23:2780-2781 (Oct. 31, 2002).
McKeown et al., "Porphyrin-Based Nanoporous Network Polymers," Chem. Comm. 23:2782-2783 (Oct. 31, 2002).
Morris et al., "Framework mobility in the metal-organic framework crystal IRMOF-3: Evidence for aromatic ring and amine rotation," Journal of Molecular Structure 1004:94-101 (2011).
Morris et al., "NMR and X-ray Study Revealing the Rigidity of Zeolitic Imidazolate Frameworks," J. Phys. Chem. 116 (24):13307-13312 (Jun. 1, 2012).
Morris et al., "Synthesis, Structure, and Metalation of Two New Highly Porous Zirconium Metal-Organic Frameworks," Inorg. Chem. 51:6443-6445 (Jun. 7, 2012).
O'Keeffe et al., "Deconstructing the Crystal Structures of Metal-Organic Frameworks and Related Materials into Their Underlying Nets," Chem. Rev. 112(2):675-702 (Feb. 8, 2012).
Queen et al., "Site-Specific CO2 Adsorption and Zero Thermal Expansion in an Anisotropic Pore Network," J. Phys. Chem. C, 115:24915-24919 (Nov. 8, 2011).
Rinkel, Bert. Extended European Search Report for European Patent Application EP08713961. Mail Date Jan. 2, 2012.
Rouseau-Jager, Nadia, International Search Report and Written Opinion, PCT/US2011/024671, European Patent Office, Dec. 13, 2011.
Sines, Brian J. Nonfinal Office Action for U.S. Appl. No. 13/142,564. Mail Date Jul. 9, 2012.

(56) References Cited

OTHER PUBLICATIONS

Song et al., "A Multiunit Catalyst with Synergistic Stability and Reactivity: A PolyoxometalateMetal Organic Framework for Aerobic Decontamination," J. Am. Chem. Soc. 133(42):16839-16846 (Sep. 13, 2011).
Spitler et al., "Lewis Acid Catalyzed Formation of Two-Dimensional Phthalocyanine Covalent Organic Framewokrs." Nature Chem. 2:672-677 (Jun. 20, 2010).
Tilford et al., "Facile Synthesis of a Highly Crystalline, Covalently Porous Boronate Network," 18(22):5296-5301 (Oct. 11, 2006).
Tranchemontagne et al., "Hydrogen Storage in New Metal-Organic Frameworks," J. Phys. Chem. C 116 (24):13143-13151 (May 24, 2012).
Wan et al, "A Belt-Shaped, Blue Luminescent, and Semiconducting Covalent Organic Framework." Angew. Chem. Int. Ed. 47:8826-8830 (2008).
Wan et al., "Covalent Organic Frameworks with High Charge Carrier Mobility," Chem. Mater. 23:4094-4097 (Aug. 22, 2011).
Young, Jung Doo. International Search Report and Written Opinion for PCT/US2011/053423. Date of mailing of ISR Jul. 23, 2012.
Young, Jung Doo, "International Search Report and Written Opinion for PCT/2012/023516." Date of mailing of the International Search Report Oct. 19, 2012.
Zhou et al., "Introduction to Metal-Organic Frameworks," Chemical Reviews 112:673-674 (Jan. 26, 2012).

\* cited by examiner

PREPARATION OF METAL-TRIAZOLATE FRAMEWORKS

STATEMENT REGARDING FEDERALLY SPONSORED RESEARCH

This invention was made with government support under Grant No. WO911NF-06-1-0405, awarded by the United States Army/Army Research Office, Grant No. DE-SC0001342, awarded by the United States Department of Energy, and Grant No. N00164-08-C-GS31, awarded by the United States Navy. The government has certain rights in the invention.

CROSS REFERENCE TO RELATED APPLICATIONS

This application claims priority under 35 U.S.C. §119 to U.S. Provisional Application Ser. No. 61/434,936 filed Jan. 21, 2011, the disclosure of which is incorporated herein by reference in its entirety.

FIELD OF THE INVENTION

This invention relates to metal porous frameworks and methods of use thereof.

BACKGROUND

A large segment of the global economy ($350 billion) is based on the use of metal-organic frameworks in petrochemical cracking, ion-exchange for water softening and purification, and in the separation of gases. Metal-organic frameworks (MOFs) are porous crystals whose structures are constructed from metal-containing cationic units and anionic organic links. MOFs with desirable porosity and stability are typically, and almost exclusively, made from organic links of carboxylates, imidazolates, and tetrazolates.

SUMMARY

The disclosure provides for novel metal-triazolate (MET) frameworks. In a certain embodiment, the disclosure provides for MET frameworks comprising one or more cores comprising structural Formula I:

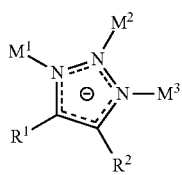

wherein, $M^1$, $M^2$ and $M^3$ are independently selected metal or metals ions, and wherein at least two of $M^1$, $M^2$ and $M^3$ are coordinated to nitrogens;

$R^1$-$R^2$ are independently selected from the group comprising H, optionally substituted FG, optionally substituted ($C_1$-$C_6$)alkyl, optionally substituted ($C_1$-$C_6$)alkenyl, optionally substituted ($C_1$-$C_6$)alkynyl, optionally substituted hetero-($C_1$-$C_6$)alkyl, optionally substituted hetero-($C_1$-$C_6$)alkenyl, optionally substituted hetero-($C_1$-$C_6$)alkynyl, optionally substituted cycloalkyl, optionally substituted cycloalkenyl, optionally substituted aryl, optionally substituted heterocycle, optionally substituted mixed ring system, $-C(R^7)_3$, $-CH(R^7)_2$, $-CH_2R^7$, $-C(R^8)_3$, $-CH(R^8)_2$, $-CH_2R^8$, $-OC(R^7)_3$, $-OCH(R^7)_2$, $-OCH_2R^7$, $-OC(R^8)_3$, $-OCH(R^8)_2$, $-OCH_2R^8$,

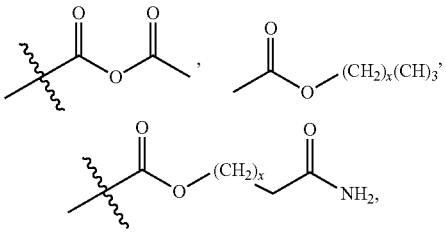

and wherein $R^1$ and $R^2$ are linked together to form a substituted or unsubstituted ring selected from the group comprising cycloalkyl, cycloalkenyl, heterocycle, aryl and mixed ring system;

$R^7$ is selected from the group comprising halo, hydroxyl, amine, thiol, cyano, carboxyl, optionally substituted ($C_1$-$C_6$) alkyl, optionally substituted ($C_1$-$C_6$)alkenyl, optionally substituted ($C_1$-$C_6$)alkynyl, optionally substituted hetero-($C_1$-$C_6$)alkyl, optionally substituted hetero-($C_1$-$C_6$)alkenyl, hemiacetal, hemiketal, acetal, ketal, and orthoester;

$R^8$ is one or more substituted or unsubstituted rings selected from the group comprising cycloalkyl, cycloalkenyl, aryl, heterocycle, and mixed ring system; and X is a number from 0 to 3.

In a further embodiment, MET frameworks disclosed herein comprise a cores of structural Formula I:

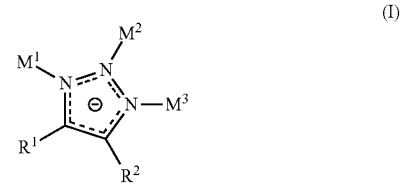

wherein, $M^1$, $M^2$ and $M^3$ are independently selected metal ions selected from the group comprising $Mg^{2+}$, $Mn^{2+}$, $Fe^{2+}$, $Co^{2+}$, $Zn^{2+}$, and $Cd^{2+}$, and wherein at least two of $M^1$, $M^2$ and $M^3$ are coordinated to nitrogens; and $R^1$-$R^2$ are H.

In a select embodiment, MET frameworks disclosed herein have the characteristics of frameworks presented in Table 4. Moreover, the disclosure also provides for MET frameworks that comprise dia framework geometry.

The disclosure provides for MET frameworks that contain metal ions selected from the group comprising $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}, Pt^{5+}, Pt^{4+}, Pt^{3+}, Pt^{2+}, Pt^+, Cu^{4+}, Cu^{3+}, Cu^{2+}, Cu^+, Ag^{3+}, Ag^{2+}, Ag^+, Au^{5+}, Au^{4+}, Au^{3+}, Au^{2+}, Au^+, Zn^{2+}, Zn^+, Zn, Cd^{2+}, Cd^+, Hg^{4+}, Hg^{2+}, Hg^+, B^{3+}, B^{2+}, B^+, Al^{3+}, Al^{2+}, Al^+, Ga^{3+}, Ga^{2+}, Ga^+, In^{3+}, In^{2+}, In^{1+}, Tl^{3+}, Tl^+, Si^{4+}, Si^{3+}, Si^{2+}, Si^+, Ge^{4+}, Ge^{3+}, Ge^{2+}, Ge^+, Ge, Sn^{4+}, Sn^{2+}, Pb^{4+}, Pb^{2+}, As^{5+}, As^{3+}, As^{2+}, As^+, Sb^{5+}, Sb^{3+}, Bi^{5+}, Bi^{3+}, Te^{6+}, Te^{5+}, Te^{4+}, Te^{2+}, La^{3+}, La^{2+}, Ce^{4+}, Ce^{3+}, Ce^{2+}, Pr^{4+}, Pr^{3+}, Pr^{2+}, Nd^{3+}, Nd^{2+}, Sm^{3+}, Sm^{2+}, Eu^{3+}, Eu^{2+}, Gd^{3+}, Gd^{2+}, Gd^+, Tb^{4+}, Tb^{3+}, Tb^{2+}, Tb^+, Db^{3+}, Db^{2+}, Ho^{3+}, Er^{3+}, Tm^{4+}, Tm^{3+}, Tm^{2+}, Yb^{3+}, Yb^{2+},$ and $Lu^{3+}$. In one embodiment, a MET framework disclosed herein contain divalent metal ions. Examples of divalent metal ions include, but are not limited to, $Be^{2+}, Mg^{2+}, Ca^{2+}, Sr^{2+}, Ba^{2+}, Sc^{2+}, Y^{2+}, Ti^{2+}, Zr^{2+}, V^{2+}, Nb^{2+}, Ta^{2+}, Cr^{2+}, Mo^{2+}, W^{2+}, Mn^{2+}, Re^{2+}, Fe^{2+}, Ru^{2+}, Os^{2+}, Co^{2+}, Rh^{2+}, Ir^{2+}, Ni^{2+}, Pd^{2+}, Pt^{2+}, Cu^{2+}, Ag^{2+}, Au^{2+}, Zn^{2+}, Cd^{2+}, B^{2+}, Al^{2+}, Ga^{2+}, Si^{2+}, Sn^{2+}, Pb^{2+}, Hg^{2+}, As^{2+}, Te^{2+}, La^{2+}, Ce^{2+}, Pr^{2+}, Sm^{2+}, Gd^{2+}, Nd^{2+}, Db^{2+}, Tb^{2+}, Tm^{2+}$ and $Yb^{2+}$. In a further embodiment, a MET framework disclosed herein contain divalent metal ions selected from the group comprising $Mg^{2+}, Mn^{2+}, Fe^{2+}, Co^{2+}, Zn^{2+},$ and $Cd^{2+}$.

The disclosure provides for MET frameworks that comprise one or more cores comprising one or more linking moieties of structural Formula II:

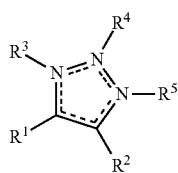

(II)

wherein:

$R^1$-$R^2$ are independently selected from the group comprising H; optionally substituted FG, optionally substituted ($C_1$-$C_6$)alkyl, optionally substituted ($C_1$-$C_6$)alkenyl, optionally substituted ($C_1$-$C_6$)alkynyl, optionally substituted hetero-($C_1$-$C_6$)alkyl, optionally substituted hetero-($C_1$-$C_6$)alkenyl, optionally substituted hetero-($C_1$-$C_6$)alkynyl, optionally substituted cycloalkyl, optionally substituted cycloalkenyl, optionally substituted aryl, optionally substituted heterocycle, optionally substituted mixed ring system, —C($R^7$)$_3$, —CH($R^7$)$_2$, —CH$_2$$R^7$, —C($R^8$)$_3$, —CH($R^8$)$_2$, —CH$_2$$R^8$, —OC($R^7$)$_3$, —OCH($R^7$)$_2$, —OCH$_2$$R^7$, —OC($R^8$)$_3$, —OCH($R^8$)$_2$, —OCH$_2$$R^8$,

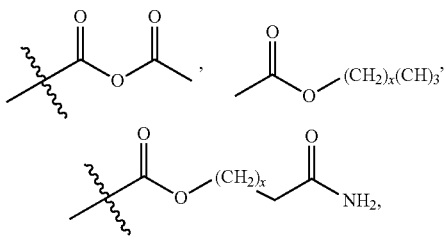

and wherein $R^1$ and $R^2$ are linked together to form a substituted or unsubstituted ring selected from the group comprising cycloalkyl, cycloalkenyl, heterocycle, aryl and mixed ring system;

$R^3$-$R^5$ are H or are absent when bound to a N atom that is doubly bonded to another atom;

$R^7$ is selected from the group comprising halo, hydroxyl, amine, thiol, cyano, carboxyl, optionally substituted ($C_1$-$C_6$) alkyl, optionally substituted ($C_1$-$C_6$)alkenyl, optionally substituted ($C_1$-$C_6$)alkynyl, optionally substituted hetero-($C_1$-$C_6$)alkyl, optionally substituted hetero-($C_1$-$C_6$)alkenyl, optionally substituted hetero-($C_1$-$C_6$)alkynyl, hemiacetal, hemiketal, acetal, ketal, and orthoester;

$R^8$ is one or more substituted or unsubstituted rings selected from the group comprising cycloalkyl, cycloalkenyl, aryl, heterocycle, and mixed ring system; and X is a number from 0 to 3.

The disclosure provides for MET frameworks that comprise one or more cores comprising one or more linking moieties of structural Formula II:

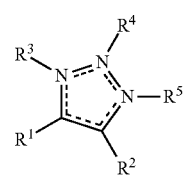

(II)

wherein:

$R^1$-$R^2$ are independently selected from the group comprising H, halo, amine, cyano, $CO_2H$, $NO_2$, $SO_3H$, $PO_3H$, optionally substituted ($C_1$-$C_4$)alkyl, optionally substituted ($C_1$-$C_4$) alkenyl, optionally substituted ($C_2$-$C_4$)alkynyl, optionally substituted hetero-($C_1$-$C_4$)alkyl, optionally substituted hetero-($C_1$-$C_4$)alkenyl, and optionally substituted hetero-($C_2$-$C_4$)alkynyl; and $R^3$-$R^5$ are H or are absent when bound to a N atom that is doubly bonded to another atom.

The disclosure provides for MET frameworks that comprise one or more cores comprising one or more linking moieties selected from the group comprising 2H-[1,2,3]triazole, 1H-[1,2,3]triazole, 4-chloro-2H-[1,2,3]triazole, 4-chloro-1H-[1,2,3]triazole, 4,5-dichloro-2H-[1,2,3]triazole, 4,5-dichloro-1H-[1,2,3]triazole, 4-bromo-2H-[1,2,3]triazole, 4-bromo-1H-[1,2,3]triazole, 4,5-dibromo-2H-[1,2,3]triazole, 4,5-dibromo-1H-[1,2,3]triazole, 4-fluoro-2H-[1,2,3]triazole, 4-fluoro-1H-[1,2,3]triazole, 4,5-difluoro-2H-[1,2,3]triazole, 4,5-difluoro-1H-[1,2,3]triazole, 4-iodo-2H-[1,2,3]triazole, 4-iodo-1H-[1,2,3]triazole, 4,5-diiodo-2H-[1,2,3]triazole, 4,5-diiodo-1H-[1,2,3]triazole, 5-trifluoromethyl-2H-[1,2,3]triazole, 5-trifluoromethyl-1H-[1,2,3]triazole, 4,5-bis-trifluoromethyl-2H-[1,2,3]triazole, 4,5-bis-trifluoromethyl-1H-[1,2,3]triazole, 2H-[1,2,3]triazole-4-ol, 1H-[1,2,3]triazole-4-ol, 2H-[1,2,3]triazole-4,5-diol, 1H-[1,2,3]triazole-4,5-diol, 2H-[1,2,3]triazole-4-carbonitrile, 1H-[1,2,3]triazole-4-carbonitrile, 2H-[1,2,3]triazole-4,5-dicarbonitrile, 1H-[1,2,3]triazole-4,5-dicarbonitrile, 2H-[1,2,3]triazole-4-ylamine, 1H-[1,2,3]triazole-4-ylamine, 2H-[1,2,3]triazole-4,5-diamine, 1H-[1,2,3]triazole-4,5-diamine, 4-methyl-2H-[1,2,3]triazole, 4-methyl-1H-[1,2,3]triazole, 4-ethyl-2H-[1,2,3]triazole, 4-ethyl-1H-[1,2,3]triazole, 4-propyl-2H-[1,2,3]triazole, 4-propyl-1H-1-[1,2,3]triazole, 4-butyl-2H-[1,2,3]triazole, 4-butyl-1H-[1,2,3]triazole, 4-isopropyl-2H-[1,2,3]triazole, 4-isopropyl-1H-[1,2,3]triazole, 4,5-diisopropyl-2H-[1,2,3]triazole, 4,5-diisopropyl-1H-[1,2,3]triazole, 4-tert-butyl-2H-[1,2,3]triazole, 4-tert-butyl-1H-[1,2,3]triazole, 4,5-di-tert-butyl-2H-[1,2,3]triazole, 4,5-di-tert-butyl-1H-[1,2,3]triazole, 2H-[1,2,3]triazole-4-carboxylic acid, 1H-[1,2,3]triazole-4-carboxylic acid, 2H-[1,2,3]triazole-4,5-dicarboxylic acid, 1H-[1,2,3]triazole-4,5-dicarboxylic acid, 2H-[1,2,3]triazole-4-carbaldehyde, 1H-[1,2,3]triazole-4-carbaldehyde, 2H-[1,2,3]triazole-4,5-dicarbaldehyde, 1H-[1, 2,3]triazole-4,5-dicarbaldehyde, 1-(2H-[1,2,3]triazole-4-yl)-ethanone, 1-(1H-[1,2,3]triazole-4-yl)-ethanone, 1-(5-acetyl-2H-[1,2,3]triazole-4-yl)-ethanone, 1-(5-acetyl-1H-[1,2,3]triazole-4-yl)-ethanone, 2H-[1,2,3]triazole-4-thiol, 1H-[1,2,3]triazole-4-thiol, 2H-[1,2,3]triazole-4,5-dithiol, 1H-[1,2,3]triazole-4,5-dithiol, 5-mercaptomethyl-2H-[1,2,3]triazole-4-thiol, 5-mercaptomethyl-1H-[1,2,3]triazole-4-thiol, (5-mercaptomethyl-2H-[1,2,3]triazole-4-yl)-methanethiol, (5-mercaptomethyl-1H-[1,2,3]triazole-4-yl)-methanethiol, 4-nitro-2H-[1,2,3]triazole, 4-nitro-1H-[1,2,3]triazole, 4,5-dinitro-2H-[1,2,3]triazole, 4,5-dinitro-1H-[1,2,3]triazole, 4-vinyl-2H-[1,2,3]triazole, 4-vinyl-1H-[1,2,3]triazole, 4,5-divinyl-2H-[1,2,3]triazole, 4,5-divinyl-1H-[1,2,3]triazole, 2H-[1,2,3]triazolo[4,5-c]pyridine, 3H-[1,2,3]triazolo[4,5-c]pyridine, 2H-[1,2,3]triazolo[4,5-b]pyridine, 3H-[1,2,3]triazolo[4,5-b]pyridine, 2H-[1,2,3]triazolo[4,5-d]pyrimidine, 3H-[1,2,3]triazolo[4,5-d]pyrimidine, 2H-[1,2,3]triazolo[4,5-b]pyrazine, 3H-[1,2,3]triazolo[4,5-b]pyrazine, dimethyl-(2H-[1,2,3]triazol-4-yl)-amine, dimethyl-(1H-[1,2,3]triazol-4-yl)-amine, N,N,N',N'-tetramethyl-2H-[1,2,3]triazol-4,5-diamine, and N,N,N',N'-tetramethyl-1H-[1,2,3]triazol-4,5-diamine.

The disclosure provides for MET frameworks that comprise one or more cores comprising one or more linking moieties of structural Formula II:

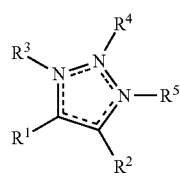

(II)

wherein:

$R^1$-$R^2$ are independently selected so as to either interact with one or more particular gases, to modulate the pore size of the MET framework, or combination thereof; and $R^3$-$R^5$ are H or are absent when bound to a N atom that is doubly bonded to another atom.

The disclosure provides for MET frameworks that once formed are then reacted with one or more post framework reactants. In particular, these post framework reactants add at least one effect, or in a certain embodiment at least two effects, to a MET framework of the disclosure including, but not limited to, modulating the gas storage ability of a MET framework; modulating the sorption properties of a MET framework; modulating the pore size of a MET framework; modulating the catalytic activity of a MET framework; modulating the conductivity of a MET framework; and modulating the sensitivity of a MET framework to the presence of an analyte of interest.

The disclosure also provides for MET frameworks that further comprise one or more guest species. In one embodiment, MET frameworks of the disclosure further comprise one or more absorbed or adsorbed chemical species. Examples of such absorbed or adsorbed chemical species include, but are not limited to, gases, optionally substituted ($C_1$-$C_{25}$) organic molecules, inorganic molecules, and combinations thereof. In a further embodiment, MET frameworks of the disclosure further comprise one or more absorbed or adsorbed chemical species selected from the group comprising argon, ammonia, carbon dioxide, carbon monoxide, hydrogen, amines, oxygen, ozone, nitrogen, nitrous oxide, organic dyes, polycyclic organic molecules, hydrogen sulfide, carbonyl sulfide, carbon disulfide, mercaptans, hydrocarbons, formaldehyde, diisocyanates, trichloroethylene, fluorocarbons, and combinations thereof. In a further embodiment, MET frameworks of the disclosure further comprise one or more absorbed or adsorbed chemical species selected from the group comprising argon, carbon dioxide, carbon monoxide, hydrogen, nitrogen, hydrogen sulfide, carbonyl sulfide, carbon disulfide, mercaptan, and combinations thereof. In a select embodiment, MET frameworks of the disclosure further comprise one or more absorbed or adsorbed chemical species selected from the group comprising carbon dioxide, carbon monoxide, or a combination thereof.

The disclosure also provides methods to separate or store one or more gases from a gas mixture comprising contacting the gas mixture with a MET framework disclosed herein. In one embodiment, the disclosure provides for separating one or more high density gases from a gas mixture by contacting the gas mixture with a MET framework disclosed herein. In a certain embodiment, the disclosure provides a method to separate or store one or more gases from a fuel gas stream comprising contacting the fuel gas stream with a MET framework disclosed herein, including, separating or storing one or more acid gases from a natural gas stream.

The disclosure provides methods to separate or store one or more gases from the exhaust of a combustion engine by contacting the exhaust with a MET framework disclosed herein. The disclosure provides methods to separate or store one or more gases from flue gas by contacting the flue-gas with a MET framework disclosed herein.

The disclosure also provides a device which comprises a MET framework disclosed herein. In a certain embodiment, a device which comprises a MET framework of the disclosure is a gas storage or gas separation device. Examples of such gas storage or gas separation devices, include, but are not limited to, purifiers, filters, scrubbers, pressure swing adsorption devices, molecular sieves, hollow fiber membranes, ceramic membranes, cryogenic air separation devices, and hybrid gas separation devices. In a certain embodiment, the device which comprises a MET framework disclosed herein includes, but are not limited to, carbon monoxide detectors, air purifiers, fuel gas purifiers, and devices to measure car emissions.

The disclosure provides for an electrical conductor which comprises a MET framework of the disclosure.

The disclosure provides for a catalyst which comprises a MET framework of the disclosure.

The disclosure also provides a chemical sensor which comprises a MET framework of the disclosure.

DETAILED DESCRIPTION

Figure 1:
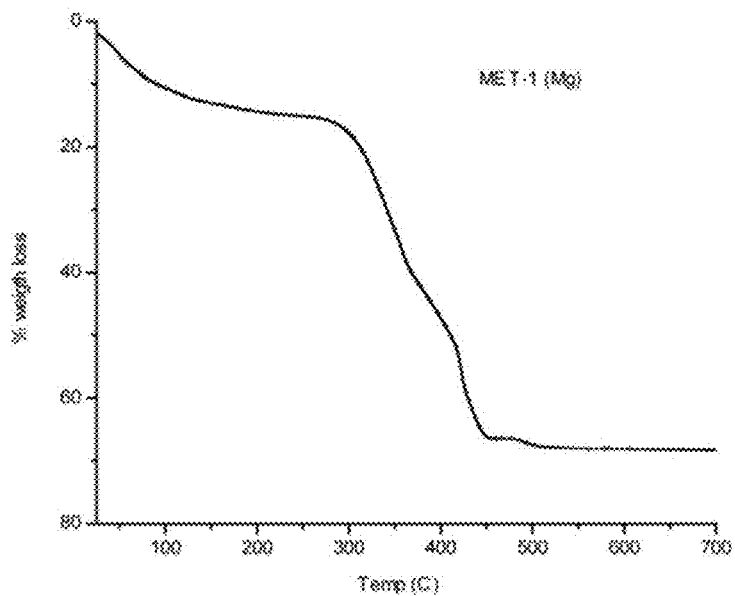
FIG. 1 provides a thermogravimetric curve for MET-1 when heated at a constant rate of 5° C./min in a continuous flow nitrogen atmosphere.
Figure 2:
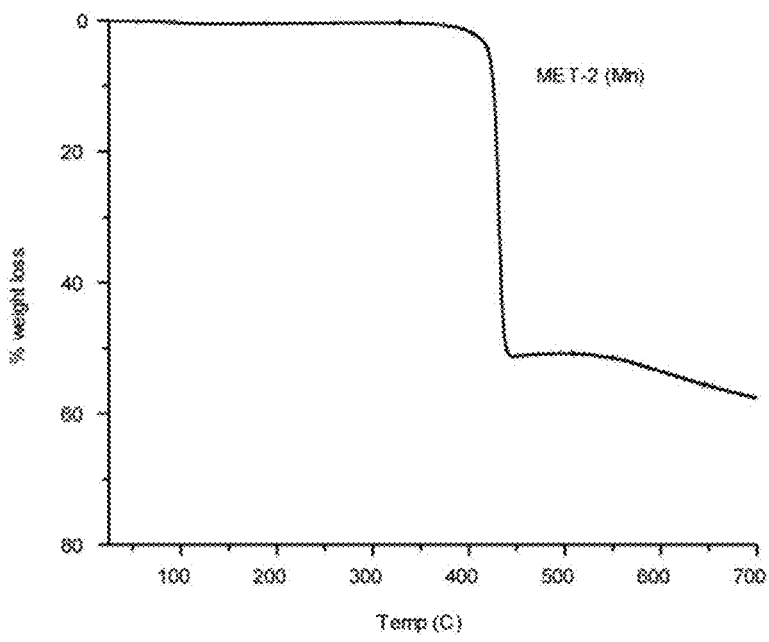
FIG. 2 provides a thermogravimetric curve for MET-2 when heated at a constant rate of 5° C./min in a continuous flow nitrogen atmosphere.
Figure 3:
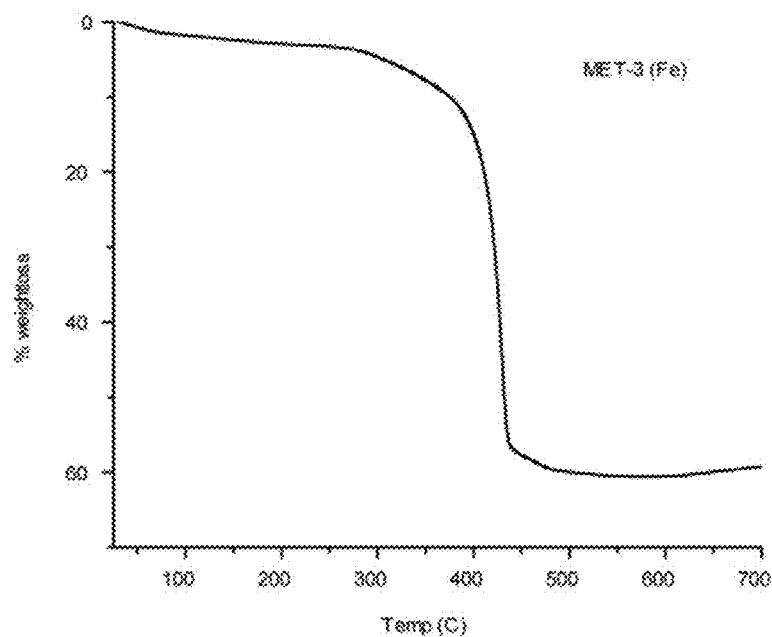
FIG. 3 provides a thermogravimetric curve for MET-3 when heated at a constant rate of 5° C./min in a continuous flow nitrogen atmosphere.
Figure 4:
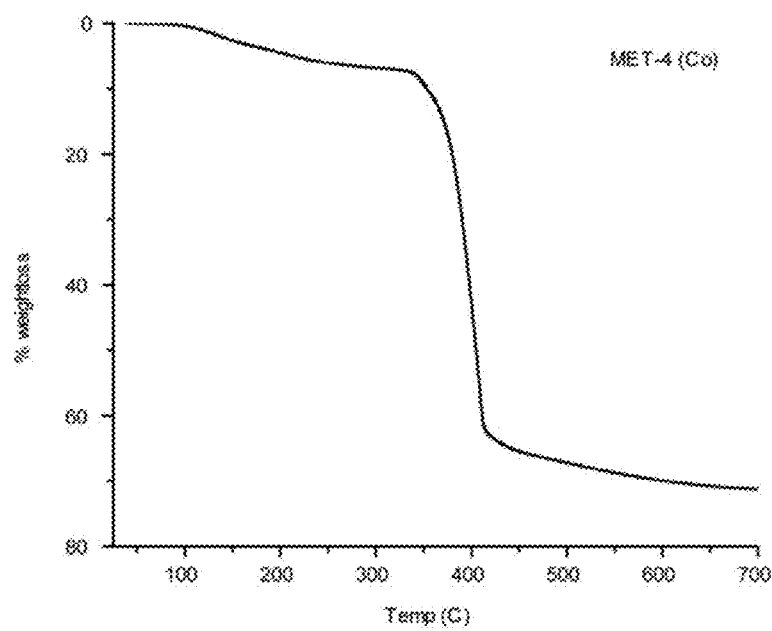
FIG. 4 provides a thermogravimetric curve for MET-4 when heated at a constant rate of 5° C./min in a continuous flow nitrogen atmosphere.
Figure 5:
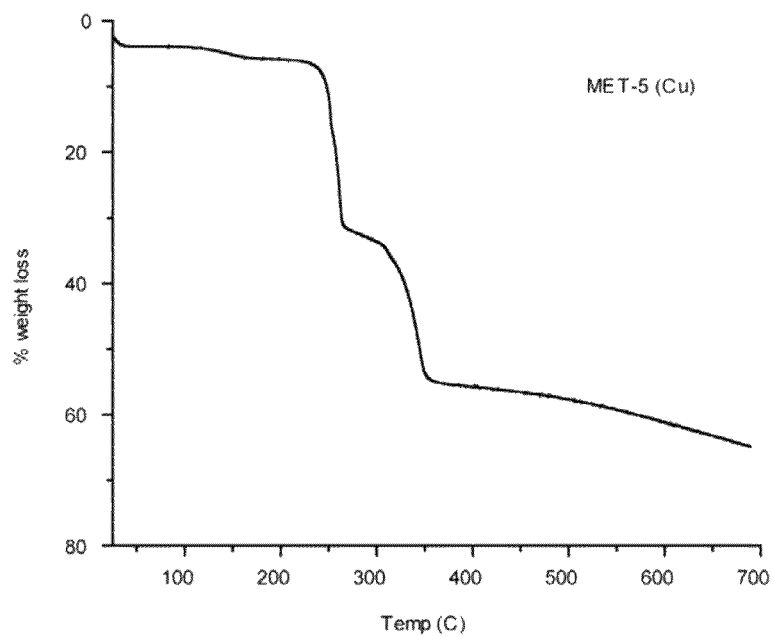
FIG. 5 provides a thermogravimetric curve for MET-5 when heated at a constant rate of 5° C./min in a continuous flow nitrogen atmosphere.
Figure 6:
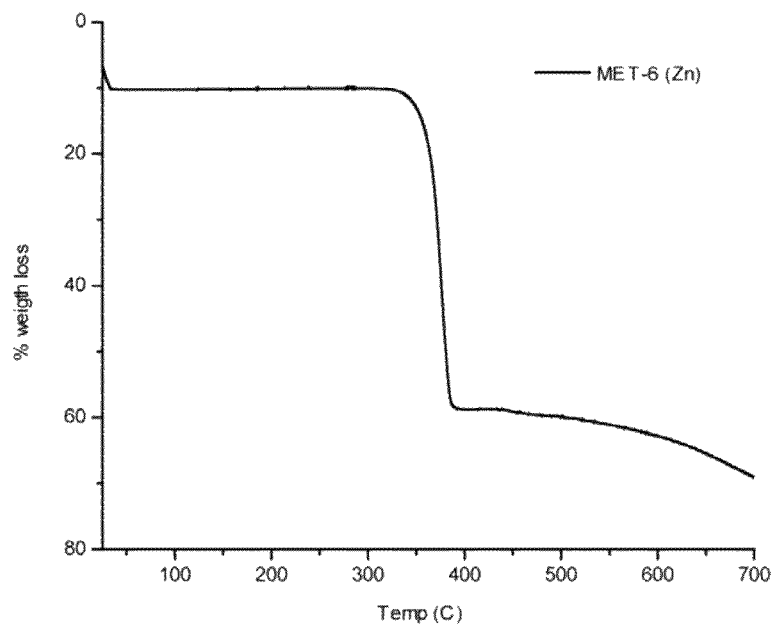
FIG. 6 provides a thermogravimetric curve for MET-6 when heated at a constant rate of 5° C./min in a continuous flow nitrogen atmosphere.

As used herein and in the appended claims, the singular forms "a," "and," and "the" include plural referents unless the context clearly dictates otherwise. Thus, for example, reference to "a pore" includes a plurality of such pore and reference to "the metal" includes reference to one or more metals known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned throughout the disclosure are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to similar or identical terms found in the incorporated references and terms expressly defined in this disclosure, the term definitions provided in this disclosure will control in all respects.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

A "metal" refers to a solid material that is typically hard, shiny, malleable, fusible, and ductile, with good electrical and thermal conductivity. "Metals" used herein refer to metals selected from alkali metals, alkaline earth metals, lanthanides, actinides, transition metals, and post transition metals.

A "metal ion" refers to an ion of a metal. Metal ions are generally Lewis Acids and can form coordination complexes. Typically, the metal ions used for forming a coordination complex in a framework are ions of transition metals.

The term "cluster" refers to identifiable associations of 2 or more atoms. Such associations are typically established by some type of bond-ionic, covalent, Van der Waal, coordinate and the like.

A "metal triazolate framework" or "MET," as used herein, refers to a framework of repeating cores having a plurality of metals linked by one or more linking moieties.

A "linking moiety" refers to a parent chain that contains triazole or a derivative thereof that binds a metal or metal ion or a plurality of metals or metal ions. A linking moiety may be further substituted post synthesis of a metal triazolate framework by reacting with one or more post-framework reactants.

The term "linking cluster" refers to one or more atoms capable of forming an association, e.g. covalent bond, polar covalent bond, ionic bond, and Van Der Waal interactions, with one or more atoms of another linking moiety, and/or one or more metal or metal ions. A linking cluster can be part of the parent chain itself, e.g. the nitrogen atoms in triazole, and/or additionally can arise from functionalizing the parent chain, e.g. adding carboxylic acid groups to the triazole-based parent chain. For example, a linking cluster can comprise $NN(H)N$, $N(H)NN$, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings and $CH(SH)_2$, $C(SH)_3$, $CH(NH_2)_2$, $C(NH_2)_3$, $CH(OH)_2$, $C(OH)_3$, $CH(CN)_2$, and $C(CN)_3$. Generally for a metal triazolate framework disclosed herein, the linking cluster(s) that bind one or metal or metal ions and/or associate with one or more atoms of another linking moiety comprise at least one, two, or all three nitrogen atoms of the triazole-based parent chain. But, the triazole-based parent chain may be further substituted with one or more linking clusters and can therefore form associations with one or more metal or metal ions and/or one or more atoms of another linking moiety in addition to, or alternatively to, the nitrogen atom-based linking cluster(s) of the triazole-based parent chain. Generally, the linking clusters disclosed herein are Lewis bases, and therefore have lone pair electrons available and/or can be deprotonated to form stronger Lewis bases. The deprotonated version of the linking clusters, therefore, are encompassed by the disclosure and anywhere a linking cluster that is depicted in a non-de-protonated form, the de-protonated form should be presumed to be included, unless stated otherwise. For example, although the structural Formulas presented herein are illustrated as having either an amine, for the purposes of this disclosure, these illustrated structures should be interpreted as including both the amine and the de-protonated amine.

The term "coordination number" refers to the number of atoms, groups of atoms, or linking clusters that bind to a central metal or metal ion where only the sigma bond between each atom, groups of atoms, or linking cluster and the central atom counts.

The term "coordination complex" refers to a central metal or a metal ion that is coordinated by one or more linking clusters of one or more linking moieties by forming coordinate bonds with the central metal or metal ion. For purposes of this disclosure a "coordination complex" includes complexes arising from linking moieties that have mono-dentate and/or polydentate linking clusters.

The term "alkyl," refers to an organic group that is comprised of carbon and hydrogen atoms that contains single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl," refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$ alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl," refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$ alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "cylcloalkyl," as used in this disclosure, refers to an alkyl that contains at least 3 carbon atoms but no more than 12 carbon atoms connected so that it forms a ring. A "cycloalkyl" for the purposes of this disclosure encompass from 1 to 7 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cylcloalkenyl," as used in this disclosure, refers to an alkene that contains at least 3 carbon atoms but no more than 12 carbon atoms connected so that it forms a ring. A "cycloalkenyl" for the purposes of this disclosure encompass from 1 to 7 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "aryl," as used in this disclosure, refers to a conjugated planar ring system with delocalized pi electron clouds that contain only carbon as ring atoms. An "aryl" for the purposes of this disclosure encompass from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "heterocycle," as used in this disclosure, refers to ring structures that contain at least 1 noncarbon ring atom. A "heterocycle" for the purposes of this disclosure encompass from 1 to 7 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "heterocyclyl" used alone or as a suffix or prefix, refers a monovalent radical derived from a heterocycle by removing a hydrogen therefrom. Heterocyclyl includes, for example, monocyclic heterocyclyls, such as, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydropyranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl. Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl. In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include, but are not limited to, quinuclidinyl, diazabicyclo[2.2.1]heptyl; and 7-oxabicyclo[2.2.1]heptyl.

The term "hetero-aryl" used alone or as a suffix or prefix, refers to a heterocycle or heterocyclyl having aromatic character. Examples of heteroaryls include, but are not limited to, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

The term "hetero-" when used as a prefix, such as, heteroalkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, Si(OH)$_3$, Ge(OH)$_3$, Sn(OH)$_3$, Si(SH)$_4$, Ge(SH)$_4$, Sn(SH)$_4$, AsO$_3$H, AsO$_4$H, P(SH)$_3$, and As(SH)$_3$.

As used herein, a "core" refers to a repeating unit or units found in a MET framework. Such a MET framework can comprise a homogenous repeating core, a heterogeneous repeating core or a combination of homogenous and heterogeneous cores. A core comprises a metal and/or metal ion or a cluster of metal and/or metal ions and a linking moiety.

The term "post framework reactants" refers to all known substances that are directly involved in a chemical reaction. Post framework reactants typically are substances, either elemental or MET frameworks, which have not reached the optimum number of electrons in their outer valence levels, and/or have not reached the most favorable energetic state due to ring strain, bond length, low bond dissociation energy, and the like. Some examples of post framework reactants include, but are not limited to:

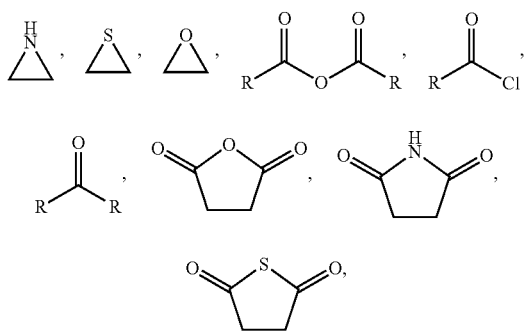

I—R, Br—R, CR$_3$—Mg—Br, CH$_2$R—Li, CR$_3$, Na—R, and K—R; and wherein each R is independently selected from the group comprising: H, sulfonates, tosylates, azides, triflates, ylides, alkyl, aryl, OH, alkoxy, alkenes, alkynes, phenyl and substitutions of the foregoing, sulfur-containing groups (e.g., thioalkoxy, thionyl chloride), silicon-containing groups, nitrogen-containing groups (e.g., amides and amines), oxygen-containing groups (e.g., ketones, carbonates, aldehydes, esters, ethers, and anhydrides), halogen, nitro, nitrile, nitrate, nitroso, amino, cyano, ureas, boron-containing groups (e.g., sodium borohydride, and catecholborane), phosphorus-containing groups (e.g., phosphorous tribromide), and aluminum-containing groups (e.g., lithium aluminum hydride).

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

A bond indicated by a straight line and a dashed line indicates a bond that may be a single covalent bond or alternatively a double covalent bond. But in the case where an atom's maximum valence would be exceeded by forming a double covalent bond, then the bond would be a single covalent bond.

MOFs, including the METs of the disclosure, are porous crystals whose structures are constructed from metal-containing cationic units and anionic organic links. Both components can be varied and functionalized for catalysis, and exceptional gas sorption, among many applications. There is a dearth of MOFs, however, with desirable porosity and stability that are not made from organic links of carboxylates, imidazolates, and tetrazolates. It has been problematic in the industry to develop new classes of MOFs from previously undeveloped metal-linker chemistry due to the tendency for the assembly reactions to yield microcrystalline powders rather than single crystalline products. The latter are highly sought after because of the ease with which crystals of complex MOFs can be solved by single crystal X-ray diffraction techniques. Although structure solution methods for powder X-ray diffraction data are used for solving the crystal structures of microcrystalline MOFs, these cases often require previous knowledge of the expected structure to achieve a satisfactory solution. Unfortunately, when no previous knowledge is available for the expected structure, as is frequently the case in new metal-linker MOF chemistry, a potentially interesting MOF goes uncharacterized because of the challenges associated with obtaining their structure from powder X-ray diffraction techniques. The disclosure demonstrates how the newly developed charge-flipping method is effective in solving the complex extended structures of metal triazolates (hereafter, METs). These MET frameworks are a new and novel class of porous crystals that exhibit electronic conductivity and permanent porosity. Their structures are not predictable due to the numerous ways in which the tridentate triazolate ligand can bind to the metal.

Not only can 1,2,3-triazole be an object of click-chemistry, but when you combine the ease with which it can be functionalized coupled with its rich metal complexation modes presents outstanding attributes for linking 1,2,3-triazole with metal ions in an extended framework. In particular, in contrast to imidazolates with four N atoms linked to the metal in tetrahedral coordination, triazoles with six N atoms per divalent metal would be expected to have six-fold (i.e. octahedral) coordination and a wider range of metals to form triazolates. The disclosure presents the successful synthesis, structure solution from X-ray powder diffraction and charge-flipping method, and porosity of a family of six METs of divalent metals Mg, Mn, Fe, Co, Cu and Zn. Moreover, the disclosure demonstrates that the metal ions form the same MET framework (MET-1 to 6), in which the metal ions are octahedrally coordinated to triazoles. Five metal centers are joined through six triply-bridging triazolates to form super-tetrahedral units which lie at the vertices of a diamond-type structure. The variation in the size of the metal ions across the series provides for precise control of pore apertures to a fraction of an Angstrom in the range 4.5 to 6.1 Å. The disclosure shows that the MET frameworks disclosed herein have permanent porosity and display surface areas as high as some of the most porous zeolites. In addition, the disclosure provides that a MET framework disclosed herein, MET-3, exhibits significant electrical conductivity.

The disclosure provides for the preparation of metal triazolate frameworks (METs). Scheme 1 presents a generalized scheme for forming one or more cores of the disclosure by coordinating one or more linking clusters of a linking moiety with metals or metal ions disclosed herein.

Scheme 1

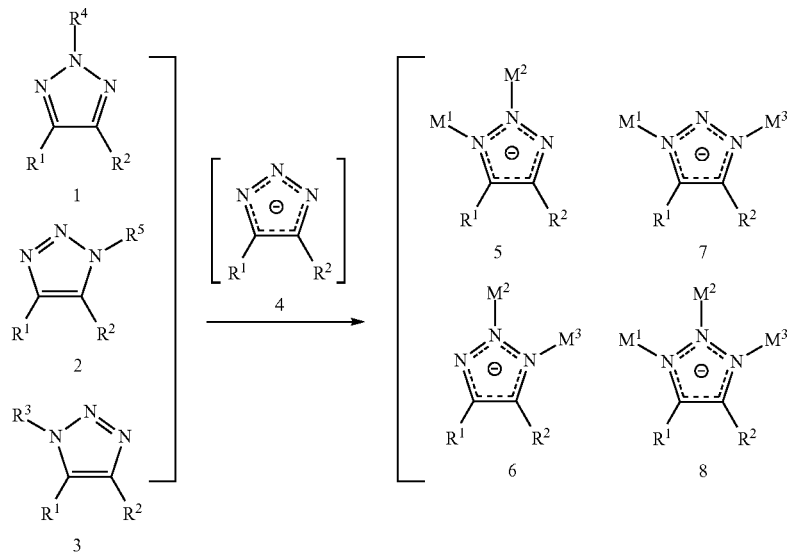

A 1,2,3-triazolate-based linking moiety (1, 2, or 3) deprotonates to form a triazolate intermediate anion 4, which then coordinates with $M^1$, $M^2$, and/or $M^3$ to form cores (5-8) of the disclosure.

In a certain embodiment, a MET framework disclosed herein comprises a network of homogenous metals or metal ions. In another embodiment, a MET framework of the disclosure comprises a network of homogenous metals or metal ions. In a further embodiment, a MET framework disclosed herein comprises cores wherein the linking moieties are homogenous. In a yet further embodiment, a MET framework of the disclosure comprises cores wherein the linking moieties are heterogeneous. In a certain embodiment, a MET framework disclosed herein comprises a network of homogenous metals or metal ions and linking moieties that are homogenous. In another embodiment, a MET framework disclosed herein comprises a network of homogenous metals or metal ions and linking moieties that are heterogeneous. In yet another embodiment, a MET framework of the disclosure comprises a network of heterogeneous metals or metal ions and linking moieties that are homogeneous. In another embodiment, a MET framework disclosed herein comprises a network of heterogeneous metals or metal ions and linking moieties that are heterogeneous.

In a certain embodiment, MET frameworks disclosed herein comprise one or more cores having Formula I:

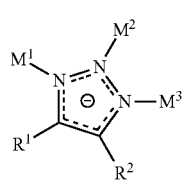

wherein,
$M^1$, $M^2$ and $M^3$ are independently selected metal or metals ions, and at least two of $M^1$, $M^2$ and $M^3$ are coordinated to nitrogens;

$R^1$ and $R^2$ are independently selected from the group comprising of H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, and wherein $R^1$ and $R^2$ are linked together to form a substituted or unsubstituted ring selected from the group comprising cycloalkyl, cycloalkenyl, heterocycle, aryl and mixed ring system.

In another embodiment, MET frameworks disclosed herein comprise one or more cores comprising structural Formula I:

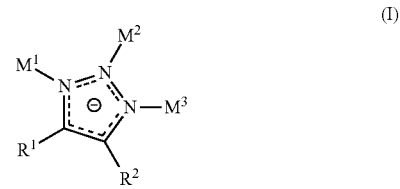

wherein,
$M^1$, $M^2$ and $M^3$ are independently selected metal or metals ions, and at least two of $M^1$, $M^2$ and $M^3$ are coordinated to nitrogens;

$R^1$-$R^2$ are independently selected from the group comprising H, optionally substituted FG, optionally substituted ($C_1$-$C_6$)alkyl, optionally substituted ($C_1$-$C_6$)alkenyl, optionally substituted ($C_1$-$C_6$)alkynyl, optionally substituted hetero-($C_1$-$C_6$)alkyl, optionally substituted hetero-($C_1$-$C_6$)alkenyl, optionally substituted hetero-($C_1$-$C_6$)alkynyl, optionally substituted cycloalkyl, optionally substituted cycloalkenyl, optionally substituted aryl, optionally substituted heterocycle, optionally substituted mixed ring system, —C($R^7$)$_3$, —CH($R^7$)$_2$, —CH$_2$$R^7$, —C($R^8$)$_3$, —CH($R^8$)$_2$, —CH$_2$$R^8$, —OC($R^7$)$_3$, —OCH($R^7$)$_2$, —OCH$_2$$R^7$, —OC($R^8$)$_3$, —OCH($R^8$)$_2$, —OCH$_2$$R^8$,

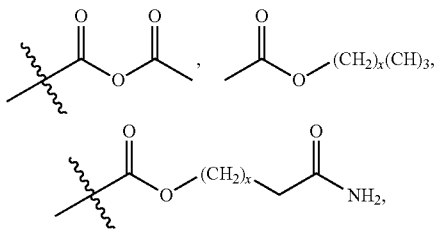

and wherein $R^1$ and $R^2$ are linked together to form a substituted or unsubstituted ring selected from the group comprising cycloalkyl, cycloalkenyl, heterocycle, aryl and mixed ring system;

$R^7$ is selected from the group comprising halo, hydroxyl, amine, thiol, cyano, carboxyl, optionally substituted ($C_1$-$C_6$)alkyl, optionally substituted ($C_1$-$C_6$)alkenyl, optionally substituted ($C_1$-$C_6$)alkynyl, optionally substituted hetero-($C_1$-$C_6$)alkyl, optionally substituted hetero-($C_1$-$C_6$)alkenyl, hemiacetal, hemiketal, acetal, ketal, and orthoester;

$R^8$ is one or more substituted or unsubstituted rings selected from the group comprising cycloalkyl, cycloalkenyl, aryl, heterocycle, and mixed ring system; and X is a number from 0 to 3.

In a further embodiment, MET frameworks disclosed herein comprise one or more cores of structural Formula I:

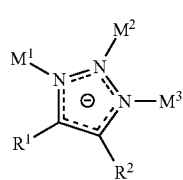

(I)

wherein, $M^1$, $M^2$ and $M^3$ are metals ions selected from the group comprising $Mg^{2+}$, $Mn^{2+}$, $Fe^{2+}$, $Co^{2+}$, $Zn^{2+}$, and $Cd^{2+}$, and at least two of $M^1$, $M^2$ and $M^3$ are coordinated to nitrogens; and $R^1$-$R^2$ are H.

Metals and their associated ions that can be used in the synthesis of MET frameworks disclosed herein are selected from the group comprising alkali metals, alkaline earth metals, transition metals, lanthanides, actinoids, metalloids, and post transition metals. Metal and/or metal ions can be introduced into open MET frameworks of the disclosure, via forming complexes with one or more linking clusters in a framework or by simple ion exchange. Therefore, it is reasonable to assume that any metal and/or metal ion disclosed herein can be introduced. Moreover, post synthesis of a MET framework of the disclosure, metal and/or metal ions may be exchanged by commonly known techniques, and/or additional metal ions can be added to a MET framework disclosed herein by forming coordination complexes with linking clusters arising from post framework reactants.

In an embodiment, one or more metals and/or metal ions that can be used in the (1) synthesis of a MET framework of the disclosure, (2) exchanged post synthesis of a MET framework disclosed herein, and/or (3) added to a MET framework of the disclosure by forming coordination complexes with one or more post framework reactant linking clusters, including, but are not limited to, alkali metals, alkaline earth metals, transition metals, lanthanides, actinoids, metalloids, and post transition metals.

In a certain embodiment, one or more metals and/or metal ions that can be used in the (1) synthesis of a MET framework of the disclosure, (2) exchanged post synthesis of a MET framework disclosed herein, and/or (3) added to a MET framework of the disclosure by forming coordination complexes with post framework reactant linking clusters, include, but are not limited to, $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, and $Lu^{3+}$, and any combination thereof, along with corresponding metal salt counter-anions.

In a further embodiment, one or more metal and/or metal ions that can be used in the (1) synthesis of a MET framework of the disclosure, (2) exchanged post synthesis of a MET framework disclosed herein, and/or (3) added to a MET framework of the disclosure by forming coordination complexes with post framework reactant linking clusters, include, but are not limited to, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{2+}$, $Zr^{4+}$, $Zr^{3+}$, $Zr^{2+}$, $Hg^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^+$, $Ga^{3+}$, $Ga^{2+}$, $Ga^+$, $In^{3+}$, $In^{2+}$, $In^{1+}$, and combinations thereof, along with corresponding metal salt counter-anions.

In yet a further embodiment, one or more metal ions that can be used in the (1) synthesis of a MET framework of the disclosure, (2) exchanged post synthesis of a MET framework disclosed herein, and/or (3) added to a MET framework of the disclosure by forming coordination complexes with post framework reactant linking clusters, include, but are not limited to, $Mg^{2+}$, $V^{5+}$, $V^{4+}$, $V^{3+}$, $V^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Fe^{6+}$, $Fe^{4+}$, $Fe^{3+}$, $Fe^{2+}$, $Fe^+$, Fe, $Co^{5+}$, $Co^{4+}$, $Co^{3+}$, $Co^{2+}$, $Co^+$, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Zn^{2+}$, $Zn^+$, Zn, $Cd^{2+}$, $Cd^+$, and any combination thereof, along with corresponding metal salt counter-anions.

In a certain embodiment, one or more metal ions used in the (1) synthesis of a MET framework of the disclosure, (2)

exchanged post synthesis of a MET framework disclosed herein, and/or (3) added to a MET framework of the disclosure by forming coordination complexes with post framework reactant linking clusters, include, but are not limited to, $Mg^{2+}$, $Mn^{3+}$, $Mn^{2+}$, $Mn^+$, $Fe^{3+}$, $Fe^{2+}$, $Fe^+$, $Co^{3+}$, $Co^{2+}$, $Co^+$, $Zn^{2+}$, $Zn^+$, $Cd^{2+}$, and $Cd^+$.

In a further embodiment, one or more metal ions in the (1) synthesis of a MET framework of the disclosure, (2) exchanged post synthesis of a MET framework disclosed herein, and/or (3) added to a MET framework of the disclosure by forming coordination complexes with post framework reactant linking clusters, are divalent metal ions.

In another embodiment, one or more metal ions in (1) synthesis of a MET framework of the disclosure, (2) exchanged post synthesis of a MET framework disclosed herein, and/or (3) added to a MET framework of the disclosure by forming coordination complexes with post framework reactant linking clusters, is a divalent metal ion selected from the group comprising $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $B^{2+}$, $Al^{2+}$, $Ga^{2+}$, $Si^{2+}$, $Sn^{2+}$, $Pb^{2+}$, $Hg^{2+}$, $As^{2+}$, $Te^{2+}$, $La^{2+}$, $Ce^{2+}$, $Pr^{2+}$, $Sm^{2+}$, $Gd^{2+}$, $Nd^{2+}$, $Db^{2+}$, $Tb^{2+}$, $Tm^{2+}$ and $Yb^{2+}$.

In another embodiment, one or more metal ions in (1) synthesis of a MET framework of the disclosure, (2) exchanged post synthesis of a MET framework disclosed herein, and/or (3) added to a MET framework of the disclosure by forming coordination complexes with post framework reactant linking clusters, is a divalent metal ion selected from the group comprising $Mg^{2+}$, $Mn^{2+}$, $Fe^{2+}$, $Co^{2+}$, $Zn^{2+}$, and $Cd^{2+}$.

In a further embodiment, the metal ion used in the synthesis of a metal organic framework of the disclosure is a divalent metal ion selected from the group comprising $Be^{2+}$, $Mg^{2+}$, $Ca^{2+}$, $Sr^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $B^{2+}$, $Al^{2+}$, $Ga^{2+}$, $Si^{2+}$, $Sn^{2+}$, $Pb^{2+}$, $Hg^{2+}$, $As^{2+}$, $Te^{2+}$, $La^{2+}$, $Ce^{2+}$, $Pr^{2+}$, $Sm^{2+}$, $Gd^{2+}$, $Nd^{2+}$, $Db^{2+}$, $Tb^{2+}$, $Tm^{2+}$ and $Yb^{2+}$.

In yet a further embodiment, the metal ion used in the synthesis of a metal organic framework disclosed herein is a divalent metal ion selected from the group comprising $Be^{2+}$, $Mg^+$, $Ca^{2+}$, $Sr^{2+}$, $Ba^{2+}$, $Sc^{2+}$, $Mn^{2+}$, $Fe^{2+}$, $Ni^{2+}$, $Pd^{2+}$, $Pt^{2+}$, $Cu^{2+}$, $Ag^{2+}$, $Hg^{2+}$, $Pb^{2+}$, $Zn^{2+}$, and $Cd^{2+}$.

In a certain embodiment, the metal ion used in the synthesis of a metal organic framework of the disclosure is a metal ion selected from the group comprising $Mg^{2+}$, $Mn^{2+}$, $Fe^{2+}$, $Co^{2+}$, $Zn^{2+}$, and $Cd^{2+}$.

Linking moiety linking clusters and/or post frameworks reactant linking clusters can be selected based on Hard Soft Acid Base theory (HSAB) to optimize the interaction between the linking clusters and/or post framework reactants and a metal or metal ion disclosed herein. In certain cases linking clusters and/or metal or metal ions are selected to be a hard acid and hard base, wherein linking clusters, post frameworks reactants, and/or metals or metal ions will have the following characteristics: small atomic/ionic radius, high oxidation state, low polarizability, hard electronegativity (bases), highest-occupied molecular orbitals (HOMO) of the hard base is low in energy, and lowest unoccupied molecular orbitals (LUMO) of the hard acid are of high energy. Generally hard base linking clusters contain oxygen. Typical hard metal and metal ions include alkali metals, and transition metals such as Fe, Cr, and V in higher oxidation states. In other cases linking clusters and/or metal or metal ions are selected to be a soft acid and a soft base, wherein linking clusters and/or metal or metal ions will have the following characteristics: large atomic/ionic radius, low or zero oxidation state, high polarizability, low electronegativity, soft bases have HOMO of higher energy than hard bases, and soft acids have LUMO of lower energy than hard acids. Generally soft base linking clusters contain sulfur, phosphorous, and larger halides. In other cases linking clusters and/or metal or metal ions are selected to be a borderline acid and a borderline base. In certain cases, linking clusters and/or metal or metal ions are selected so that they are hard and soft, hard and borderline, or borderline and soft.

In one embodiment, one or more metal ions in the (1) synthesis of a MET framework of the disclosure, (2) exchanged post synthesis of a MET framework disclosed herein, and/or (3) added to a MET framework of the disclosure by forming coordination complexes with post framework reactant linking clusters, and/or metal or metal ions, are HSAB hard metal and/or metal ions. In another embodiment, one or more metal ions in the (1) synthesis of a MET framework of the disclosure, (2) exchanged post synthesis of a MET framework disclosed herein, and/or (3) added to a MET framework of the disclosure by forming coordination complexes with post framework reactant linking clusters, are HSAB soft metal and/or metal ions. In yet another embodiment, one or more metal ions in the (1) synthesis of a MET framework of the disclosure, (2) exchanged post synthesis of a MET framework disclosed herein, and/or (3) added to a MET framework of the disclosure by forming coordination complexes with post framework reactant linking clusters, are HSAB borderline metal and/or metal ions. In the case that there is a plurality of metal and/or metal ions used in the (1) synthesis of a MET framework of the disclosure, (2) exchanged post synthesis of a MET framework disclosed herein, and/or (3) added to a MET framework of the disclosure by forming coordination complexes with post framework reactant linking clusters, then there can be any combination of hard, soft and borderline metals and/or metal ions that can be used in or attached to a MET framework disclose herein.

In a further embodiment, one or more metal ions in the (1) synthesis of a MET framework of the disclosure, (2) exchanged post synthesis of a MET framework disclosed herein, and/or (3) added to a MET framework of the disclosure by forming coordination complexes with post framework reactant linking clusters, have a coordination number selected from the following: 2, 4, 6, and 8. In another embodiment, one or more metal ions in the (1) synthesis of a MET framework of the disclosure, (2) exchanged post synthesis of a MET framework disclosed herein, and/or (3) added to a MET framework of the disclosure by forming coordination complexes with post framework reactant linking clusters, have a coordination number of either 4 or 6. In yet another embodiment, one or more metal ions in the (1) synthesis of a MET framework of the disclosure, (2) exchanged post synthesis of a MET framework disclosed herein, and/or (3) added to a MET framework of the disclosure by forming coordination complexes with post framework reactant linking clusters, have a coordination number of 6.

In a further embodiment, one or more metal and/or metal ions used in the synthesis of a MET framework disclosed herein can be coordinated with one or more linking clusters so that the coordination complex has a molecular geometry including, but not limited to, trigonal planar, tetrahedral, square planar, trigonal bipyramidal, square pyramidal, octahedral, trigonal prismatic, pentagonal bipyramidal, paddlewheel and square antiprismatic. In a further embodiment, a metal or metal ion used in the synthesis of a MET framework disclosed herein can form a coordination complex that has a molecular geometry including, but not limited to, tetrahedral, paddle-wheel and octahedral molecular geometry. In a further embodiment, a metal and/or metal ion used in the synthesis of a MET disclosed herein can form a coordination complex that has octahedral molecular geometry. In another embodiment, a coordination complex with octahedral geometry can exist as various isomers depending on whether two or more types of linking clusters are coordinated to a metal ion. Examples of such isomers that can result, include, but are not limited to, cis, trans, fac, mer, and any combination thereof for coordination complexes that have three or more different linking clusters. In a yet further embodiment, a coordination complex disclosed herein may have chirality. In another embodiment, a coordination complex disclosed herein may not have chirality.

In a certain embodiment, a MET framework of the disclosure comprises one or more cores comprising one or more linking moieties of structural Formula II:

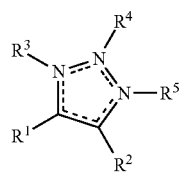

(II)

wherein:

$R^1$-$R^2$ are independently selected from the group comprising H, optionally substituted FG, optionally substituted ($C_1$-$C_6$)alkyl, optionally substituted ($C_1$-$C_6$)alkenyl, optionally substituted ($C_1$-$C_6$)alkynyl, optionally substituted hetero-($C_1$-$C_6$)alkyl, optionally substituted hetero-($C_1$-$C_6$)alkenyl, optionally substituted hetero-($C_1$-$C_6$)alkynyl, optionally substituted cycloalkyl, optionally substituted cycloalkenyl, optionally substituted aryl, optionally substituted heterocycle, optionally substituted mixed ring system, —C($R^7$)$_3$, —CH($R^7$)$_2$, —CH$_2R^7$, —C($R^8$)$_3$, —CH($R^8$)$_2$, —CH$_2R^8$, —OC($R^7$)$_3$, —OCH($R^7$)$_2$, —OCH$_2R^7$, —OC($R^8$)$_3$, —OCH($R^8$)$_2$, —OCH$_2R^8$,

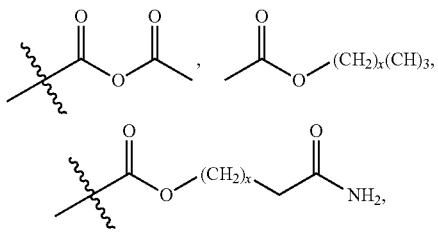

wherein $R^1$ and $R^2$ are linked together to form a substituted or unsubstituted ring selected from the group comprising cycloalkyl, cycloalkenyl, aryl, heterocycle, and mixed ring system;

$R^3$-$R^5$ are independently H, D or are absent when bound to a N atom that is doubly bonded to another atom;

$R^7$ is selected from the group comprising halo, hydroxyl, amine, thiol, cyano, carboxyl, optionally substituted ($C_1$-$C_6$) alkyl, optionally substituted ($C_1$-$C_6$)alkenyl, optionally substituted ($C_1$-$C_6$)alkynyl, optionally substituted hetero-($C_1$-$C_6$)alkyl, optionally substituted hetero-($C_1$-$C_6$)alkenyl, optionally substituted hetero-($C_1$-$C_6$)alkynyl, hemiacetal, hemiketal, acetal, ketal, and orthoester;

$R^8$ is one or more substituted or unsubstituted rings selected from the group comprising cycloalkyl, cycloalkenyl, aryl, heterocycle, and mixed ring system; and X is a number from 0 to 3.

In another embodiment, a MET framework of the disclosure comprises one or more cores comprising one or more linking moieties of structural Formula II:

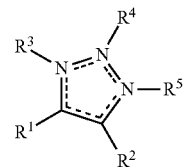

(II)

wherein:

$R^1$-$R^2$ are independently selected from the group comprising H, halo, amine, cyano, hydroxyl, aldehyde, $CO_2H$, $NO_2$, $SO_3H$, $PO_3H$, optionally substituted ($C_1$-$C_4$)alkyl, optionally substituted ($C_1$-$C_4$)ketone, optionally substituted ($C_1$-$C_4$)ester, optionally substituted ($C_1$-$C_4$)alkenyl, optionally substituted ($C_2$-$C_4$)alkynyl, optionally substituted hetero-($C_1$-$C_4$) alkyl, optionally substituted hetero-($C_1$-$C_4$)alkenyl, optionally substituted hetero-($C_2$-$C_4$)alkynyl, optionally substituted cycloalkyl, optionally substituted cycloalkenyl, optionally substituted aryl, optionally substituted heterocycle, optionally substituted mixed ring systems, —C($R^7$)$_3$, —CH($R^7$)$_2$, —CH$_2R^7$, —OC($R^7$)$_3$, —OCH($R^7$)$_2$, —OCH$_2R^7$,

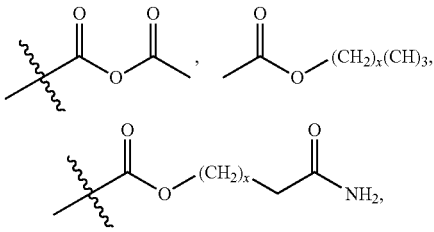

and wherein $R^1$ and $R^2$ are linked together to form a substituted or unsubstituted ring selected from the group comprising cycloalkyl, cycloalkenyl, aryl, heterocycle, and mixed ring system;

$R^3$-$R^5$ are independently H, D or are absent when bound to a N atom that is doubly bonded to another atom;

$R^7$ is selected from the group comprising halo, hydroxyl, amine, thiol, cyano, carboxyl, optionally substituted ($C_1$-$C_4$) alkyl, optionally substituted ($C_1$-$C_4$)alkenyl, optionally substituted ($C_1$-$C_4$)alkynyl, optionally substituted hetero-($C_1$-$C_4$)alkyl, optionally substituted hetero-($C_1$-$C_4$)alkenyl, and optionally substituted hetero-($C_1$-$C_4$)alkynyl; and X is a number from 0 to 2.

In yet another embodiment, a MET framework of the disclosure comprises one or more cores comprising one or more linking moieties of structural Formula II:

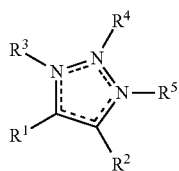

(II)

wherein:

R¹-R² are independently selected from the group comprising H, halo, amine, cyano, $CO_2H$, $NO_2$, $SO_3H$, $PO_3H$, optionally substituted ($C_1$-$C_4$)alkyl, optionally substituted ($C_1$-$C_4$)alkenyl, optionally substituted ($C_2$-$C_4$)alkynyl, optionally substituted hetero-($C_1$-$C_4$)alkyl, optionally substituted hetero-($C_1$-$C_4$)alkenyl, and optionally substituted hetero-($C_2$-$C_4$)alkynyl; and R³-R⁵ are independently H, D or are absent when bound to a N atom that is doubly bonded to another atom.

In a further embodiment, a MET framework disclosed herein comprises one or more cores comprising one or more linking moieties of structural Formula II:

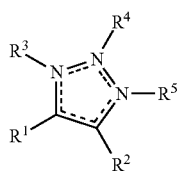

(II)

wherein:

R¹-R² are independently either a non-sterically hindering electron donating groups or H; and R³-R⁵ are independently H, D or are absent when bound to a N atom that is doubly bonded to another atom.

In a yet further embodiment, a MET framework of the disclosure comprises one or more core units comprising one or more linking moieties of structural Formula II:

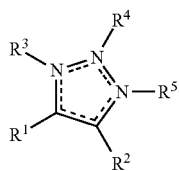

(II)

wherein:

R¹-R² are independently selected so as to interact with a particular gas or substrate, modulate pore size, or a combination thereof; and R³-R⁵ are independently H, D or are absent when bound to a N atom that is doubly bonded to another atom.

In a certain embodiment, a MET framework comprises one or more core units comprising one or more linking moieties selected from the group comprising: 2H-[1,2,3]triazole; 1H-[1,2,3]triazole; 4-chloro-2H-[1,2,3]triazole; 4-chloro-1H-[1,2,3]triazole; 4,5-dichloro-2H-[1,2,3]triazole; 4,5-dichloro-1H-[1,2,3]triazole; 4-bromo-2H-[1,2,3]triazole; 4-bromo-1H-[1,2,3]triazole; 4,5-dibromo-2H-[1,2,3]triazole; 4,5-dibromo-1H-[1,2,3]triazole; 4-fluoro-2H-[1,2,3]triazole; 4-fluoro-1H-[1,2,3]triazole; 4,5-difluoro-2H-[1,2,3]triazole; 4,5-difluoro-1H-[1,2,3]triazole; 4-iodo-2H-[1,2,3]triazole; 4-iodo-1H-[1,2,3]triazole; 4,5-diiodo-2H-[1,2,3]triazole; 4,5-diiodo-1H-[1,2,3]triazole; 5-trifluoromethyl-2H-[1,2,3]triazole; 5-trifluoromethyl-1H-[1,2,3]triazole; 4,5-bis-trifluoromethyl-2H-[1,2,3]triazole; 4,5-bis-trifluoromethyl-1H-[1,2,3]triazole; 2H-[1,2,3]triazole-4-ol; 1H-[1,2,3]triazole-4-ol; 2H-[1,2,3]triazole-4,5-diol; 1H-[1,2,3]triazole-4,5-diol; 2H-[1,2,3]triazole-4-carbonitrile; 1H-[1,2,3]triazole-4-carbonitrile; 2H-[1,2,3]triazole-4,5-dicarbonitrile; 1H-[1,2,3]triazole-4,5-dicarbonitrile; 2H-[1,2,3]triazole-4-ylamine; 1H-[1,2,3]triazole-4-ylamine; 2H-[1,2,3]triazole-4,5-diamine; 1H-[1,2,3]triazole-4,5-diamine; 4-methyl-2H-[1,2,3]triazole; 4-methyl-1H-[1,2,3]triazole; 4-ethyl-2H-[1,2,3]triazole; 4-ethyl-1H-[1,2,3]triazole; 4-propyl-2H-[1,2,3]triazole; 4-propyl-1H-[1,2,3]triazole; 4-butyl-2H-[1,2,3]triazole; 4-butyl-1H-[1,2,3]triazole; 4-isopropyl-2H-[1,2,3]triazole; 4-isopropyl-1H-[1,2,3]triazole; 4,5-diisopropyl-2H-[1,2,3]triazole; 4,5-diisopropyl-1H-[1,2,3]triazole; 4-tert-butyl-2H-[1,2,3]triazole; 4-tert-butyl-1H-[1,2,3]triazole; 4,5-di-tert-butyl-2H-[1,2,3]triazole; 4,5-di-tert-butyl-1H-[1,2,3]triazole; 2H-[1,2,3]triazole-4-carboxylic acid; 1H-[1,2,3]triazole-4-carboxylic acid; 2H-[1,2,3]triazole-4,5-dicarboxylic acid; 1H-[1,2,3]triazole-4,5-dicarboxylic acid; 2H-[1,2,3]triazole-4-carbaldehyde; 1H-[1,2,3]triazole-4-carbaldehyde; 2H-[1,2,3]triazole-4,5-dicarbaldehyde; 1H-[1,2,3]triazole-4,5-dicarbaldehyde; 1-(2H-[1,2,3]triazole-4-yl)-ethanone; 1-(1H-[1,2,3]triazole-4-yl)-ethanone; 1-(5-acetyl-2H-[1,2,3]triazole-4-yl)-ethanone; 1-(5-acetyl-1H-[1,2,3]triazole-4-yl)-ethanone; 2H-[1,2,3]triazole-4-thiol; 1H-[1,2,3]triazole-4-thiol; 2H-[1,2,3]triazole-4,5-dithiol; 1H-[1,2,3]triazole-4,5-dithiol; 5-mercaptomethyl-2H-[1,2,3]triazole-4-thiol; 5-mercaptomethyl-1H-[1,2,3]triazole-4-thiol; (5-mercaptomethyl-2H-[1,2,3]triazole-4-yl)-methanethiol; (5-mercaptomethyl-1H-[1,2,3]triazole-4-yl)-methanethiol; 4-nitro-2H-[1,2,3]triazole; 4-nitro-1H-[1,2,3]triazole; 4,5-dinitro-2H-[1,2,3]triazole; 4,5-dinitro-1H-[1,2,3]triazole; 4-vinyl-2H-[1,2,3]triazole; 4-vinyl-1H-[1,2,3]triazole; 4,5-divinyl-2H-[1,2,3]triazole; 4,5-divinyl-1H-[1,2,3]triazole; 2H-[1,2,3]triazolo[4,5-c]pyridine; 3H-[1,2,3]triazolo[4,5-c]pyridine; 2H-[1,2,3]triazolo[4,5-b]pyridine; 3H-[1,2,3]triazolo[4,5-b]pyridine; 2H-[1,2,3]triazolo[4,5-c]pyrimidine; 3H-[1,2,3]triazolo[4,5-d]pyrimidine; 2H-[1,2,3]triazolo[4,5-b]pyrazine; 3H-[1,2,3]triazolo[4,5-b]pyrazine; dimethyl-(2H-[1,2,3]triazol-4-yl)-amine; dimethyl-(1H-[1,2,3]triazol-4-yl)-amine; N,N,N',N'-tetramethyl-2H-[1,2,3]triazol-4,5-diamine; and N,N,N',N'-tetramethyl-1H-[1,2,3]triazol-4,5-diamine.

The preparation of MET frameworks of the disclosure can be carried out in either an aqueous or non-aqueous solvent system. The solvent may be polar or non-polar, or a combination thereof, as the case may be. The reaction mixture or suspension comprises a solvent system, linking moiety or moieties, and a metal or a metal/salt complex. The reaction solution, mixture or suspension may further contain a templating agent, catalyst, or combination thereof. The reaction mixture may be heated at an elevated temperature or maintained at ambient temperature, depending on the reaction components.

Examples of non-aqueous solvents that can be used in a reaction to make a MET framework disclosed herein and/or used as non-aqueous solvent for a post-synthesized MET framework reaction, include, but are not limited to: n-hydrocarbon based solvents, such as pentane, hexane, octadecane, and dodecane; branched and cyclo-hydrocarbon based solvents, such as cycloheptane, cyclohexane, methyl cyclohexane, cyclohexene, cyclopentane; aryl and substituted aryl based solvents, such as benzene, toluene, xylene, chlorobenzene, nitrobenzene, cyanobenzene, naphthalene, and aniline; mixed hydrocarbon and aryl based solvents, such as, mixed hexanes, mixed pentanes, naptha, and petroleum ether; alcohol based solvents, such as, methanol, ethanol, n-propanol, isopropanol, propylene glycol, 1,3-propanediol, n-butanol, isobutanol, 2-methyl-1-butanol, tert-butanol, 1,4-butanediol, 2-methyl-1-petanol, and 2-pentanol; amide based solvents, such as, dimethylacetamide, dimethylformamide (DMF), formamide, N-methylformamide, N-methylpyrrolidone, and 2-pyrrolidone; amine based solvents, such as, piperidine, pyrrolidine, collidine, pyridine, morpholine, quinoline, ethanolamine, ethylenediamine, and diethylenetriamine; ester based solvents, such as, butylacetate, sec-butyl acetate, tert-butyl acetate, diethyl carbonate, ethyl acetate, ethyl acetoacetate, ethyl lactate, ethylene carbonate, hexyl acetate, isobutyl acetate, isopropyl acetate, methyl acetate, propyl acetate, and propylene carbonate; ether based solvents, such as, di-tert-butyl ether, diethyl ether, diglyme, diisopropyl ether, 1,4-dioxane, 2-methyltetrahydrofuran, tetrahydrofuran (THF), and tetrahydropyran; glycol ether based solvents, such as, 2-butoxyethanol, dimethoxyethane, 2-ethoxyethanol, 2-(2-ethoxyethoxy)ethanol, and 2-methoxyethanol; halogenated based solvents, such as, carbon tetrachloride, cholorbenzene, chloroform, 1,1-dichloroethane, 1,2-dichloroethane, 1,2-dichloroethene, dichloromethane (DCM), diiodomethane, epichlorohydrin, hexachlorobutadiene, hexafluoro-2-propanol, perfluorodecalin, perfluorohexane, tetrabromomethane, 1,1,2,2-tetrchloroethane, tetrachloroethylene, 1,3,5-trichlorobenzene, 1,1,1-trichloroethane, 1,1,2-trichloroethane, trichloroethylene, 1,2,3-trichloropropane, trifluoroacetic acid, and 2,2,2-trifluoroethanol; inorganic based solvents, such as hydrogen chloride, ammonia, carbon disulfide, thionyl chloride, and phosphorous tribromide; ketone based solvents, such as, acetone, butanone, ethylisopropyl ketone, isophorone, methyl isobutyl ketone, methyl isopropyl ketone, and 3-pentanone; nitro and nitrile based solvents, such as, nitroethane, acetonitrile, and nitromethane; sulfur based solvents, dimethyl sulfoxide (DMSO), methylsulfonylmethane, sulfolane, isocyanomethane, thiophene, and thiodiglycol; urea, lactone and carbonate based solvents, such as 1-3-dimethyl-3,4,5,6-tetrahydro-2(1H)-pyrimidinone (DMPU), 1-3-dimethyl-2-imidazolidinone, butyrolactone, cis-2,3-butylene carbonate, trans-2,3-butylene carbonate, 2,3-butylene carbonate; carboxylic acid based solvents, such as formic acid, acetic acid, chloracetic acid, trichloroacetic acid, trifluoroacetic acid, propanoic acid, butanoic acid, caproic acid, oxalic acid, and benzoic acid; boron and phosphorous based solvents, such as triethyl borate, triethyl phosphate, trimethyl borate, and trimethyl phosphate; deuterium containing solvents, such as deuterated acetone, deuterated benzene, deuterated chloroform, deuterated dichloromethane, deuterated DMF, deuterated DMSO, deuterated ethanol, deuterated methanol, and deuterated THF; and any appropriate mixtures thereof.

In another embodiment, a nonaqueous solvent used as the solvent system in synthesizing a MET framework disclosed herein has a pH less than 7. In a further embodiment, a solvent system used to synthesize a MET framework of the disclosure is an aqueous solution that has a pH less than 7. In yet a further embodiment, a solvent system used to synthesize a MET framework disclosed herein contains DMF or N,N-diethylformamide. In another embodiment, a solvent system used to synthesize a MET framework of the disclosure contains a base.

Those skilled in the art will be readily able to determine an appropriate solvent or appropriate mixture of solvents based on the starting reactants and/or where the choice of a particular solvent(s) is not believed to be crucial in obtaining the materials of the disclosure.

Templating agents can be used in the methods of the disclosure. Templating agents employed in the disclosure are added to the reaction mixture for the purpose of occupying the pores in the resulting MET frameworks disclosed herein. In some variations of the disclosure, space-filling agents, absorbed or adsorbed chemical species and guest species increase the surface area of a MET framework disclosed herein. Suitable space-filling agents include, for example, a component selected from the group consisting of: (i) alkyl amines and their corresponding alkyl ammonium salts, containing linear, branched, or cyclic aliphatic groups, having from 1 to 20 carbon atoms; (ii) aryl amines and their corresponding aryl ammonium salts having from 1 to 5 phenyl rings; (iii) alkyl phosphonium salts, containing linear, branched, or cyclic aliphatic groups, having from 1 to 20 carbon atoms; (iv) aryl phosphonium salts, having from 1 to 5 phenyl rings; (v) alkyl organic acids and their corresponding salts, containing linear, branched, or cyclic aliphatic groups, having from 1 to 20 carbon atoms; (vi) aryl organic acids and their corresponding salts, having from 1 to 5 phenyl rings; (vii) aliphatic alcohols, containing linear, branched, or cyclic aliphatic groups, having from 1 to 20 carbon atoms; or (viii) aryl alcohols having from 1 to 5 phenyl rings.

In certain embodiments templating agents are used with the methods disclosed herein, and in other embodiments templating agents are not used with the methods disclosed herein.

Crystallization of MET frameworks of the disclosure can be carried out by maintaining the solution, mixture, or suspension at ambient temperature or by maintaining the solution, mixture, or suspension at an elevated temperature; adding a diluted base to the solution; diffusing the diluted base throughout the solution; and/or transferring the solution to a closed vessel and heating to a predetermined temperature.

In a certain embodiment, crystallization of MET frameworks of the disclosure can be improved by adding an additive that promotes nucleation.

In another embodiment, the solution, mixture or suspension is maintained at ambient temperature to allow for crystallization. In yet another embodiment, the solution, mixture, or suspension is heated at an elevated temperature to allow for crystallization. In a certain embodiment, the solution, mixture, or suspension is heated at an elevated temperature up to 200° C. to allow for crystallization. In a yet further embodiment, crystallization of the frameworks can be achieved by heating the frameworks at 100° C. to 130° C. for 1 to 72 hours. In a further embodiment, activated frameworks can be generated by calcination.

The MET frameworks of the disclosure may be generated by first utilizing a plurality of linking moieties having different functional groups, wherein at least one of these functional groups may be modified, substituted, or eliminated with a different functional group post-synthesis of the framework. In other words, at least one linking moiety comprises a functional group that may be post-synthesized reacted with a post framework reactant to further increase the diversity of the functional groups of MET frameworks disclosed herein.

After MET frameworks of the disclosure are synthesized, the MET frameworks may be further modified by reacting with one or more post framework reactants that may or may not have denticity. In a certain embodiment, the MET frameworks as-synthesized are not reacted with a post framework reactant. In another embodiment, the MET frameworks as-synthesized are reacted with at least one post framework reactant. In yet another embodiment, the MET frameworks as-synthesized are reacted with at least two post framework reactants. In a further embodiment, the MET frameworks as-synthesized are reacted with at least one post framework reactant that will result in adding denticity to the framework.

The disclosure provides for chemical reactions that modify, substitute, or eliminate a functional group post-synthesis of a MET framework disclosed herein with a post framework. These chemical reactions may use one or more similar or divergent chemical reaction mechanisms depending on the type of functional group and/or post framework reactant used in the reaction. Examples of chemical reaction include, but are not limited to, radical-based, unimolecular nuclephilic substitution (SN1), bimolecular nucleophilic substitution (SN2), unimolecular elimination (E1), bimolecular elimination (E2), E1cB elimination, nucleophilic aromatic substitution (SnAr), nucleophilic internal substitution (SNi), nucleophilic addition, electrophilic addition, oxidation, reduction, cycloaddition, ring closing metathesis (RCM), pericylic, electrocylic, rearrangement, carbene, carbenoid, cross coupling, and degradation.

All the aforementioned linking moieties that possess appropriate reactive functionalities can be chemically transformed by a suitable reactant post framework synthesis to add further functionalities to the pores. By modifying the organic links within the framework post-synthetically, access to functional groups that were previously inaccessible or accessible only through great difficulty and/or cost is possible and facile.

It is yet further contemplated by this disclosure that to enhance chemoselectivity it may be desirable to protect one or more functional groups that would generate unfavorable products upon a chemical reaction desired for another functional group, and then deprotect this protected group after the desired reaction is completed. Employing such a protection/deprotection strategy could be used for one or more functional groups.

Other agents can be added to increase the rate of the reactions disclosed herein, including adding catalysts, bases, and acids.

In another embodiment, a post framework reactant adds at least one effect to a metal-triazolate framework of the disclosure including, but not limited to, modulating the gas storage ability of a metal-triazolate framework; modulating the sorption properties of a metal-triazolate framework; modulating the pore size of a metal-triazolate framework; modulating the catalytic activity of a metal-triazolate framework; modulating the conductivity of a metal-triazolate; and modulating the sensitivity of a metal-triazolate framework to the presence of an analyte of interest. In a further embodiment, a post framework reactant adds at least two effects to a metal-triazolate framework of the disclosure including, but not limited to, modulating the gas storage ability of a metal-triazolate framework; modulating the sorption properties of a metal-triazolate framework; modulating the pore size of a metal-triazolate framework; modulating the catalytic activity of a metal-triazolate framework; modulating the conductivity of a metal-triazolate; and modulating the sensitivity of a metal-triazolate framework to the presence of an analyte of interest.

In one embodiment, a post framework reactant can be a saturated or unsaturated heterocycle.

In another embodiment, a post framework reactant has 1-20 carbons with functional groups including atoms such as N, S, and O.

In yet another embodiment, a post framework reactant is selected to modulate the size of the pores of a MET framework disclosed herein.

In another embodiment, a post framework reactant is selected to increase the hydrophobicity of a MET framework disclosed herein.

In yet another embodiment, a post framework reactant is selected to modulate gas separation of a MET framework disclosed herein. In a certain embodiment, a post framework reactant creates an electric dipole moment on the surface of a MET framework of the disclosure when it chelates a metal ion.

In a further embodiment, a post framework reactant is selected to modulate the gas sorption properties of a MET framework of the disclosure. In another embodiment, a post framework reactant is selected to promote or increase greenhouse gas sorption of a MET framework disclosed herein. In another embodiment, a post framework reactant is selected to promote or increase hydrocarbon gas sorption of a MET framework of the disclosure.

In yet a further embodiment, a post framework reactant is selected to increase or add catalytic efficiency to a MET framework disclosed herein.

In another embodiment, a post framework reactant is selected so that organometallic complexes can be tethered to a MET framework of the disclosure. Such tethered organometallic complexes can be used, for example, as heterogeneous catalysts.

Natural gas is an important fuel gas and it is used extensively as a basic raw material in the petrochemical industry and other chemical process industries. The composition of natural gas varies widely from field to field. Many natural gas reservoirs contain relatively low percentages of hydrocarbons (less than 40%, for example) and high percentages of acid gases, principally carbon dioxide, but also hydrogen sulfide, carbonyl sulfide, carbon disulfide and various mercaptans. Removing acid gases from natural gas recovered from remote national gas fields provides conditioned or sweet, dry natural gas either for delivery to pipelines, natural gas liquids recovery, helium recovery, conversion to liquefied natural gas (LNG), or for subsequent nitrogen rejection. Carbon dioxide is corrosive when in the presence of water. Carbon dioxide freezes to form dry ice under certain temperatures and pressures that can lead to freeze-up problems in pipelines and in cryogenic equipment which are used in processing natural gas. Also, by not contributing to the heating value, carbon dioxide merely adds to the cost of gas transmission.

Moreover, power plants produce a large amount of anthropogenic carbon dioxide as a byproduct of combustion. Removal of the carbon dioxide from the flue exhaust of power plants is commonly accomplished by chilling and pressurizing the exhaust or by passing the fumes through a fluidized bed of aqueous amine solution, both of which are costly and inefficient. Other methods based on chemisorption of carbon dioxide on oxide surfaces or adsorption within porous silicates, carbon, and membranes have been pursued as means for carbon dioxide uptake. However, in order for an effective adsorption medium to have long term viability in carbon dioxide removal it should combine two features: (i) a periodic structure for which carbon dioxide uptake and release is fully reversible, and (ii) a flexibility with which chemical functionalization and molecular level fine-tuning can be achieved for optimized uptake capacities.

A number of processes for the recovery or removal of carbon dioxide from gas steams have been proposed and practiced on a commercial scale. The processes vary widely, but generally involve some form of solvent absorption, adsorption on a porous adsorbent, distillation, or diffusion through a semipermeable membrane.

In one embodiment, a gas separation material comprising one or more MET frameworks disclosed herein is provided. Advantageously, a MET framework disclosed herein includes one or more sites for sorption of one or more select gas molecules resulting in separation of these gas molecules from a multicomponent gas. Furthermore, gases that may be separated by one or more MET frameworks disclosed herein include gas molecules comprising available electron density for attachment to the one or more sites on the surface area of a pore or interpenetrating porous network. Such electron density includes molecules having multiple bonds between two atoms contained therein or molecules having a lone pair of electrons. Suitable examples of such gases include, but are not limited to, the gases comprising a component selected from the group consisting of ammonia, argon, carbon dioxide, hydrogen sulfide, carbonyl sulfide, carbon disulfide, mercaptans, carbon monoxide, hydrogen, and combinations thereof. In one embodiment, one or more MET frameworks disclosed herein, can be used to separate one or more component gases from a multi-component gas mixture. In a certain embodiment, one or more MET frameworks disclosed herein can be used to separate one or more gases with high electron density from a gas mixture. In another embodiment, one or more MET frameworks disclosed herein can be used to separate one or more gases with high electron density from one or more gases with low electron density.

In one embodiment, one or more MET frameworks disclosed herein are part of a device. In one embodiment, a gas separation device comprises one or more MET frameworks of the disclosure. In a further embodiment, a gas separation device used to separate one or more component gases from a multi-component gas mixture comprises one or more MET frameworks disclosed herein. In a certain embodiment, a gas separation device used to separate one or more gases with high electron density from gas mixture comprises one or more MET frameworks of the disclosure. In a further embodiment, a gas separation device used to separate one or more gases with high electron density from one or more low density gases comprises one or more MET frameworks of the disclosure.

In one embodiment of the disclosure, a gas storage material comprising one more MET frameworks disclosed herein is provided. A gas that may be stored or separated by the methods, compositions and systems of the disclosure includes gas molecules comprising available electron density for attachment to the one or more sites. Such electron density includes molecules having multiple bonds between two atoms contained therein or molecules having a lone pair of electrons. Suitable examples of such gases include, but are not limited to, the gases comprising a component selected from the group consisting of ammonia, argon, hydrogen sulfide, carbon dioxide, hydrogen sulfide, carbonyl sulfide, carbon disulfide, mercaptans, carbon monoxide, hydrogen, and combinations thereof. In particularly useful variation, a gas binding material is a carbon dioxide binding material that may be used to separate carbon dioxide from a gaseous mixture. In a particularly useful variation a gas storage material is a hydrogen storage material that is used to store hydrogen ($H_2$). In another particularly useful variation, a gas storage material is a carbon dioxide storage material that may be used to separate carbon dioxide from a gaseous mixture.

In yet a further embodiment, one or more MET frameworks disclosed herein can be used to separate and/or store one or more gases selected from the group comprising carbon monoxide, carbon dioxide, hydrogen sulfide, carbonyl sulfide, carbon disulfide, mercaptans, nitrous oxide, and ozone.

In another embodiment, one or more MET frameworks disclosed herein can be used to separate and/or store one or more gases selected from the group comprising carbon monoxide, carbon dioxide, hydrogen sulfide, carbonyl sulfide, carbon disulfide, and mercaptans.

In yet another embodiment, one or more MET frameworks disclosed herein can be used to separate and/or store carbon monoxide or carbon dioxide.

In a certain embodiment, one or more MET frameworks disclosed herein can be used to separate and/or store carbon dioxide.

In one embodiment, one or more MET frameworks disclosed herein can be used to separate and/or store hydrogen.

In one embodiment, a gas storage device comprises one or more MET frameworks disclosed herein. In a further embodiment, a gas storage device used to adsorb and/or absorb one or more component gases from a multi-component gas mixture comprises one or more MET frameworks disclosed herein. In a certain embodiment, a gas storage device used to adsorb and/or absorb one or more gases with high electron density from gas mixture comprises one or more MET frameworks disclosed herein. In a further embodiment, a gas storage device used to adsorb and/or absorb one or more gases with high electron density from one or more low density gases comprises one or more MET frameworks disclosed herein.

The disclosure also provides methods using MET frameworks disclosed herein. In a certain embodiment, a method to separate or store one or more gases comprises contacting one or more gases with one or more MET frameworks disclosed herein. In a further embodiment, a method to separate or store one or more gases from a mixed gas mixture comprises contacting the gas mixture with one or more MET frameworks disclosed herein. In a yet further embodiment, a method to separate or store one or more high electron density gases from a mixed gas mixture comprises contacting the gas mixture with one or more MET frameworks disclosed herein. In a certain embodiment, a method to separate or store one or more gases from a fuel gas stream comprises contacting the fuel gas stream with one or more MET frameworks disclosed herein. In a further embodiment, a method to separate or store one or more acid gases from a natural gas stream comprises contacting the natural gas stream with one or more MET frameworks disclosed herein. In yet another embodiment, a method to separate or store one or more gases from the exhaust of a combustion engine comprises contacting the exhaust with one or more MET frameworks disclosed herein. In a certain embodiment, a method to separate or store one or more gases from flue-gas comprises contacting the flue-gas with one or more MET frameworks disclosed herein.

One or more MET frameworks of the disclosure can also comprise part of a gas separation and/or a gas storage device. These devices for gas separation and/or gas storage can be used for industrial or nonindustrial purposes, or a combination thereof. Examples of gas separation and/or gas storage devices include, but are not limited to, purifiers, filters, scrubbers, pressure swing adsorption devices, molecular sieves, hollow fiber membranes, ceramic membranes, cryogenic air separation devices, and hybrid gas separation devices. In one embodiment, gas separation and/or gas storage devices comprising one or more MET frameworks of the disclosure can be used to purify fuel gas streams, air, flue-gas emissions, and/or waste emissions from combustion engines. In another embodiment, one or more MET frameworks disclosed herein can comprise gas separation and/or gas storage devices designed to remove and/or store greenhouse gases, such as carbon dioxide, ozone, nitrous oxide, and fluorocarbons. In a certain embodiment, one or more MET frameworks disclosed herein can comprise gas separation and/or gas storage devices designed to remove and/or store environmental pollutants, such as formaldehyde, diisocyanates, trichloroethylene, and benzene.

In a certain embodiment, an air purification device comprises one or more MET frameworks disclosed herein. In a further embodiment, a device used to remove and/or store contaminants from fuel gas comprises one or more MET frameworks disclosed herein. In yet a further embodiment, a device used to remove and/or store environmentally harmful gases from flue gas emissions comprises one or more MET frameworks disclosed herein. In a certain embodiment, a device used to remove and/or store environmentally harmful gases or gaseous vapors from air comprises one or more MET frameworks disclosed herein. In a further embodiment, a device used to remove and/or store greenhouse gases comprises one or more MET frameworks disclosed herein. In a yet further embodiment, a device for use to prevent buildups of one or more hazardous gases in mining comprises one or more MET frameworks disclosed herein. In a yet further embodiment, a device for use to remove and/or store one or more gases from emissions of a combustion engine comprises one or more MET frameworks disclosed herein.

The disclosure provides an apparatus and method for separating one or more components from a multi-component gas using a separation system having a feed side and an effluent side separated by one or more MET frameworks of the disclosure. The MET framework may comprise a column separation format.

"Natural gas" refers to a multi-component gas obtained from a crude oil well (associated gas) or from a subterranean gas-bearing formation (non-associated gas). The composition and pressure of natural gas can vary significantly. A typical natural gas stream contains methane as a significant component. The natural gas will also typically contain ethane, higher molecular weight hydrocarbons, one or more acid gases (such as carbon dioxide, hydrogen sulfide, carbonyl sulfide, carbon disulfide, and mercaptans), and minor amounts of contaminants such as water, nitrogen, iron sulfide, wax, and crude oil.

The disclosure is particularly suitable for treatment of natural gas streams containing one or more contaminants such as carbon dioxide, hydrogen sulfide, and water vapor. The disclosure, however, is not limited to treatment of natural gas. One or more MET frameworks and methods disclosed herein can be used to separate a one or more gas components of a multi-component gas.

In a certain embodiment, one or more MET frameworks disclosed herein can be used to separate and/or store one or more gases from a natural gas stream. In another embodiment, one or more MET frameworks disclosed herein can be used to separate and/or store one or more acid gases from a natural gas stream. In yet another embodiment, one or more MET frameworks disclosed herein can be used to separate and/or store one or more gases from a town gas stream. In yet another embodiment, one or more MET frameworks disclosed herein can be used to separate and/or store one or more gases of a biogas stream. In yet another embodiment, one or more MET frameworks disclosed herein can be used to separate and/or store one or more gases from a syngas stream.

Sorption is a general term that refers to a process resulting in the association of atoms or molecules with a target material. Sorption includes both adsorption and absorption. Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase.

These materials would be used as standard MET frameworks for sorption instruments, and obtained results would be helpful to improve various industrial plants (i.e. separation or recovery of chemical substance).

In a variation of this embodiment, the gaseous storage site comprises a pore in a MET framework disclosed herein which is functionalized with a group having a desired size or charge. In a refinement, this activation involves removing one or more chemical moieties (guest molecules) from a MET framework of the disclosure. Typically, such guest molecules include species such as water, solvent molecules contained within a MET framework disclosed herein, and other chemical moieties having electron density available for attachment.

One or more MET frameworks used in the embodiments of the disclosure include a plurality of pores for gas adsorption. In one variation, the plurality of pores has a unimodal size distribution. In another variation, the plurality of pores have a multimodal (e.g., bimodal) size distribution.

The disclosure also provides chemical sensors (e.g. resistometric sensors) capable of sensing the presence of an analyte of interest. There is considerable interest in developing sensors that act as analogs of the mammalian olfactory system. However, many of such sensor systems are easily contaminated. The porous structures of the disclosure provide a defined interaction area that limits the ability of contaminate to contact a sensor material the passes through the porous structure of one or more MET frameworks of the disclosure. For example, various polymers are used in sensor systems including conductive polymers (e.g., poly(anilines) and polythiophenes), composites of conductive polymers and non-conductive polymers and composites of conductive materials and non-conductive materials. In resistometric systems conductive leads are separated by the conductive material such that a current traverse between the leads and through the sensor material. Upon binding to an analyte, the resistance in the material changes and detectable signal is thus generated. Using a MET framework of the disclosure, the area surrounding the sensor material is limited and serves as a "filter" to limit contaminants from contacting the sensor material, thus increasing sensor specificity.

In a certain embodiment, a carbon monoxide detector comprises one or more MET frameworks of the disclosure. In another embodiment, a combustible gas detector comprises one or more MET frameworks disclosed herein. In a further embodiment, a device used to measure vehicle emissions comprises one or more MET frameworks of the disclosure.

The disclosure further provides for MET framework catalysts comprising one or more MET frameworks of the disclosure. One or more MET frameworks of the disclosure, as crystalline material or as molding, can be used in the catalytic conversion of organic molecules. Reactions of this type are, for example, oxidations, the epoxidation of olefins, e.g. the preparation of propylene oxide from propylene and $H_2O_2$ the hydroxylation of aromatics, e.g. the preparation of hydroquinone from phenol and $H_2O_2$ or the conversion of toluene into cresol, the conversion of alkanes into alcohols, aldehydes and acids, isomerization, reactions, for example the conversion of epoxides into aldehydes.

The invention is illustrated in the following examples, which are provided by way of illustration and are not intended to be limiting.

EXAMPLES

A new family of porous crystals was prepared by combining 1,2,3-triazole and metal ions (Mg, Mn, Fe, Co, Cu, Zn, and Cd) to give seven isostructural metal-triazolates (termed MET-1 to 7). These materials were prepared as microcrystalline powders which gave intense X-ray diffraction lines. The charge-flipping method solved the METs' complex crystal structure: all the metal ions are octahedrally coordinated to the nitrogen atoms of triazolate such that five metal centers are joined through bridging triazolate ions to form supertetrahedral units which lie at the vertexes of a diamond-type structure. The variation in the size of metal ions across the series provides for precise control of pore apertures to a fraction of an Angstrom in the range 4.5 to 6.1 Å. MET frameworks have permanent porosity and display surface areas as high as some of the most porous zeolites, with one member of this family, MET-3, exhibiting significant electrical conductivity.

The disclosure demonstrates the synthesis, structure and porosity of a family of seven metal-triazolates (METs) frameworks in which the divalent metals Mg, Mn, Fe, Co, Cu, Zn, and Cd are linked with triazolate to make porous isostructural diamond-type frameworks (MET-1 to 7). The materials can be prepared by combining triazole-based linking moiety or derivative thereof with a salt of the metal, usually chloride or nitrate. In the case of MET-6, the product crystallizes at room temperature, with the adequate combination of solvents and the presence of a base (e.g., $NH_4OH$). For other materials, a heating period is used to optimize crystallization of the products.

Synthesis of MET-1:

(Mg): In a vial, $MgCl_2$ (4 mmol) was slowly dissolved in N,N-diethylformamide (DEF) (12 ml). After adding 1H-1,2,3-triazole (10 mmol), the vial was capped and placed in a preheated oven at 120° C. for 10 days. The resulting white solid was washed with DEF three times. The white solid was then immersed in methanol for 3 days, in which the solvent was changed 3 times during this time period. After the solvent was removed by decantation, the wet solid was dried under vacuum ($10^{-5}$ torr) at 100° C. for 24 hours to afford the title MET framework as a white powder, which was then stored in a desiccator. Yield: 20% based on $MgCl_2$. Elemental Analysis for Mg $(C_2H_2N_3)_2$. Calculated: C, 29.94%, N, 52.39%, H, 2.52, Mg, 15.16%. Measured: C x %, N x %, H x %. FT-IR: 2882 (w), 1621 (vs), 1453 (vw), 1408 (w), 1360 (vs), 1268 (m), 1186 (m), 1108 (s), 982 (m), 803 (s), 697 (w).

Synthesis of MET-2:

(Mn): In a vial, $Mn(NO_3)_2$ $4H_2O$ (1 mmol) was dissolved in DEF (10 ml). After adding 1H-1,2,3-triazole (2.5 mmol), the vial was capped and placed in a preheated oven at 120° C. for 10 days. The resulting white solid was washed with DEF three times. The white solid was then immersed in methanol for 3 days, in which the solvent was changed 3 times during this time period. After the solvent was removed by decantation, the wet solid was dried under vacuum ($10^{-5}$ torr) at ambient temperature for 24 hours to afford the titled MET framework as a white powder, which was then stored in a desiccator. Yield: 92% based on Mn $(NO_3)_2$. Elemental Analysis for $Mn(C_2H_2N_3)_2$. Calculated: C, 25.13%, N, 43.98%, H, 2.12%, Mn 28.77%. Measured: C, 24.95%, N, 41.89%, H, 2.05%. FT-IR: 3145 (m), 2938 (w), 2864 (w), 2656 (vw), 2515 (vw), 2414 (w), 2364 (w), 2195 (w), 1719 (w), 1650 (m), 1456 (m), 1416 (m), 1381 (w), 1178 (s), 1098 (vs), 974 (s), 798 (vs), 718 (w).

Synthesis of MET-3 (Fe):

The synthesis of MET-3 was carried out under an anhydrous atmosphere, using Schlenk line techniques. $FeCl_2$ (0.5 mmol) was weighted and placed in a Pyrex tube measuring 10×8 mm (o.d×i.d). The tube was evacuated and refilled with Ar three times, to ensure an anhydrous reaction conditions. Under an Ar atmosphere, anhydrous N,N-dimethylformamide (DMF) (3 ml) was then added to the tube. After $FeCl_2$ was completely dissolved in the DMF, 1H-1,2,3-triazole (1.5 mmol) was added to the solution. The tube was then flash frozen in liquid $N_2$, and then evacuated to a pressure ≤150 mtorr. The tube was flame sealed. Upon sealing, the length of the tube was reduced to 18-20 cm. The mixture was then heated at 120° C. for 48 hours. The resulting pink solid was collected by centrifugation and washed with DMF (15 ml) 3 times. The pink solid was then immersed in methanol for 3 days, in which the solvent was exchanged 3 times during this time period. The solvent was removed by decantation and the wet solid was dried under vacuum ($10^{-5}$ torr) at 100° C. for 24 hours to afford the titled MET framework as a pink powder, which was then stored in a desiccator. Yield: 70% based on $FeCl_2$ Analysis for $Fe(C_2H_2N_3)_2$. Calculated: C, 25.02%, N, 43.78%, H, 2.11%, Measured: C, 24.19%, N, 42.24%, H, 2.23%. FT-IR: 3142 (m), 2959 (w), 2919 (w), 2356 (m), 1678 m), 1475 (m), 1263 (m), 1229 (w), 1179 (s), 1125 (vs), 1003 (s), 787 (vs), 726 (w).

Synthesis of MET-4 (Co):

The synthesis of MET-4 was carried out under an anhydrous atmosphere, using Schlenk line techniques. $CoCl_2$ (0.5 mmol) was weighted and placed in a Pyrex tube measuring 10×8 mm (o.d×i.d). The tube was evacuated and refilled with Ar three times, to ensure an anhydrous reaction conditions. Under an Ar atmosphere, anhydrous DMF (3 ml) was then added to the tube. After $FeCl_2$ was completely dissolved in the DMF, 1H-1,2,3-triazole (1.5 mmol) was added to the solution. The tube was then flash frozen in liquid $N_2$, and then evacuated to a pressure ≤150 mtorr. The tube was flame sealed. Upon sealing, the length of the tube was reduced to 18-20 cm. The reaction was heated at 120° C. for 48 hours. The resulting yellow solid was collected by centrifugation and washed with DMF (15 ml) 3 times. The yellow solid was then immersed in methanol for 3 days, in which the solvent was exchanged 3 times during this time period. The solvent was removed by decantation and the wet solid was dried under vacuum ($10^{-5}$ torr) at 100° C. for 24 hours to afford the titled MET framework as a yellow powder, which was then stored in a desiccator. Yield: 75% based on $CoCl_2$ Analysis for $Co(C_2H_2N_3)_2$. Calculated: C, 24.62%, N, 43.08%, H, 2.07%, Measured: C, 23.40%, N, 39.00%, H, 2.42%. FT-IR: 3155 (m), 2984 (vw), 2459 (w), 2337 (w), 2231 (w), 1651 (m), 1623 (m), 1469 (m), 1419 (m), 1257 (m), 1198 (s), 1111 (vs), 1010 (w), 975 (s), 809 (vs), 716 (w).

Synthesis of MET-5 (Cu):

In a vial, $Cu(NO_3)_2.H_2O$ (1 mmol) was dissolved in DEF (10 ml). After adding 1H-1,2,3-triazole (3 mmol), the vial was capped and maintained at ambient temperature for 8 hours, and then at 100° C. for at least 18 hours. The resulting blue solid was washed with DEF three times. The blue solid was then immersed in methanol for 3 days, in which the solvent was changed 3 times during this time period. After the solvent was removed by decantation, the wet solid was dried under vacuum ($10^{-5}$ torr) at ambient temperature for 24 hours to afford the titled MET framework as a blue powder, which was then stored in a desiccator. Yield: 66% based on Cu(NO$_3$)$_2$. Elemental Analysis for Cu(C$_2$H$_2$N$_3$)$_2$. Calculated: C, 24.05%, N, 42.09%, H, 2.02, Cu 31.84%. Measured: C, 25.71%, N, 32.79%, H, 2.89% FT-IR: 3143 (m), 2368 (w), 2336 (w), 1650 (m), 1465 (m), 1425 (m), 1385 (m), 1318 (w), 1193 (s), 1109 (vs), 973 (s), 799 (vs), 715 (w).

Synthesis of MET-6 (Zn):

ZnCl$_2$ (1.00 g; 7.34 mmol) was dissolved in a solvent mixture of DMF (10 mL), Ethanol (10 mL), water (15 mL), and 30% ammonium hydroxide (5 mL). A visible white precipitate formed immediately upon dropwise addition of 1H-1,2,3-triazole (1.25 mL; 21.6 mmol) to the solution. The resulting suspension was then stirred at slow speed for 24 h. The white solid was collected by filtration, and washed with DMF and methanol. The white solid was then immersed in methanol for 3 days, in which the solvent was changed 3 times during this time period. After the solvent was removed by decantation, the wet solid was dried under vacuum (10$^{-5}$ torr) at 100° C. for 24 hours to afford the titled MET framework as a white powder, which was then stored in a desiccator. Yield: 850 mg (93% based on ZnCl$_2$). Elemental Analysis for Zn(C$_2$H$_2$N$_3$)$_2$. Calculated: C, 23.84%, N, 41.70%, H, 2.00, Zn, 32.46%. Measured: C, 23.50%, N, 42.02%, H, 2.000% Zn %. FT-IR: 3146 (m), 3128 (w), 1645 (m), 1462 (m), 1423 (m), 1236 (w), 1213 (m), 1190 (s), 1109 (vs), 997 (w), 977 (s), 798 (vs), 721 (m).

Synthesis of MET-7 (Cd):

In a vial, Cd(NO$_3$)$_2$.4(H$_2$O) (0.4 mmol) was dissolved in DEF (2 ml). After adding 1H-1,2,3-triazole (1 mmol) to this solution, the vial was capped and placed in a preheated oven at 120° C. for 24 h. The resulting white solid was collected by filtration, and washed with DEF three times. The white solid was then immersed in methanol for 3 days, in which the solvent was changed 3 times during this time period. After the solvent was removed by decantation, the wet solid was dried under vacuum (10$^{-5}$ torr) at 100° C. for 24 hours to afford the titled MET framework as a white powder, which was then stored in a desiccator. Yield: 68% based on Cd (NO$_3$)$_2$. Elemental Analysis for Cd(C$_2$H$_2$N$_3$)$_2$. Calculated: C, 19.32%, N, 33.81%, H, 1.63, Cd, 45.24%. Measured: C, 19.06%, N, 34.98%, H, 1.54%. FT-IR: 3142 (m), 2966 (vw), 2931 (w), 2369 (w), 2335 (w), 1720 (w), 1653 (m), 1615 (m), 1465 (w), 1422 (m), 1263 (w), 1178 (s), 1100 (vs), 971 (s), 790 (vs), 713 (w).

The obtained MET framework powders were insoluble in common organic solvents (as expected for an extended framework) FT-IR spectra were recorded to investigate the bond formation between M(II) and 1,2,3-triazolate. The FT-IR spectra demonstrate the absence of the characteristic N—H stretching modes at 3357 cm$^{-1}$ in 1H-1,2,3-triazole and 3200 cm$^{-1}$ in 2H-1,2,3-triazole, indicating full deprotonation of the triazolate link. This is also supported by the solid-state $^{13}$C cross-polarization with magic angle spinning (CP-MAS) NMR measurements. The $^{13}$C CP-MAS NMR spectrum for MET-6 showed only one resonance signal at 128.8 ppm (130.3 ppm in triazole), therefore having both carbon atoms on the ring experiencing the same chemical environment. These observations imply that the triazolate ring must contain mm2 (C$_{2v}$) symmetry. The elemental analysis suggests a ratio of two triazolate per metal center (M(C$_2$H$_2$N$_3$)$_2$).

Thermal Gravimetric Analysis:

All samples were run on a Q-500 series thermal gravimetric analyzer (TA Instruments, New Castle, Del.) with samples held in platinum pans in a continuous-flow nitrogen atmosphere. Samples were heated at a constant rate of 5° C./min during all TGA experiments.

All of the METs are stable in air. No significant changes in the PXRD patterns were observed after several weeks of air exposure. They are also stable when immersed in common organic solvents (e.g. dichloromethane, chloroform, methanol, tetrahydrofuran, etc.), with no noticeable loss of crystallinity. The thermogravimetric analysis indicate that the MET frameworks are thermally stable, displaying no weight loss below the decomposition temperature, which varies with from ca. 250° C. in MET-6 to 400° C. in MET-2. The thermal gravimetric analysis of MET-1 to MET-6 are presented in FIGS. 1 to 6, respectively.

Powder X-Ray Data Collection:

Powder X-ray diffraction data were collected using a Bruker D8-advance □-2□ diffractometer in reflectance Bragg-Brentano geometry employing Ni filtered Cu K□ lines focused radiation (1.54059 Å, 1.54439 Å) at 1600 W (40 kV, 40 mA) power and equipped with a Vantec detector, with an electronic window of 6°, fitted at 0.6 mm radiation entrance slit. Samples were mounted on zero background sample holders by dropping powders from a wide-blade spatula and then leveling the sample with a razor blade. The best counting statistics were achieved by collecting samples using a 0.02° 2□ step scan from 1-90° with exposure time of 10 s per step. All measurements were performed at ambient temperature and atmospheric pressure.

Figure 7:
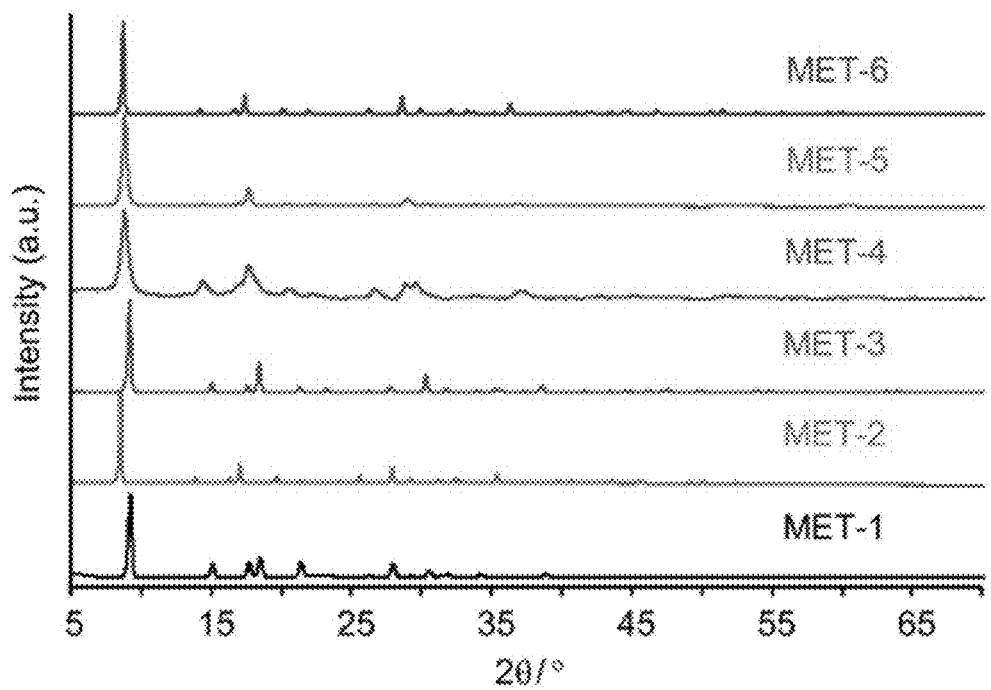
FIG. 7 provides Powder X-ray diffraction patterns for MET-1 to 6.
Figure 8:
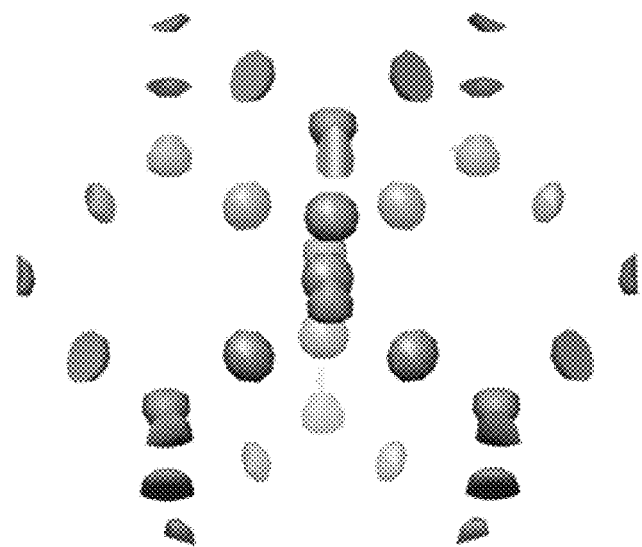
FIG. 8 provides a MET-5 (Cu) electron density map. Only regions of high density corresponding to Cu atoms are shown for clarity.
Figure 9:
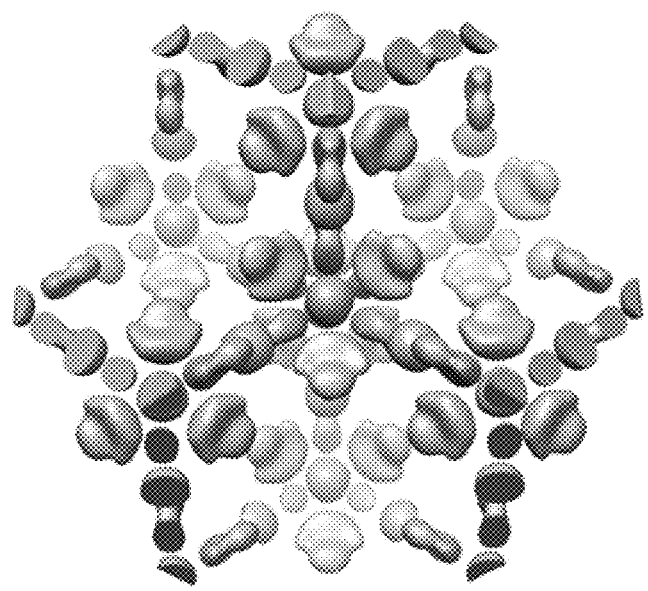
FIG. 9 provides a MET-2 (Mn) electron density map, showing the position of the Mn atoms as well as the triazole rings.
Figure 10:
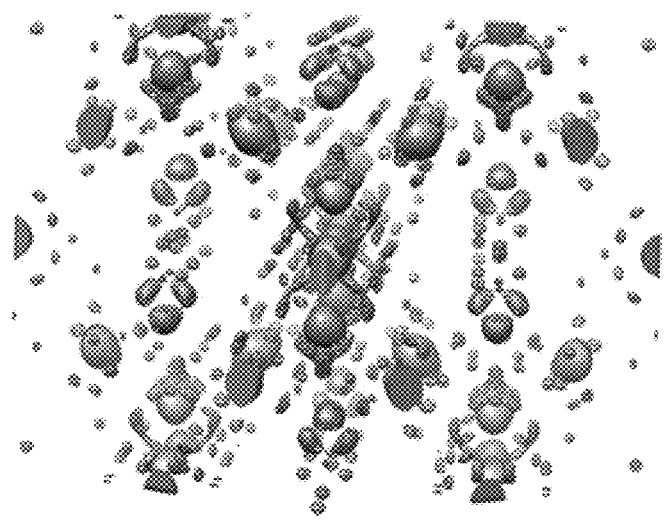
FIG. 10 provides a MET-3 (Fe) electron density map. Both the positions of the Fe atoms in the framework and the density of the guest molecules in the pores can be observed.
Figure 11:
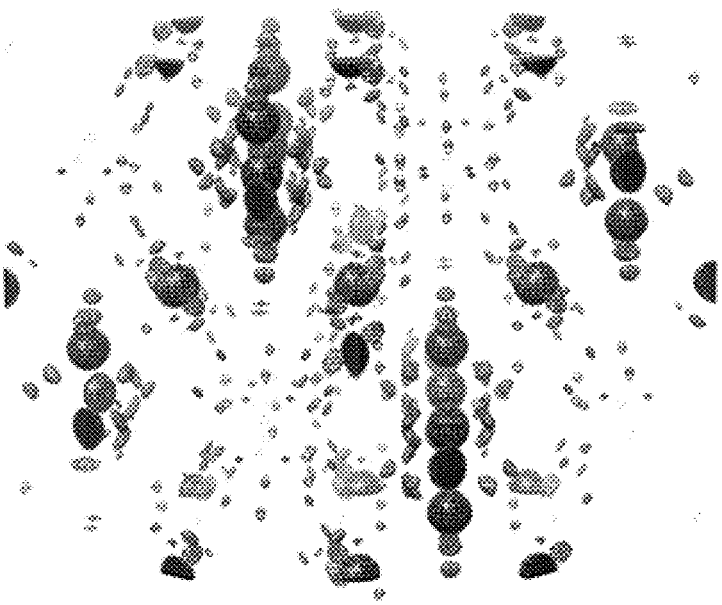
FIG. 11 provides a MET-7 (Cd) electron density map, showing the positions of the Cd atoms in the framework and the density of the guest molecules in the pores.
Figure 12:
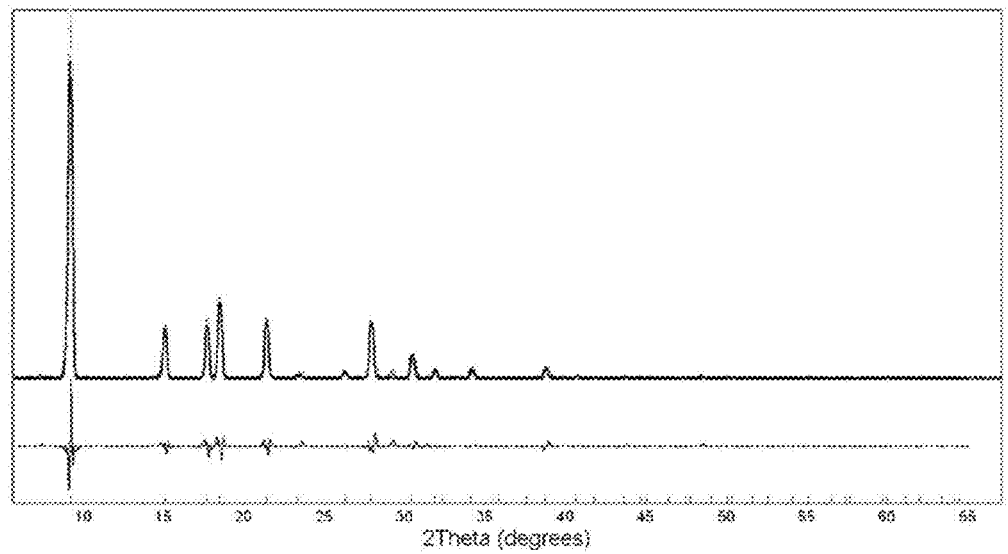
FIG. 12 provides a MET-1 (Mg) Rietveld Refinement tracing, showing the experimental and simulated, grey line and black line respectfully, which are combined in the top line and the difference between the experimental and simulated in the bottom line. Bragg positions are marked as columns.
Figure 13:
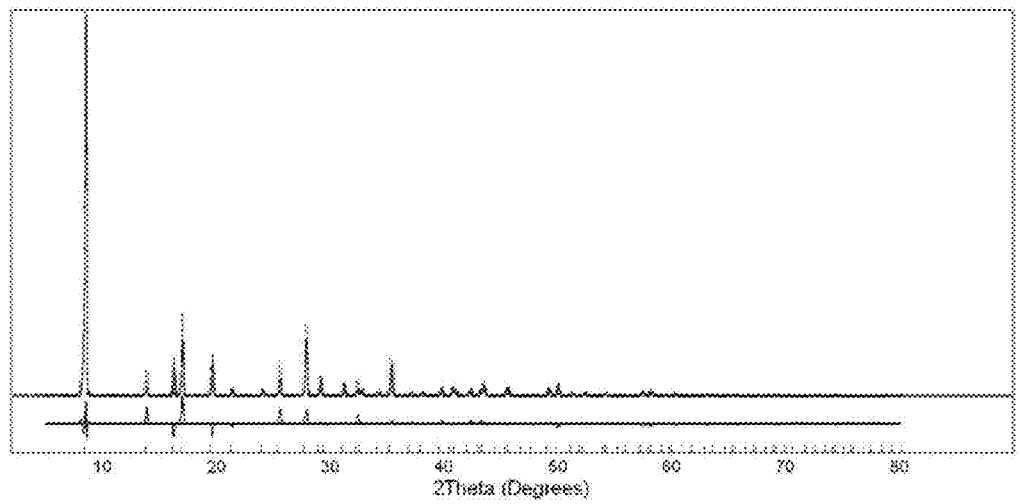
FIG. 13 provides a MET-2(Mn) Rietveld Refinement tracing, showing the experimental and simulated, grey line and black line respectfully, which are combined in the top line and the difference between the experimental and simulated in the bottom line. Bragg positions are marked as columns.
Figure 14:
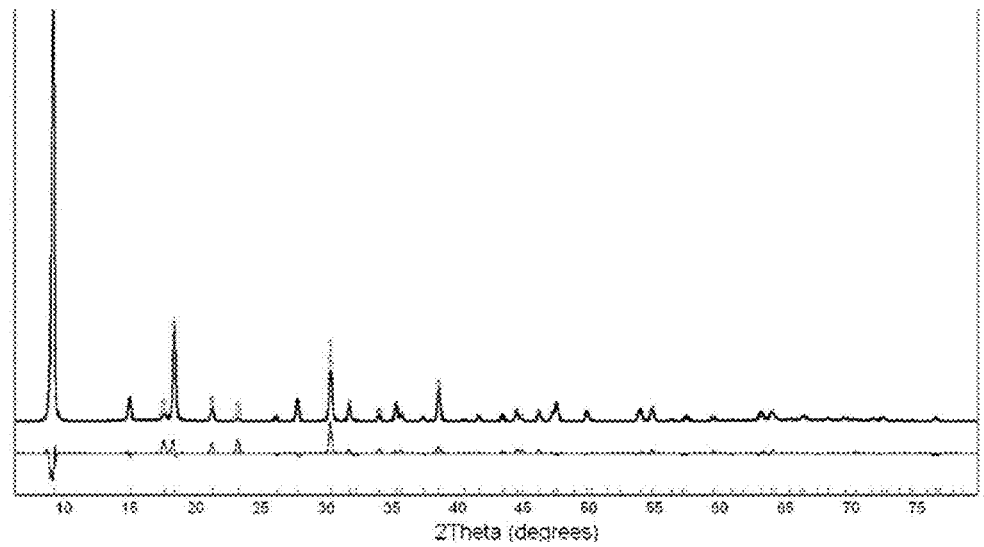
FIG. 14 provides a MET-3(Fe) Rietveld Refinement tracing, showing the experimental and simulated, grey line and black line respectfully, which are combined in the top line and the difference between the experimental and simulated in the bottom line. Bragg positions are marked as columns.
Figure 15:
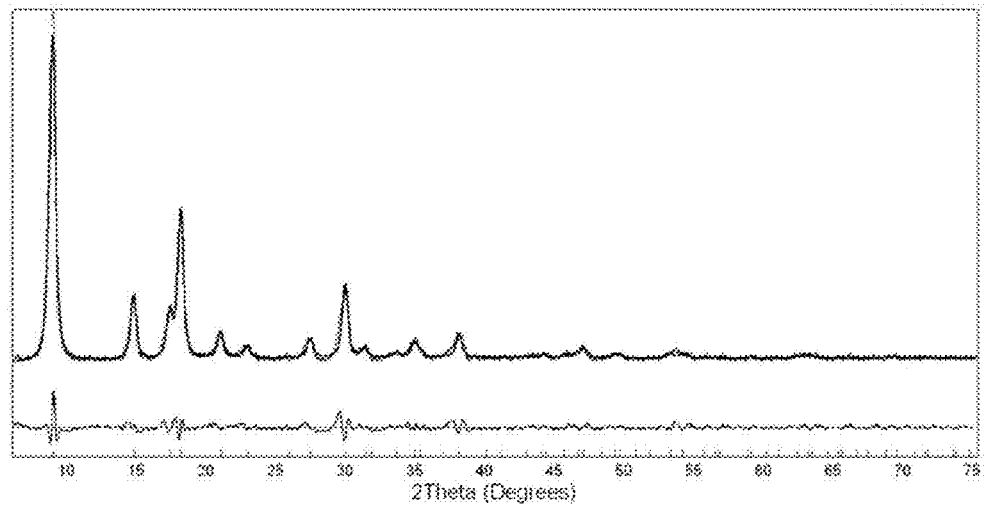
FIG. 15 provides a MET-4(Co) Rietveld Refinement tracing, showing the experimental and simulated, grey line and black line respectfully, which are combined in the top line and the difference between the experimental and simulated in the bottom line. Bragg positions are marked as columns.
Figure 16:
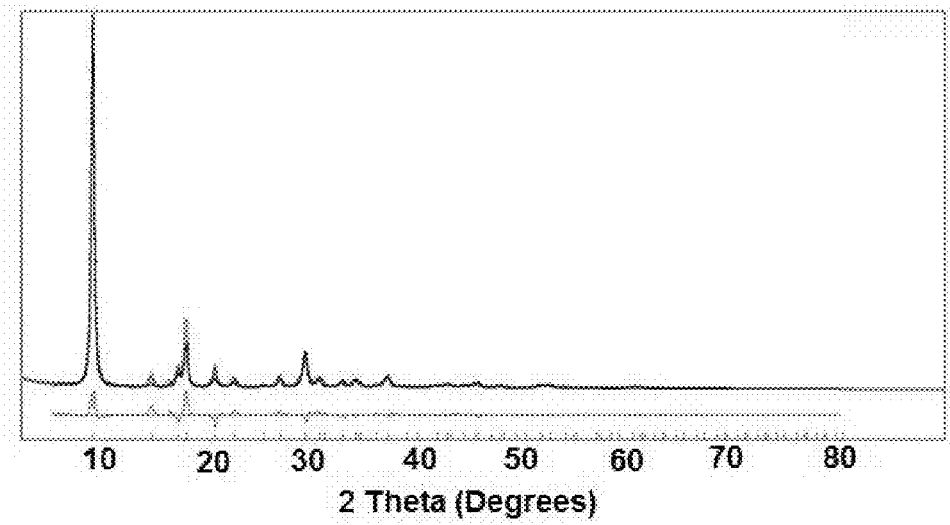
FIG. 16 provides a MET-5(Cu) Rietveld Refinement tracing, showing the experimental and simulated, grey line and black line respectfully, which are combined in the top line and the difference between the experimental and simulated in the bottom line. Bragg positions are marked as columns.
Figure 17:
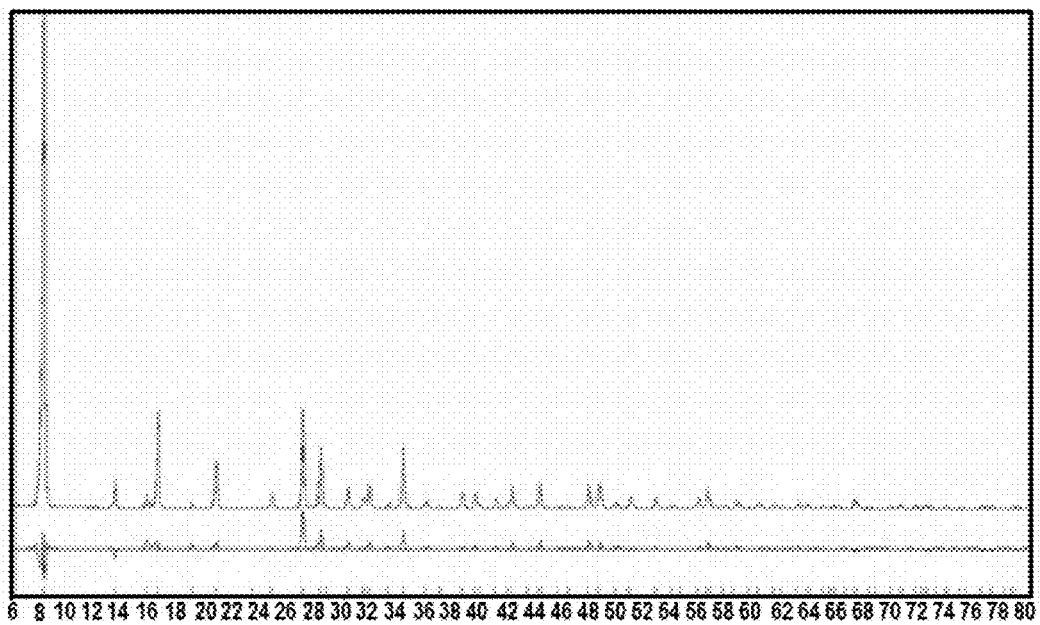
FIG. 17 provides a MET-7(Cd) Rietveld Refinement tracing, showing the experimental and simulated, grey line and black line respectfully, which are combined in the top line and the difference between the experimental and simulated in the bottom line. Bragg positions are marked as columns.
Figure 18:
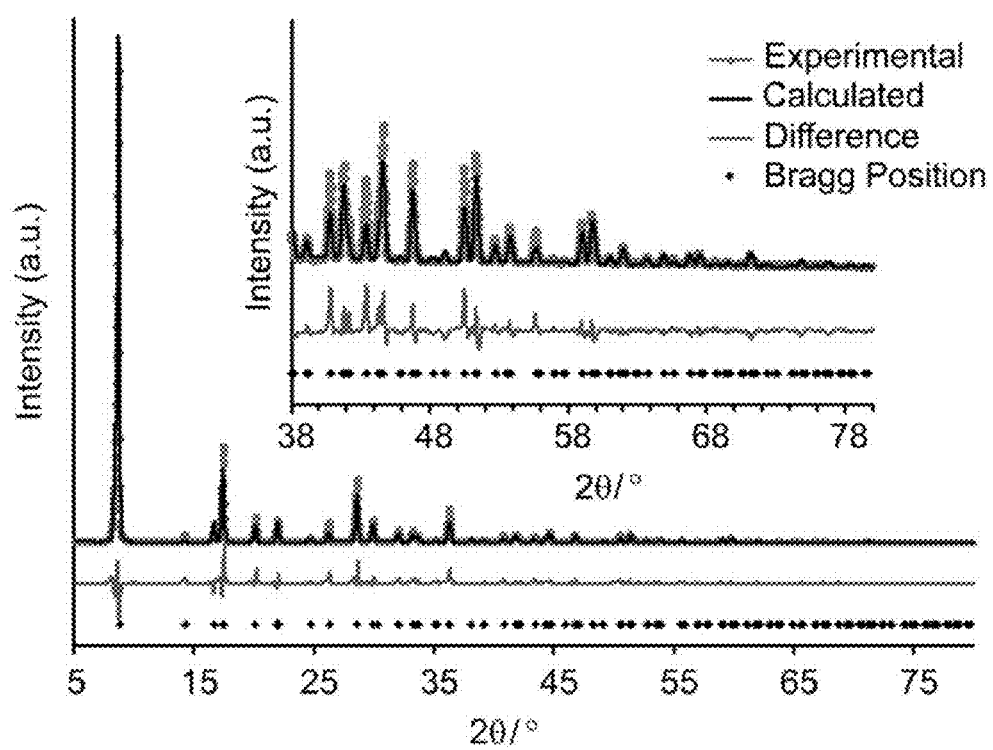
FIG. 18 provides a Rietveld refinement tracing of the MET-6(Zn) framework showing the experimental, calculated and difference patterns, as indicated. Bragg positions are marked as black crosses. Inset: zoom of the high angle area.

Numerous attempts to obtain the METs as single crystals for X-ray diffraction were unsuccessful. Nevertheless, the METs were obtained as microcrystalline powders exhibiting intense diffractions lines (FIG. 7) from which it was possible to determine accurate crystal structures.

Unit Cell Determination:

Unit cell determinations were carried out using Materials Studio Reflex Indexing module for peak selection and interfacing with DICVOL. Full profile matching and extraction of the integrated intensities (I$_{obs}$) was conducted with Topas [S] using data from 2θ=5-80°. Background was first refined applying a 2$^{nd}$ order Chebyschev Polynomial. The profile was calculated starting with the unit cell parameters obtained from the indexation process, and the space group Fd$\bar{3}$m, which is in agreement with the systematic absences of the diffraction patterns. The integrated intensities (F$_{obs}^2$) were extracted by a full pattern decomposition using a Thomson-Cox-Hasting pseudo Voigt or a Pearson VII peak profile, followed by refinement of peak asymmetry using Finger et al. asymmetry function. Unit cells and zero-shift were then refined with peak asymmetry. Once this was achieved, the background was refined with 20$^{th}$-order polynomial. Refinement of unit cell parameters, zero shift, peak asymmetry, Lorentz polarization, crystallite size and strain, and linear absorption were used for the final profile.

Unit Cell Determination of MET-2 (Mn), MET-6 (Zn), and MET-7 (Cd):

Satisfactory solutions in the cubic system were found for three of the MET frameworks: MET-6, 2 and 7. Table 1 presents the obtained values of the indexed unit cell parameters for these MET frameworks.

TABLE 1

| MET | Lattice parameter (Å) | $M_{(20)}$ | $F_{(20)}$ |
|---|---|---|---|
| MET-6 (Zn) | 17.67151 | 30 | 29 (0.0049, 140) |
| MET-2 (Mn) | 18.16552 | 22.8 | 23.5 (0.0064, 132) |
| MET-7 (Cd) | 18.63646 | 13.9 | 15.9 (0.0111, 113) |

Pawley Refinement:

Full pattern profile matching and extraction of the integrated intensities ($I_{obs}$) was conducted with Topas using data from 2θ=5°-80°. Background was first refined applying a $2^{nd}$ order Chebyschev Polynomial function. The profile was calculated starting with the unit cell parameters obtained from the indexation process, and the space group Fd$\bar{3}$m, which is in agreement with the systematic absences of the diffraction patterns. The integrated intensities ($F_{obs}^2$) were extracted by a full pattern decomposition using a Thomson-Cox-Hasting pseudo Voigt or a Pearson VII peak profile, followed by refinement of peak asymmetry using Finger et al. asymmetry function. Unit cells and zero-shift were then refined with peak asymmetry. Once this was achieved, the background was refined with $20^{th}$-order polynomial. Refinement of unit cell parameters, zero shift, peak asymmetry, Lorentz polarization, crystallite size and strain, and linear absorption were used for the final profile.

Unit Cell Determination of MET-1 (Mg), MET-2 (Mn), MET-3 (Fe), MET-4 (Co), MET-5 (Cu), MET-6 (Zn) and MET-7 (Cd):

For the other MET frameworks, the unit cell parameters were refined performing a full pattern profile matching (Pawley refinement) using the MET-1 unit cell values as starting values. Table 2 presents the refined unit cell parameters and residual values for each compound:

TABLE 2

| MET | a (Å) | $R_p$ | $R_{wp}$ | GOF |
|---|---|---|---|---|
| MET-1 (Mg) | 16.599(5) | 6.02 | 8.87 | 2.05 |
| MET-2 (Mn) | 18.160(1) | 4.87 | 8.79 | 8.46 |
| MET-3 (Fe) | 16.669(5) | 6.30 | 8.05 | 2.25 |
| MET-4 (Co) | 16.808(6) | 2.12 | 2.99 | 1.78 |
| MET-5 (Cu) | 17.371(8) | 4.36 | 6.46 | 4.55 |
| MET-6 (Zn) | 17.734(1) | 2.48 | 3.49 | 2.33 |
| MET-7 (Cd) | 18.597(1) | 5.87 | 8.88 | 6.20 |

Electron Density Calculation:

Electron density maps were calculated using Superflip (Superflip—a computer program for the solution of crystal structures by charge flipping in arbitrary dimensions). The maps were calculated for all the compounds except for the MET-1 and MET-4, due to the lower quality of the diffraction patterns of these materials.

Calculations were first made by assuming that the observed intensities were extracted from single crystal data using the indexed integrated intensities obtained from Pawley fitting, later calculations were performed adapting the powder patterns routine with the histograms generated by the composition observed after the observation of electron density maps generated by the assumption of using single crystal. Electron density maps were also calculated with intensities extracted in the space group P1; all the cases, resulted in valid density maps with Fd$\bar{3}$m as the proposed group. The electron density maps were visualized and the images produced with the Chimera software.

From the calculated maps with best figures of merit, it could be observed immediately the dia topology with $M^{2+}$ atoms at the vertices and edges of the net. For the materials with diffraction pattern with higher resolution (Zn, Mn), electron density at higher intensity allowed the visualization of the 5 member rings of the triazolates with 3 regions (potentially nitrogen atoms) pointing to $M^{2+}$ atoms in octahedral geometry. In all the cases, some electron density was observed in the center of the cell probably belonging to guests inside the pore system. The Electron density maps for MET-5, MET-2, MET-3, and MET-7 are presented in FIGS. 8, 9, 10, and 11, respectively. The Electron density map for MET-6 is presented in FIG. 20, panel a and b.

The PXRD pattern of MET-6 contains reflections up to a resolution of 1.2 Å (2θ=80°) and it was possible to index it ab initio using the Dicvol program, resulting in a cubic unit cell with parameter a=17.671 Å [figures of merit $M_{20}$=30, $F_{20}$=29 (0.004877, 60)]. The systematic absences suggested an F-centered cell, and space group most probably Fd$\bar{3}$ or Fd$\bar{3}$m. With this information, a Pawley refinement was performed on the experimental diffractogram to obtain the integrated intensities ($F^2_{obs}$ or $I_{hkl}$), resulting in convergent refinements and low residuals (a=17.708 Å, $R_p$=2.48%, $wR_p$=3.49%). A charge-flipping algorithm was then applied with these extracted intensities and the refined unit cell parameters of MET-6 to calculate electron density maps on the Superflip program.

The charge flipping method has been recently developed, and has found a great acceptance among the crystallographic community, and it demonstrated to be very successful for the structure solution of some interesting structures. These structures were determined by synchrotron powder X-ray data, or in combination with electron diffraction methods.

Since the chemical composition of the entire unit cell is not known, the obtained structure factors without any other chemical information was used to calculate rough electron density maps. From these early maps the number and position of heavy atoms were determined. The symmetry of these density maps is in agreement with the Fd$\bar{3}$m space group. Two crystallographically independent Zn atoms can be located from the map, at special positions $\bar{4}3$m (0, 0, 0) and 0.3 m (⅛, ⅛, ⅛). This disposition corresponds to an arrangement of the Zn atom in a dia (diamond) topology with a total of 24 Zn atoms per unit cell, with Zn atoms at the vertexes and at the edges of the net. Based on the composition of MET-6 as determined by elemental analysis, $Zn(C_2H_2N_3)_2$ (calculated: C, 23.84%, N, 41.70%, H, 2.00% found: C, 23.50%, N, 42.02%, H, 2.00%), each unit cell has a composition of $Zn_{24}C_{96}N_{144}H_{96}$. Further electron density maps were calculated using the algorithm adapted for powder patterns, where a histogram matching is performed using the chemical composition of the unit cell (see FIG. 20, panel a and b).

The second generation of electron density maps resulted in higher resolution and showed the presence of 5-membered rings, assigned to the triazolate units. Three of the atoms surround three different Zn atoms; chemical logic suggests that these three atoms are nitrogen. The 5-membered rings have a site-symmetry, mm2 ($C_{2v}$), which is consistent with the spectroscopic observations, with one of the N atoms at this special position (x, 0, 0), and the other two at (x, x, z) sites (FIG. 20, panel b).

Figure 20:
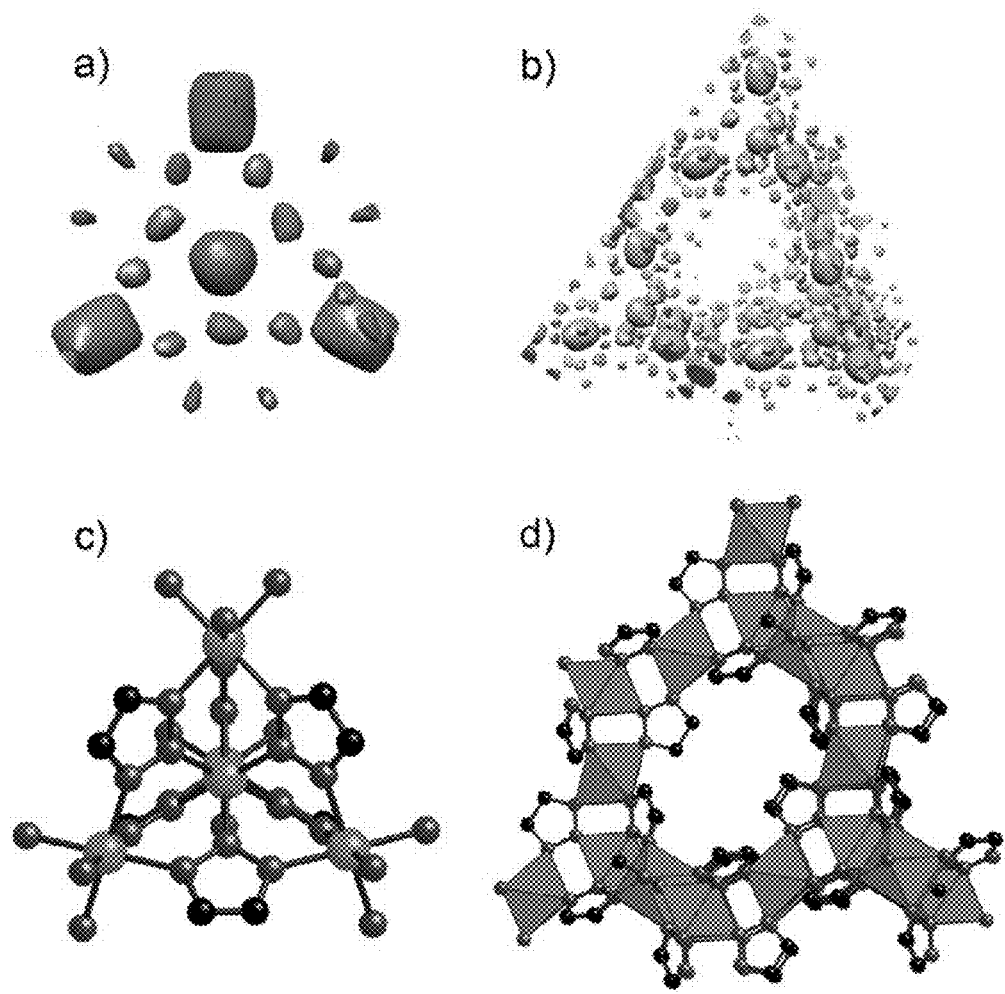
FIG. 20 presents an illustration of the deduced structure of the MET-6 framework. Top: electron density maps obtained by applying the charge-flipping method the PXRD data (a). The full unit cell is shown in (b). Bottom: Deduced structure of MET-6 based from the electron density map. The tetrahedral SBU is shown in (c). The polyhedral representation of the framework is shown in (d). Metal atoms are represented as large grey spheres (c) or grey polyhedra (d), nitrogen and carbon atoms are small grey spheres and black spheres, respectively. Hydrogen atoms are omitted for clarity.

Additionally, these maps show the presence of a pore channel where some electron density was observed, probably corresponding to guest molecules (FIG. 20, panel b). To ensure the assignment of the space group and the symmetry derived from the density maps is not influenced by the initial choice of the space group for the extraction of the intensities, the intensities were expanded to P1 symmetry (equal partition of intensity of overlapped peaks), and then performed the charge flipping algorithm followed by the symmetry search. Multiple runs all converged on the Fd-3m space group.

Figure 19:
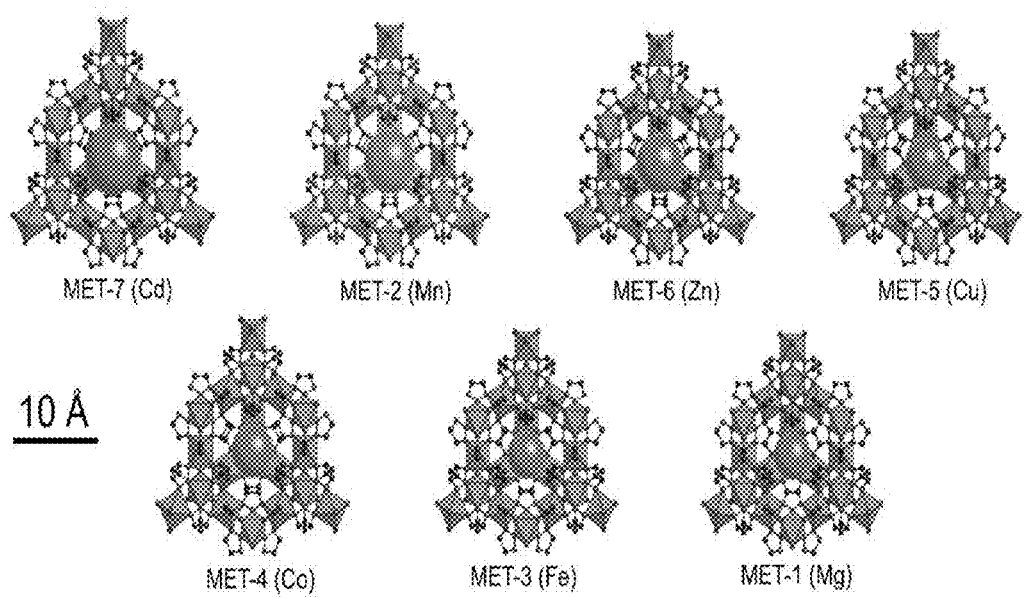
FIG. 19 presents an illustration of the controlled pore size, as indicated by the large grey sphere, in the isoreticular series of METs. C atoms are represented as small black spheres, N atoms as small grey spheres, metal atoms as grey polyhedra.

Rietveld Refinements:

Rietveld refinements were performed using TOPAS and the Reflex Module from Materials Studio, using data from $2\theta=5\text{-}80°$. The profile obtained from Pawley fitting and the model generated, were used as a starting set. The profile used was a Thomson-Cox-Hasting Pseudo Voigt function with 6 terms or Pearson-VII, with a $20^{th}$ order Chebychev polynomial and Finger-Cox-Jephcoat peak asymmetry (2 parameters). Unit cell parameter, zero-shift correction, Lorentz polarization, linear absorption, scale, crystallite size and strain were refined observing convergent refinements. Atoms MET-1, -2, -3, -4, -5 and -7 were proved to be isostructural similar to MET-6 by means of powder X-ray diffraction. The same protocol for the structure solution was carried out for MET-2, -3, -5 and -7. In all the cases, the positions of the metal atoms were clearly identified in the electron density maps. Rietveld refinements were equally performed, converging with satisfactory residual values. In the case of MET-1 and 4, with much broader peaks, only a refinement of the unit cell parameters with full pattern profile matching could be performed. The calculated pore diameter varies in the MET series from 4.5 Å in MET-1 and -3, to 6.1 Å for MET-2, and to about 6.8 Å in the case of MET-7. The values for the seven MET materials are summarized in Table 3, together with their refined unit cell parameters, and specific surface area values. By choosing elements with different ionic radii, small changes in the lattice parameters are observed and networks with the same topology but different pore sizes are achieved (FIG. 19).

TABLE 3

| Name | MET-2 | MET-3 | MET-5 | MET-6 | MET-7 |
|---|---|---|---|---|---|
| Refined Composition | $Mn_{24}N_{144}C_{96}H_{96}$ | $[Fe_{24}N_{144}C_{96}H_{96}]O_{32.1}$ | $[Cu_{24}N_{144}C_{96}H_{96}]O_{16}$ | $Zn_{24}N_{144}C_{96}H_{96}$ | $[Cd_{24}N_{144}C_{96}H_{96}]O_{25.9}$ |
| Mass Formula (g mol$^{-1}$) | 4586.1 | 5217.9 | 4797.5 | 4837 | 6428.04 |
| Crystal system Space Group | | | Cubic Fd$\bar{3}$m (No. 227) | | |
| $a$ (Å) | 18.142(6) | 16.652(1) | 17.459(4) | 17.734(1) | 18.6333270 |
| $V$ (Å$^3$) | 5971.70(1) | 4617.99(1) | 5322.21(6) | 5577.91(8) | 6469.50742 |
| Crystal density (g cm$^{-3}$) | 1.431 | 1.875 | 1.496 | 1.338 | 1.531 |
| Number of independent atoms | 5 | 7 | 6 | 5 | 6 |
| $R_p$ (%) | 7.70 | 16.39 | 10.00 | 18.20 | 16.77 |
| $R_{wp}$ (%) | 11.22 | 22.88 | 11.86 | 24.25 | 24.34 |
| $R_B$ (%) | 9.653 | 13.824 | 5.357 | | 9.995 |
| GOF ($x^2$) | 9.31 | 12.31 | 11.44 | | 17.11 | positions were refined constraining the triazolate unit as a rigid body. Oxygen atoms were included inside the pores for MET-3, MET-5 and MET-7, to partially correct the influence of the guest molecules, and their positions and occupancy factors were refined. Isotropic thermal parameters ($U_{iso}$) with cell parameters were determined. Hydrogen atoms of the triazole rings were calculated and finally included in the refinements. The Rietveld refinements for MET-1, MET-2, MET-3, MET-4, MET-5, MET-7, and MET-6 are presented in FIGS. 12-18, respectively.

With the atomic positions derived from the electron density maps with the best convergence residual, a crystal model was generated using Material Studio and Rietveld refinements were performed over the experimental powder pattern obtaining convergent refinements with moderate residuals (a=17.73411(88) Å, $R_p$=18.1%, $wR_p$=25.1%). The value of these residuals was attributed to the effect of disorder solvent and guest molecules present inside the pore.

The X-ray crystal structure of MET-6 is illustrated in FIG. 20. The Zn(II) ions in the structure are all octahedral, bound to the N atoms of the triazolate rings. There are two crystallographically distinct Zn positions, forming a penta-atomic tetrahedral SBU (FIG. 20, panel C) with Zn atoms at the center and at the vertices of the tetrahedron. Each triazole ring bridges three Zn atoms: the N atom at position 2 binds to the atom at the center of the SBU, and the N atoms at positions 1 and 3 bind to two atoms at the vertices of the SBU. These tetrahedral units assemble by sharing vertices to form a dia network (FIG. 20, panel d).

Figure 21:
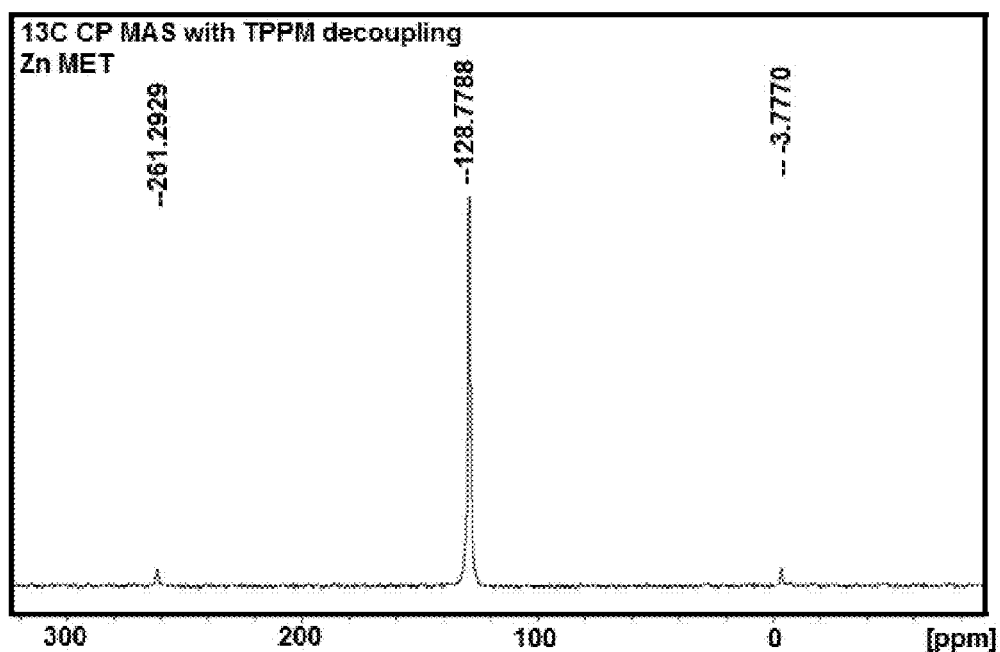
FIG. 21 provides the solid-state NMR spectrum of MET-6. The $^{13}$C chemical shifts are given relative to tetramethylsilane as zero ppm, calibrated using the methylene carbon signal of adamantane assigned to 37.77 ppm as the secondary reference.

MET-6 Solid State NMR:

High resolution solid-state NMR spectra were recorded at ambient pressure on a Bruker DSX-300 spectrometer using a standard Bruker magic angle-spinning (MAS) probe with 4 mm (outside diameter) zirconia rotors. The magic angle was adjusted by maximizing the number and amplitudes of the signals of the rotational echoes observed in the $^{79}$Br MAS free induction decay (FID) signal from KBr. Cross-polarization with MAS (CP-MAS) used to acquire $^{13}$C data at 75.47 MHz. The $^1$H and $^{13}$C ninety-degree pulse widths were both 4 µs. The CP contact time varied from 1.5 to 5 ms. High power two-pulse phase modulation (TPPM) $^1$H decoupling was applied during data acquisition. The decoupling frequency corresponded to 72 kHz. The MAS sample-spinning rate was 10 kHz. Recycle delays between scans varied between 3 and 20 s, depending upon the compound as determined by observing no apparent loss in the $^{13}$C signal from one scan to the next. The $^{13}$C chemical shifts for MET-6 are given relative to tetramethylsilane as zero ppm, calibrated using the methylene carbon signal of adamantane assigned to 37.77 ppm as the secondary reference (FIG. 21).

Figure 22:
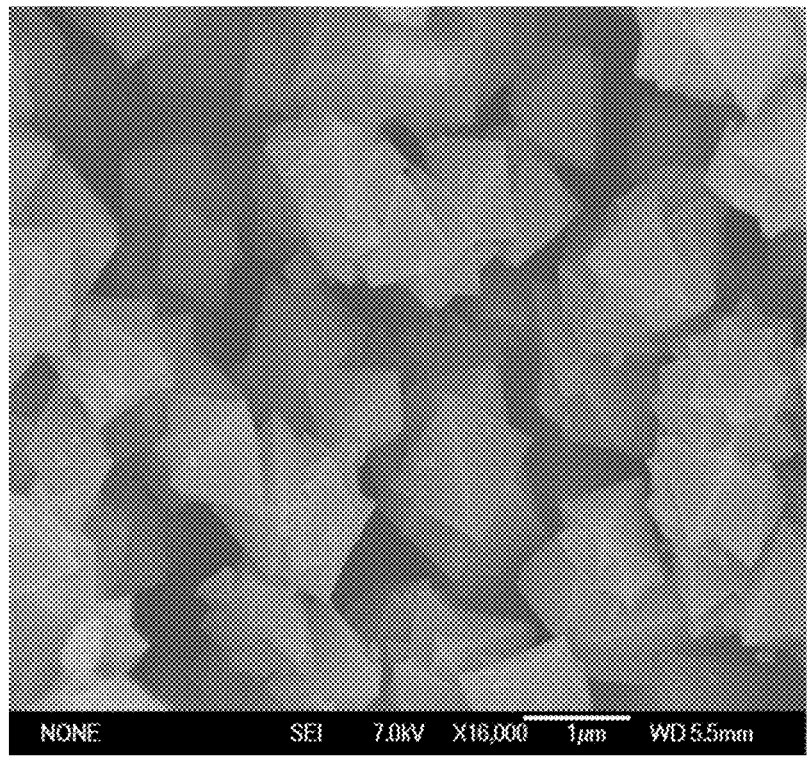
FIG. 22 presents a scanning electron photograph of synthesized MET-6.
Figure 23:
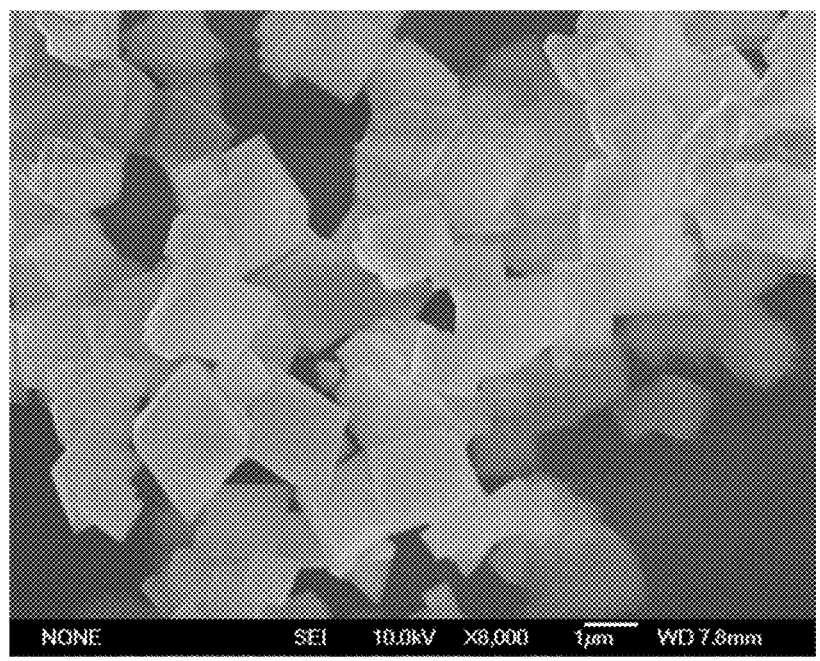
FIG. 23 presents a scanning electron photograph of synthesized MET-2.

Scanning Electron Microscopy (SEM):

Samples of synthesized MET-2 and MET-6 were measured by dispersing the material onto a sticky carbon surface attached to a flat aluminum sample holder. The samples were then gold coated using a Hummer 6.2 Sputter at ambient temperature and a pressure of 70 mtorr in an argon atmosphere for 30 s while maintaining a current of 15 mA. Samples were analyzed using a JOEL JSM-6700 Scanning Electron Microscope using both the SEI and LEI detectors with accelerating voltage of 7 kV. Multiple samples were surveyed. Only a unique morphology was apparent after exhaustive examination of a range of particle sizes that were deposited on the sample holder. Clusters of octahedral particles were observed of size of 1×1 μm approximately. No evidence for the presence of other phases was observed in the surveyed samples. FIG. 22 presents the SEM image of MET-6, while FIG. 23 presents the SEM image of MET 2.

Ar Sorption Isotherms and Surface Area Calculation:

Low pressure gas adsorption isotherms were measured volumetrically on an Autosorb-1 analyzer (Quantachrome Instruments). A liquid Ar bath was used for adsorption measurements at 87 K. The gas used was UHP grade (99.999%). For the calculation of surface areas, the Langmuir and BET methods were applied using the adsorption branches of the Ar isotherms assuming a Ar cross-sectional area of 14.2 $Å^2$/molecule. BET areas were calculated in pressure range with values of $v(P_0-P)$ increasing with $P/P_0$, according to the method reported by Walton and Snurr. The pore volume was determined using the Dubinin-Radushkevich (DR) method with the assumption that the adsorbate is in the liquid state and the adsorption involves a pore-filling process.

Figure 24:
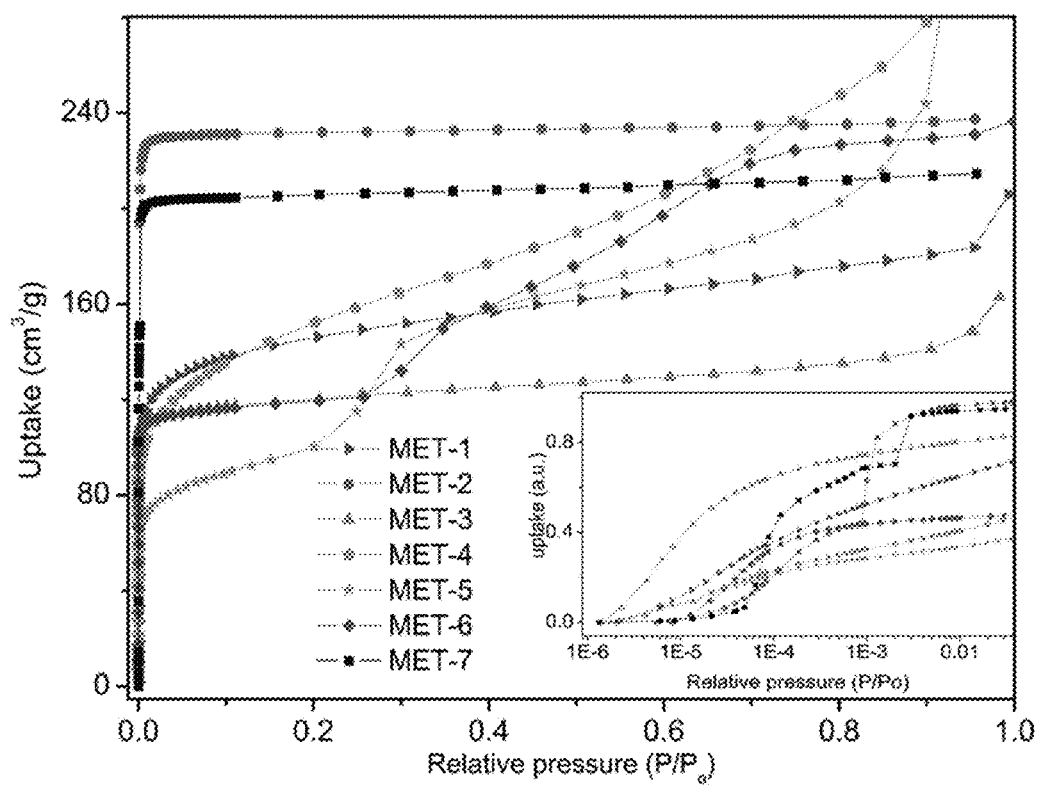
FIG. 24 provides a plot of the Ar isotherms collected at 87 K for the MET-1 to -7. In the inset, the isotherms with normalized uptake are shown in a semi-logarithmic scale, evidencing the differences in the pore sizes.
Figure 25:
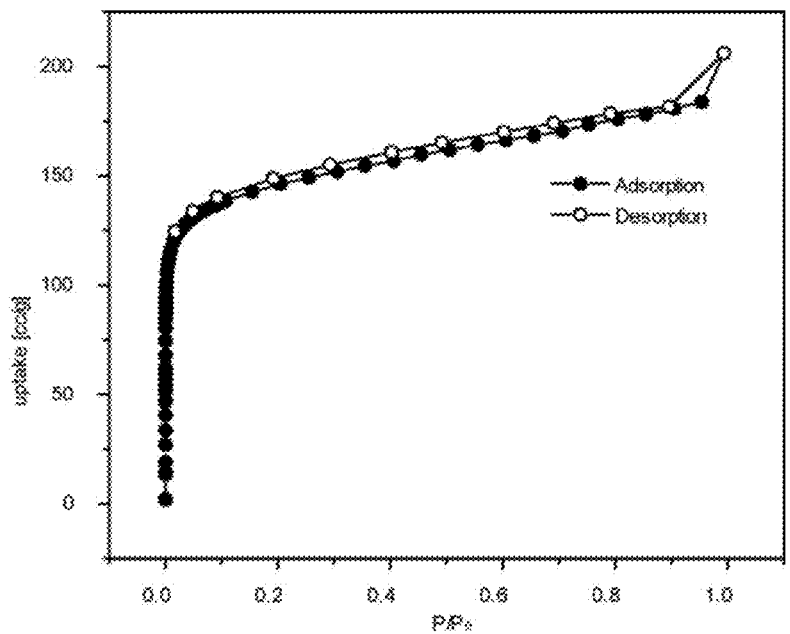
FIG. 25 provides a plot of the Ar isotherm for MET-1. A liquid Ar bath was used for adsorption measurements at 87 K. The MET-1 isotherm demonstrates the expected micropore filling in the low pressure range, and the increase in the uptake at high pressure. The observed hysteresis is attributed to capillary condensation, indicating the presence of mesoporous intergrain voids.
Figure 31:
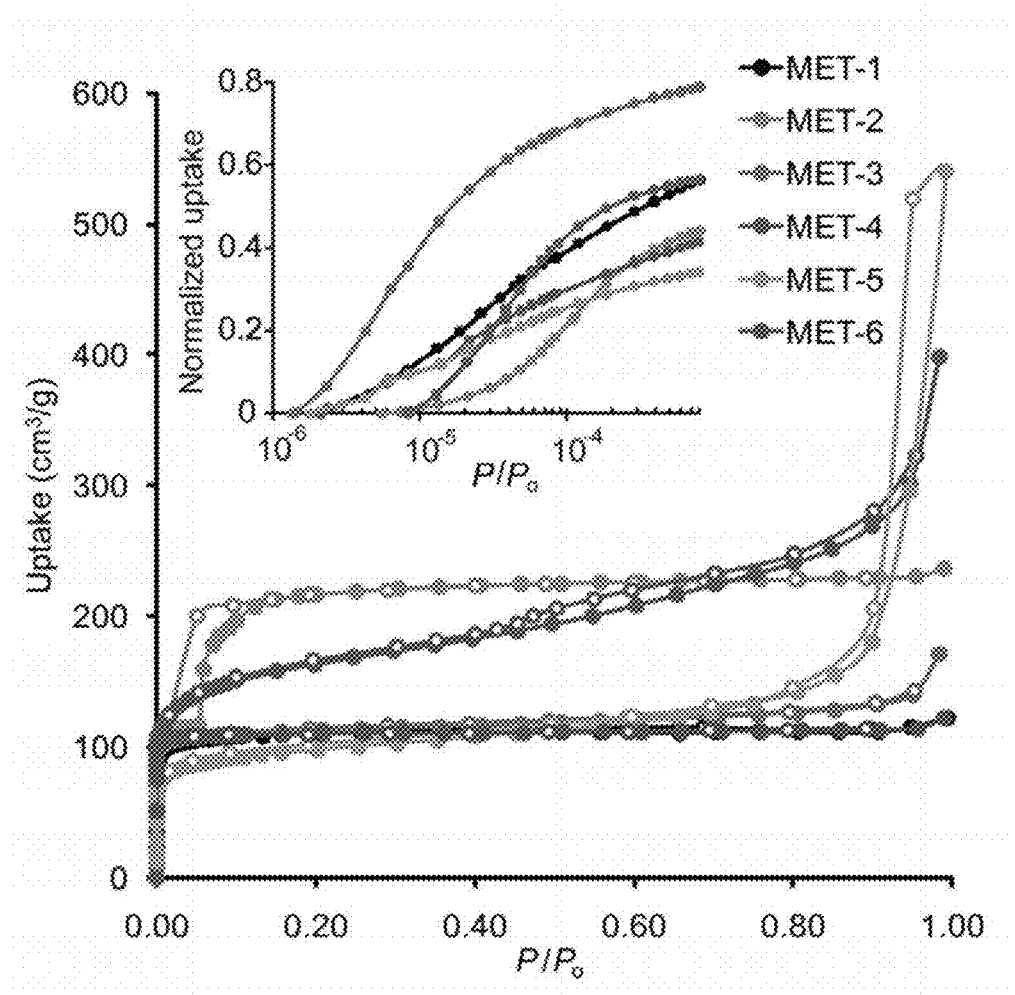
FIG. 31 provides $N_2$ isotherms of six MET frameworks (as indicated) that demonstrate the permanent porosity of these frameworks. Filled and open symbols represent adsorption and desorption branches, respectively. Inset figure: the normalized Ar isotherms are represented in a semi-logarithmic scale, to better appreciate the steps in the low pressure region, associated with the differences in the pore size.
Figure 32:
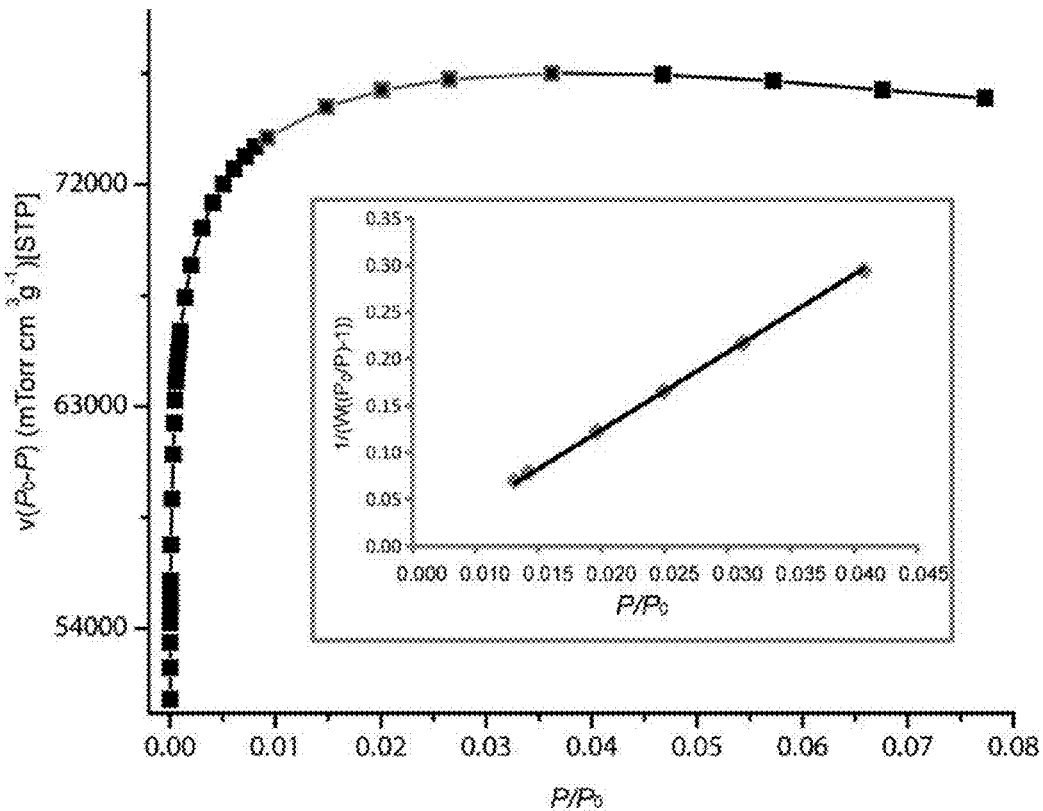
FIG. 32 provides a $N_2$ isotherm curve for MET-1. The curve is a plot of $v(P_0-P)$ against $P/P_0$, highlighting in dark grey as opposed to black, the points selected for the BET calculation of MET-1. A liquid $N_2$ bath was used for adsorption measurements at 77K. Inset shows the fitting plot for BET calculation.
Figure 33:
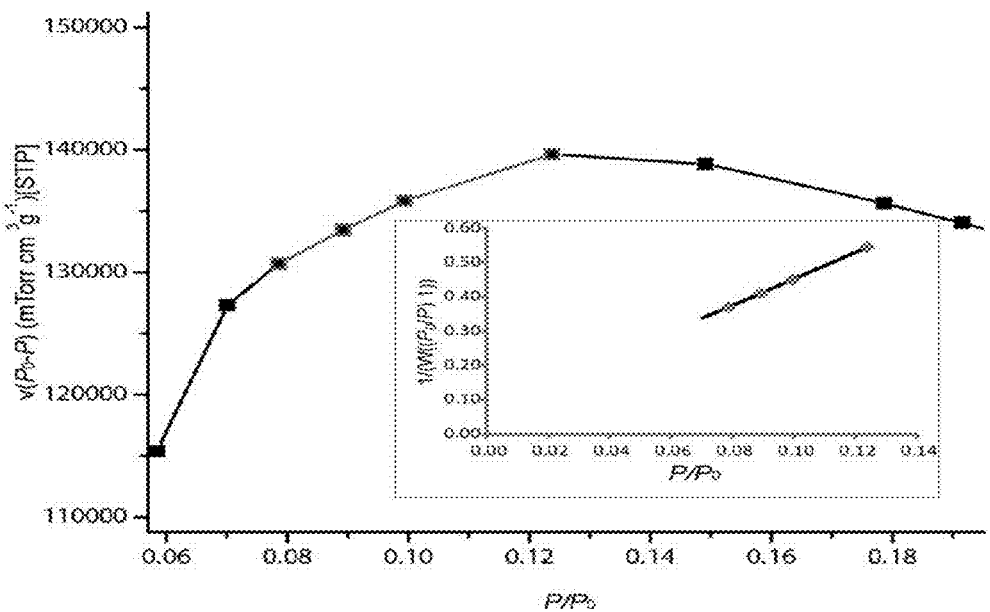
FIG. 33 provides a $N_2$ isotherm curve for MET-2. The curve is a plot of $v(P_0-P)$ against $P/P_0$, highlighting in dark grey as opposed to black, the points selected for the BET calculation of MET-1. A liquid $N_2$ bath was used for adsorption measurements at 77K. Inset shows the fitting plot for BET calculation.
Figure 34:
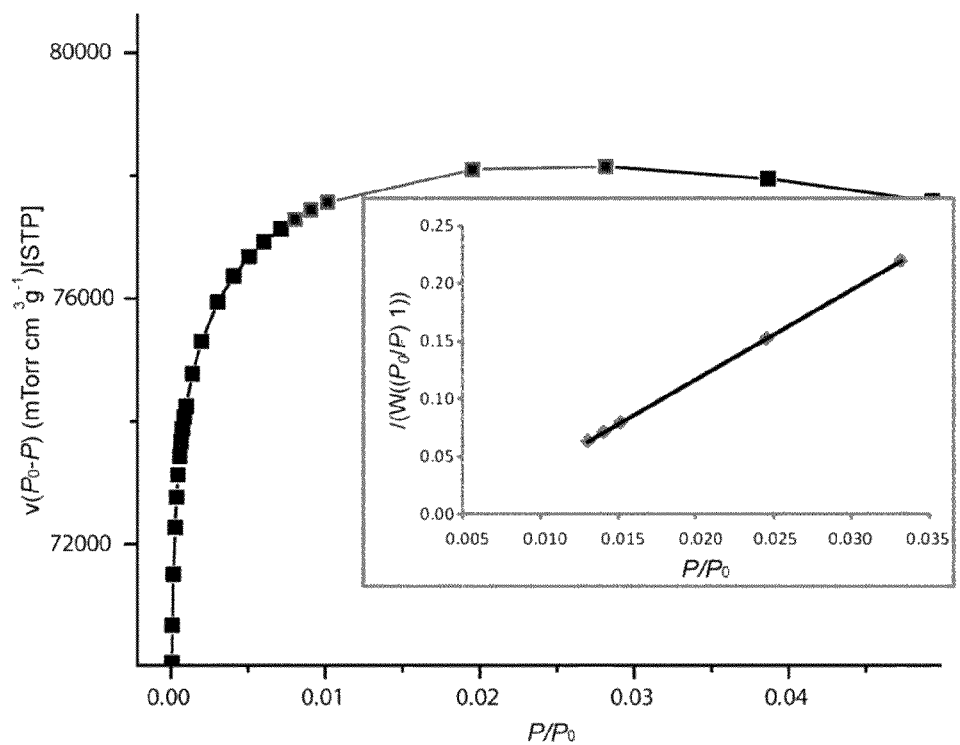
FIG. 34 provides a $N_2$ isotherm curve for MET-3. The curve is a plot of $v(P_0-P)$ against $P/P_0$, highlighting in dark grey as opposed to black, the points selected for the BET calculation of MET-1. A liquid $N_2$ bath was used for adsorption measurements at 77K. Inset shows the fitting plot for BET calculation.
Figure 35:
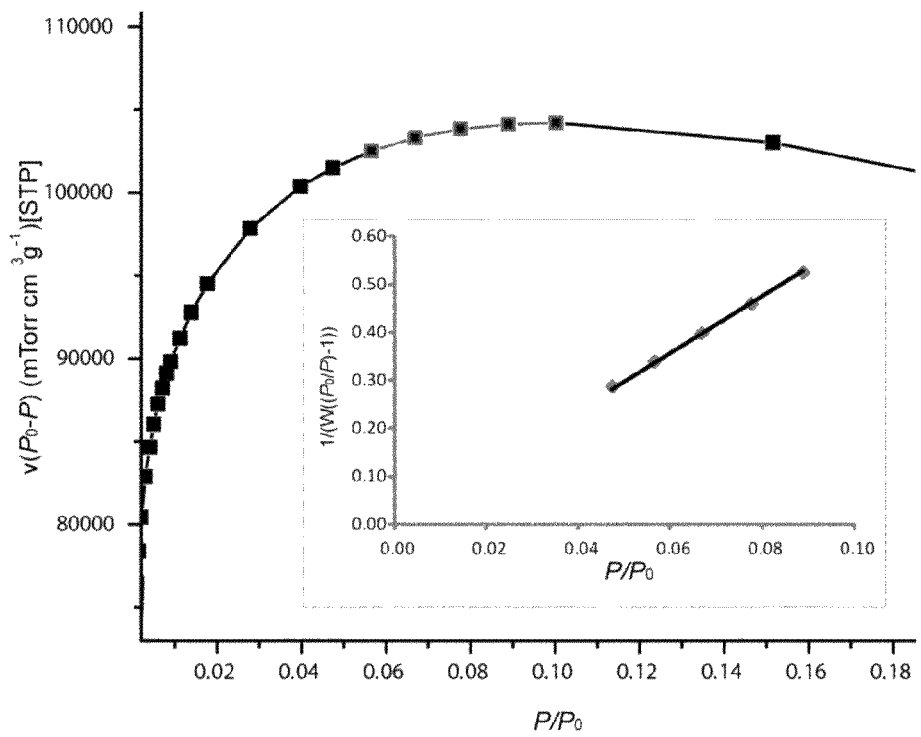
FIG. 35 provides a $N_2$ isotherm curve for MET-4. The curve is a plot of $v(P_0-P)$ against $P/P_0$, highlighting in dark grey as opposed to black, the points selected for the BET calculation of MET-1. A liquid $N_2$ bath was used for adsorption measurements at 77K. Inset shows the fitting plot for BET calculation.
Figure 36:
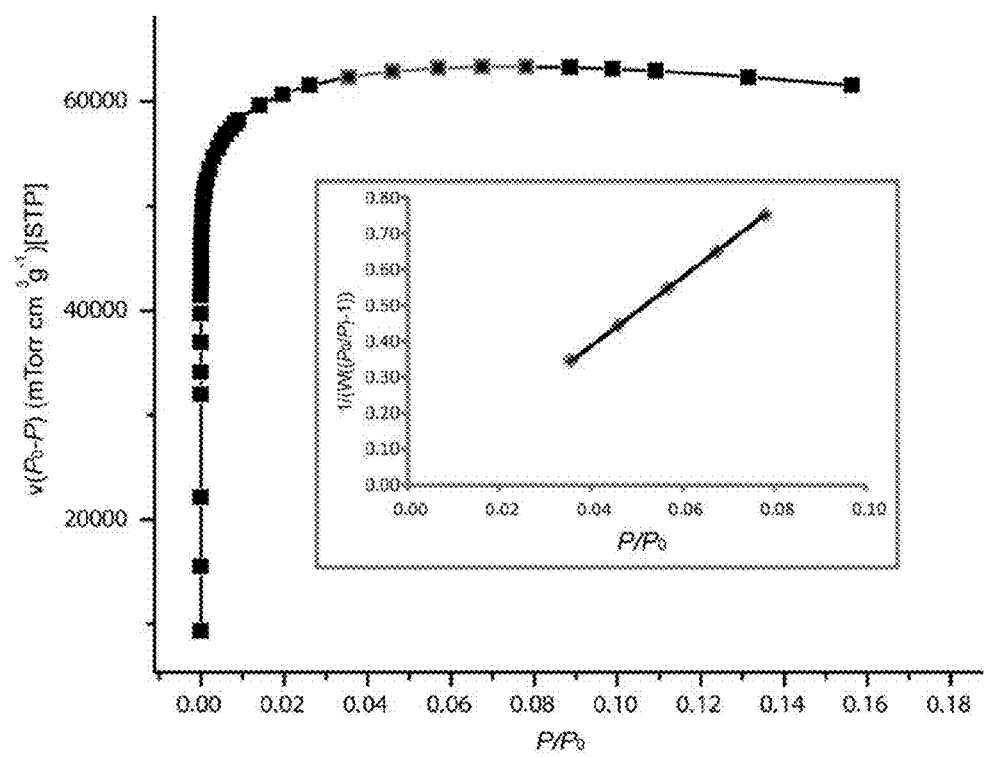
FIG. 36 provides a $N_2$ isotherm curve for MET-5. The curve is a plot of $v(P_0-P)$ against $P/P_0$, highlighting in dark grey as opposed to black, the points selected for the BET calculation of MET-1. A liquid $N_2$ bath was used for adsorption measurements at 77K. Inset shows the fitting plot for BET calculation.
Figure 37:
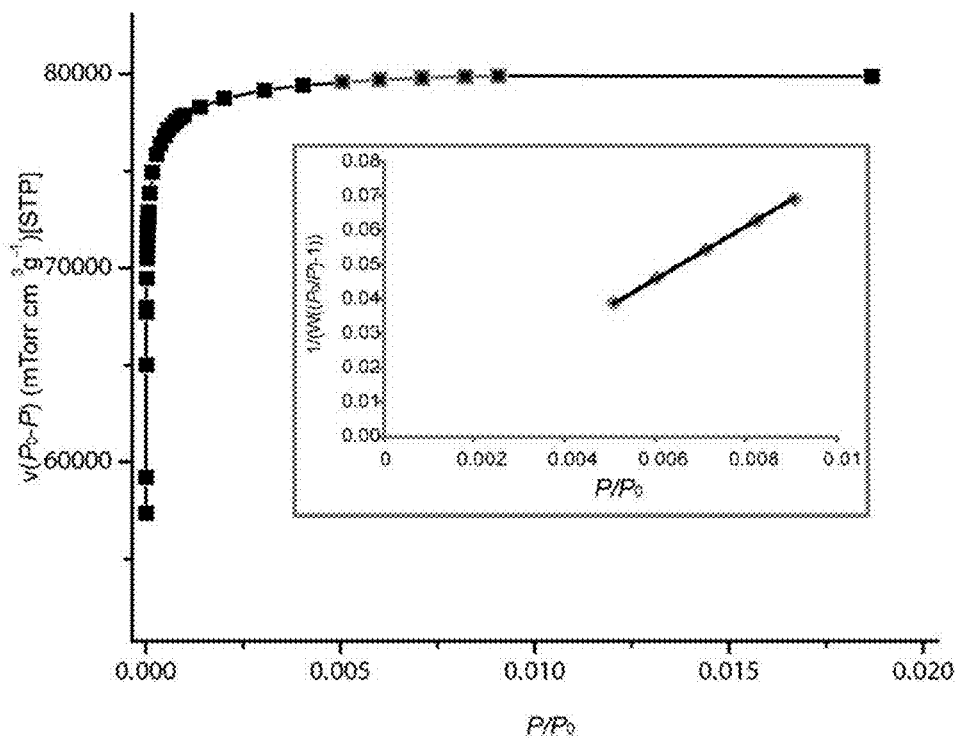
FIG. 37 provides a $N_2$ isotherm curve for MET-6. The curve is a plot of $v(P_0-P)$ against $P/P_0$, highlighting in dark grey as opposed to black, the points selected for the BET calculation of MET-1. A liquid $N_2$ bath was used for adsorption measurements at 77K. Inset shows the fitting plot for BET calculation.

To confirm the differences in the pore sizes, Ar adsorption isotherm measurements were performed at 87 K (FIG. 24). Ar adsorption usually occurs at greater $P/P_0$ value compared to $N_2$, thus allowing observation of the differences in the low pressure range, which are associated with the differences in the pore sizes. The pressure range of micropore filling increases with an increase in pore diameter. At low pressures the differences in the uptake are associated to the pore size. For larger pore sizes, more pronounced steps appear at higher pressure. In the inset of FIG. 24 and FIG. 31, the normalized Ar isotherms are plotted in a logarithmic scale to better appreciate these differences. The trend is in agreement with the one derived from the crystal data, showing the MET-1, and MET-3 as those MET frameworks with the smallest pore sizes, MET-7 and MET-2 those with the largest pore, and intermediate values for the rest of MET frameworks (Table 4).

FIGS. 24 to 30 show the individual Ar adsorption isotherms of MET-1 to MET-6 of the disclosure, respectively. METs-2 and -3 show typical type I isotherm curves. In the case of METs-1, -4, -5, and -6 the isotherms show the expected micropore filling in the low pressure range, and the increase in the uptake at high pressure and the observed hysteresis are attributed to capillary condensation, indicating the presence of mesoporous intergrain voids.

$N_2$ Adsorption Isotherms:

Low pressure gas adsorption isotherms were measured volumetrically on an Autosorb-1 analyzer (Quantachrome Instruments). A liquid $N_2$ bath was used for adsorption measurements at 77 K. The gas used was UHP grade (99.999%). For the calculation of surface areas, the Langmuir and BET methods were applied using the adsorption branches of the $N_2$ isotherms assuming a $N_2$ cross-sectional area of 16.2 $Å^2$/molecule. BET areas were calculated in pressure range with values of $v(P_0-P)$ increasing with $P/P_0$, according to the method reported by Walton and Snurr. The pore volume was determined using the Dubinin-Radushkevich (DR) method with the assumption that the adsorbate is in the liquid state and the adsorption involves a pore-filling process.

The permanent porosity of the MET frameworks was first demonstrated by the $N_2$ sorption isotherms, collected at 77 K. All the MET frameworks show typical microporous behavior by adsorbing significant amounts of $N_2$ in the micropore region (FIG. 31). The surface area of the MET frameworks was calculated according to the Brunauer-Emmet-Teller (BET) method, with values varying from 370 to 890 $m^2$/g, (450 to 1010 $m^2 g^{-1}$ for Langmuir surface areas), where we chose the pressure range with values of $v(P_0-P)$ increasing with $P/P_0$ (v is adsorbed amount of $N_2$). These values are in good agreement with those geometric surface areas estimated from their crystal structures with the only exception of MET-5, which is probably due to an incomplete activation of the framework. The plot of $v(P_0-P)$ against $P/P_0$, for the $N_2$ isotherm data for MET-1 to MET-6 is presented in FIGS. 32 to 37, respectively. The $N_2$ isotherms of MET-4 and -5 did not show a clear plateau region, which is attributed to the intergrain porosity because of the smaller crystal size of both materials (as indicated by their broad PXRD diffraction peaks). FIGS. 32 to 37 show the selected pressure range area for the BET calculation and the fitting plots, all carried out with the $N_2$ sorption data for MET-1 to MET-6, respectively. Geometrical calculation of the accessible surface area of the crystal structures were performed with Materials Studio void tool, employing a grid interval of 0.25 Å, with a probe molecule of initial and maximum radius of 1.4 Å and 2.0 Å, respectively. The calculated surface area values are shown in Table 4. MET-2 was found to have the highest surface area among the isoreticular series (see Table 4), as expected for its higher unit cell volume and pore size.

TABLE 4

| MET | Refined unit cell parameter (Å) | Cell volume ($Å^3$) | Void (%) | Pore Volume ($cm^3g^{-1}$) | Calculated Cavities diameter (Å) | Calculated accessible surface area ($m^2g^{-1}$) | BET area ($m^2g^{-1}$) | Langmuir area ($m^2g^{-1}$) |
|---|---|---|---|---|---|---|---|---|
| MET-1 | 16.551 | 4533.9 | 22.4 | 0.18 | 4.50 | 572 | 430 | 510 |
| MET-2 | 18.152 | 5971.7 | 40.5 | 0.35 | 6.12 | 1143 | 890 | 1010 |
| MET-3 | 16.635 | 4617.9 | 22.4 | 0.18 | 4.54 | 557 | 450 | 500 |
| MET-4 | 17.342 | 5215.8 | 35.3 | 0.26 | 5.16 | 835 | 600 | 760 |
| MET-5 | 17.415 | 5322.2 | 24.0 | 0.15 | 4.86 | 827 | 370 | 450 |
| MET-6 | 17.734 | 5577.9 | 25.3 | 0.17 | 5.06 | 429 | 460 | 480 |
| MET-7 | 18.604 | 6439.2 | 50.0 | — | 6.80 | — | 650 | 680 |

Figure 26:
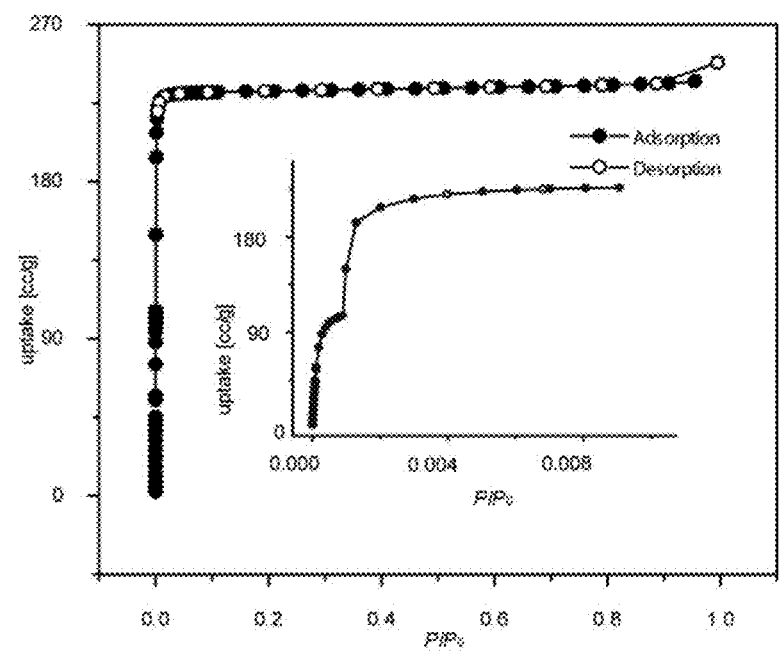
FIG. 26 provides a plot of the Ar isotherm for MET-2. A liquid Ar bath was used for adsorption measurements at 87 K. The isotherm curve for MET-2 is a typical type I isotherm curve. Inset shows the zoom in the low pressure region FIG. 27 provides a plot of the Ar isotherm for MET-3. A liquid Ar bath was used for adsorption measurements at 87 K. The isotherm curve for MET-3 is a typical type I isotherm curve.
Figure 27:
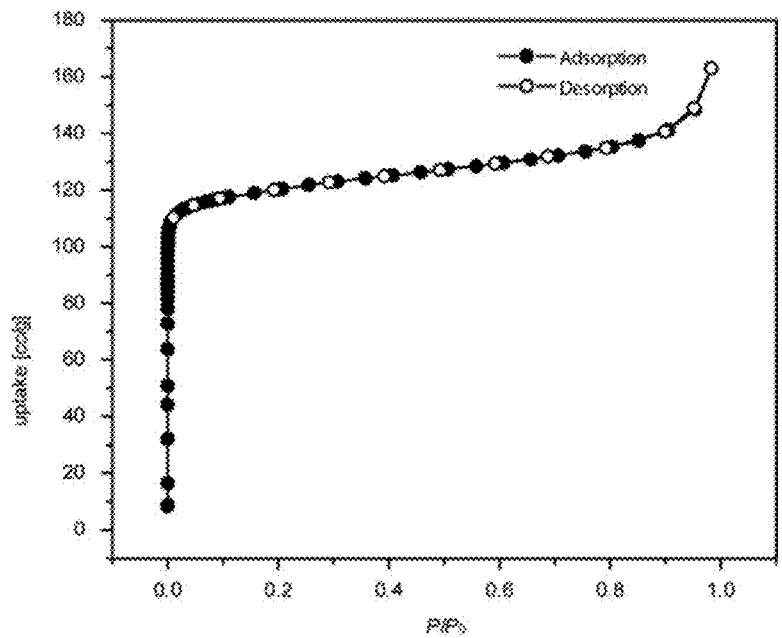
Figure 28:
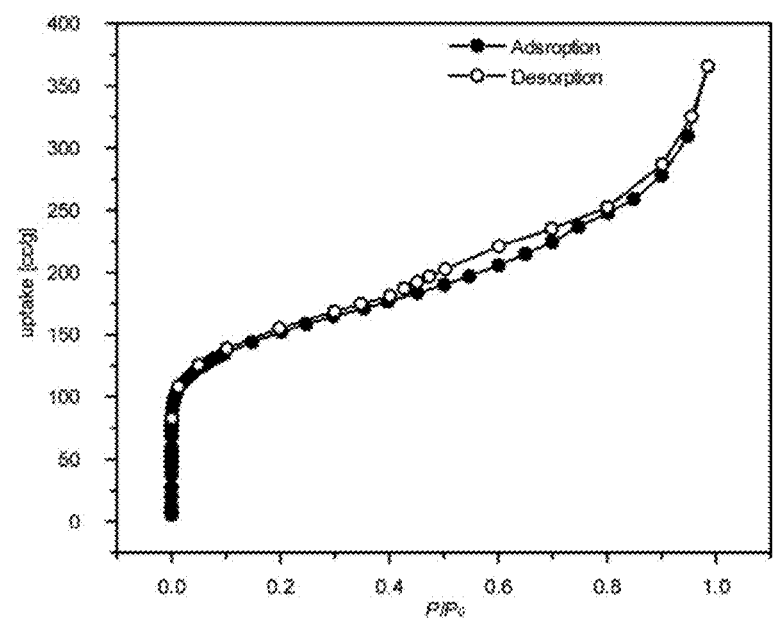
FIG. 28 provides a plot of the Ar isotherm for MET-4. A liquid Ar bath was used for adsorption measurements at 87 K. The MET-4 isotherm demonstrates the expected micropore filling in the low pressure range, and the increase in the uptake at high pressure. The observed hysteresis is attributed to capillary condensation, indicating the presence of mesoporous intergrain voids.
Figure 29:
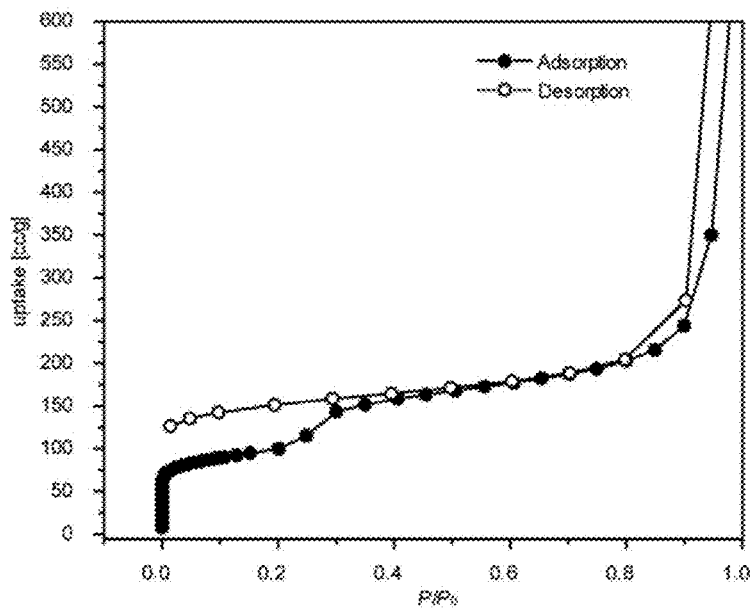
FIG. 29 provides a plot of the Ar isotherm for MET-5. A liquid Ar bath was used for adsorption measurements at 87 K. The MET-5 isotherm demonstrates the expected micropore filling in the low pressure range, and the increase in the uptake at high pressure. The observed hysteresis is attributed to capillary condensation, indicating the presence of mesoporous intergrain voids.
Figure 30:
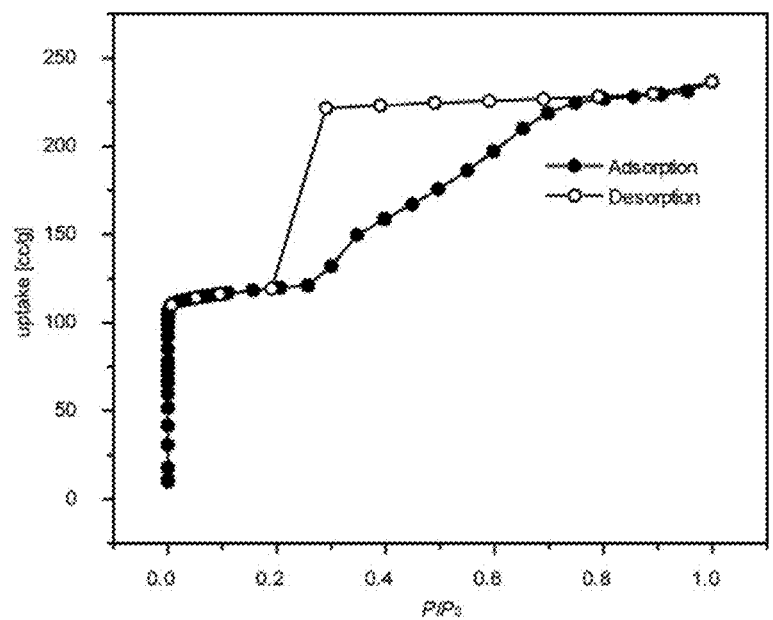
FIG. 30 provides a plot of the Ar isotherm for MET-6. A liquid Ar bath was used for adsorption measurements at 87 K. The MET-6 isotherm demonstrates the expected micropore filling in the low pressure range, and the increase in the uptake at high pressure. The observed hysteresis is attributed to capillary condensation, indicating the presence of mesoporous intergrain voids.

MET-2 N₂ Step Pattern Characterization:

The step observed in the low pressure region of the MET-2 $N_2$ isotherm (also observed at lower relative pressure in the Ar isotherm, see FIG. 26) can be attributed to a phase transition of the adsorbates within the pores so that the pores can accommodate a higher number of gas molecules, resulting in the highest surface area among the series.

To evaluate a possible structural change as the origin of the step observed in the low pressure region of MET-2, a glass capillary was filled with MET-2 sample, evacuated to 100 mTorr and then sealed. The PXRD pattern was then collected with a Data were collected on a Bruker APEXII three circle diffractometer equipped with a CCD area detector and operated at 1200 W power (40 kV, 30 mA) to generate Cu Kα radiation (λ=1.5418 Å). Another capillary filled with MET-2 sample was evacuated up to the same pressure, refilled with $N_2$ up to atmospheric pressure and then sealed. A third capillary was filled with sample and sealed, for control experiment.

Figure 38:
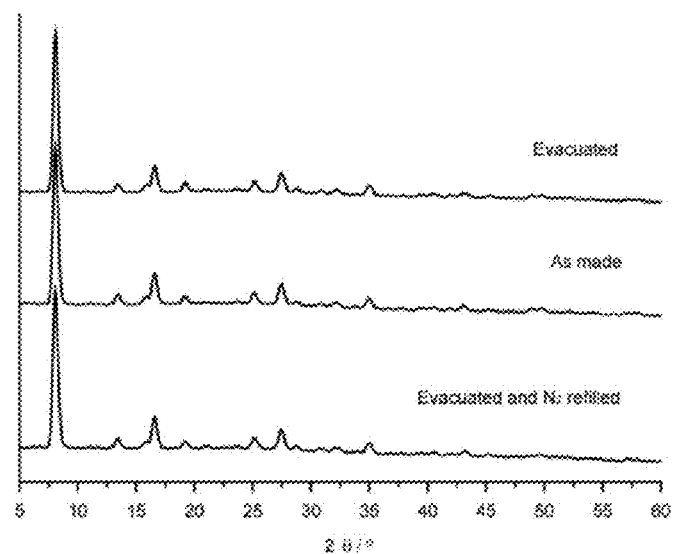
FIG. 38 provides a comparison of the PXRD patterns of the MET-2 samples measured after evacuation at 100 mTorr (top), as made (middle), and evacuated at 100 mTorr and refilled with $N_2$ up to atmospheric pressure (bottom).

Therefore, the possibility that a structural change causes the observed step in the MET-2 $N_2$ isotherm can be ruled out by the lack of changes in the PXRD patterns of a sample evacuated to a pressure below the step position and another sample evacuated and then filled with $N_2$ up to atmospheric pressure (FIG. 38).

Electrical Conductivity Measurements:

For the determination of the specific resistivity of the materials, the four-point probe measure is used. The materials have been pressed as a bulk. 100 nm gold electrodes were thermally deposited by shadow mask on the bulk. Finally, the four probe measurements were carried out directly after deposition using a standard probe station under ambient conditions.

Electrical conductivity is a property that remains relatively unexplored in the field of porous MOFs, despite the great interest that would be sparked by a multifunctional material with high surface area and electrical conductivity. Tests on the electrical conductivity of MET-3 were performed. The small size and morphology of the crystals make them unsuitable for single crystal measurements. Therefore, electrical measurements in a pressed pellet of the polycrystalline material were performed. A conventional four-probe measurement was carried out with a pellet (1 cm in diameter and 0.5 mm in thickness) made from freshly prepared material. The results indicate that MET-3 is an intrinsically conducting material (FIG. 39, panel a), with a conductivity value of $0.77 \times 10^{-4}$ S cm$^{-1}$.

Figure 39:
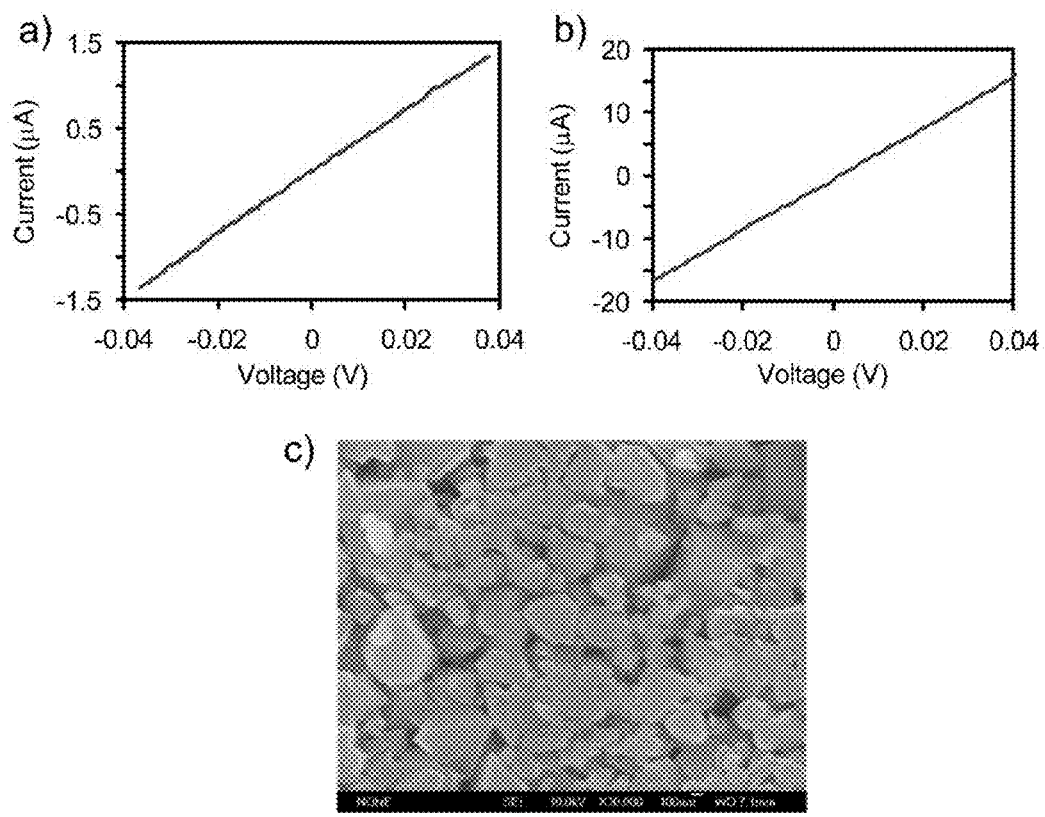
FIG. 39 provides I-V curves as proved by the I-V curves recorded with the as synthesized MET-3 framework (a), and doped with $I_2$ (b). The curves indicate that MET-3 is an intrinsically conducting material. Panel (c) presents a SEM image (30000×) of the MET-3 pellets employed for the conductivity measurements.

The conducting characteristics of MET-3 can further be improved (FIG. 39, panel b) through a doping process, in which the sample is exposed to $I_2$ vapor. After 40 minutes of exposure, the conductivity value increases to $1.0 \times 10^{-35}$ cm$^{-1}$. PXRD patterns show that the material remains unaltered after the pellet formation and exposure to $I_2$. A possible explanation for the large increase in conductivity on exposure to iodine is that Fe(II) is being oxidized to Fe(III), resulting in mixed valence conductivity such is found in oxides like $Fe_3O_4$. The electrical conducting characteristic of polycrystalline pellet materials may be largely limited by the existence of a large number of grain boundaries, as observed in the scanning electron microscopy (SEM) images of the pellet (FIG. 39, panel c). With further development in the crystal growth process to allow formation of larger crystals, more accurate characterization of the intrinsic electrical conductivity of these materials can be achieved. Additionally, the sample is rather stable and the conductivity does not degrade with time, as indicated by the measurement of an undoped pellet left in air for 8 weeks.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A metal-triazolate (MET) framework comprising a plurality of cores of structural Formula I:

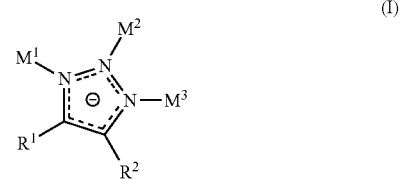

wherein,
$M^1$, $M^2$ and $M^3$ are independently selected metal, metals ions or are absent, and wherein at least two of $M^1$, $M^2$ and $M^3$ are metal or metal ions;

$R^1$-$R^2$ are independently selected from the group consisting of H, optionally substituted FG, optionally substituted ($C_1$-$C_6$)alkyl, optionally substituted ($C_1$-$C_6$)alkenyl, optionally substituted ($C_2$-$C_6$)alkynyl, optionally substituted hetero-($C_1$-$C_6$)alkyl, optionally substituted hetero-($C_1$-$C_6$)alkenyl, optionally substituted hetero-($C_2$-$C_6$)alkynyl, optionally substituted cycloalkyl, optionally substituted cycloalkenyl, optionally substituted aryl, optionally substituted heterocycle, optionally substituted mixed ring system, —C($R^7$)$_3$, —CH($R^7$)$_2$, —CH$_2R^7$, —C($R^8$)$_3$, —CH($R^8$)$_2$, —CH$_2R^8$, —OC($R^7$)$_3$, —OCH($R^7$)$_2$, —OCH$_2R^7$, —OC($R^8$)$_3$, —OCH($R^8$)$_2$, —OCH$_2R^8$,

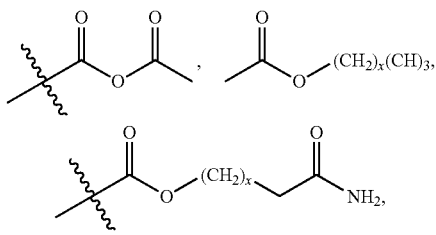

and wherein $R^1$ and $R^2$ can be linked together as ring atoms of a substituted or unsubstituted ring selected from the group consisting of cycloalkyl, cycloalkenyl, heterocycle, aryl and mixed ring system;

$R^7$ is selected from the group consisting of halo, hydroxyl, amine, thiol, cyano, carboxyl, optionally substituted ($C_1$-$C_6$)alkyl, optionally substituted ($C_1$-$C_6$)alkenyl, optionally substituted ($C_2$-$C_6$)alkynyl, optionally substituted hetero-($C_1$-$C_6$)alkyl, optionally substituted hetero-($C_1$-$C_6$)alkenyl, optionally substituted hetero-($C_2$-$C_6$)alkynyl, hemiacetal, hemiketal, acetal, ketal, and orthoester;

$R^8$ is one or more substituted or unsubstituted rings selected from the group consisting of cycloalkyl, cycloalkenyl, aryl, heterocycle, and mixed ring system; and X is a number from 0 to 3, wherein the metal or metal ions are selected from $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, and $Lu^{3+}$.

2. The MET framework of claim 1, comprising one or more cores of structural Formula I:

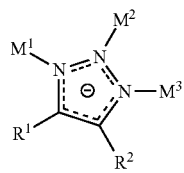

(I)

wherein,
$M^1$, $M^2$ and $M^3$ are independently absent or metals ions selected from the group consisting of $Mg^{2+}$, $Mn^{2+}$, $Fe^{2+}$, $Co^{2+}$, and $Zn^{2+}$, and wherein at least two of $M^1$, $M^2$ and $M^3$ are metal ions; and
$R^1$-$R^2$ are H.

3. The MET framework of claim 2, having the characteristics specified for any one of the frameworks presented in Table 4.

4. The MET framework of claim 1, comprising a dia framework topology.

5. The MET framework of claim 1, wherein at least two of $M^1$, $M^2$, and $M^3$ are independently selected divalent metal ions.

6. The MET framework of claim 5, wherein at least two of $M^1$, $M^2$, and $M^3$ are independently selected divalent metal ions selected from the group consisting of $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $B^{2+}$, $Al^{2+}$, $Ga^{2+}$, $Si^{2+}$, $Sn^{2+}$, $Pb^{2+}$, $Hg^{2+}$, $As^{2+}$, $Te^{2+}$, $La^{2+}$, $Ce^{2+}$, $Pr^{2+}$, $Sm^{2+}$, $Gd^{2+}$, $Nd^{2+}$, $Db^{2+}$, $Tb^{2+}$, $Tm^{2+}$ and $Yb^{2+}$.

7. The MET framework of claim 1, wherein the cores are produced by reacting metal or metal ions with one or more linking moieties of structural Formula II:

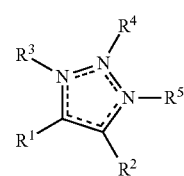

(II)

wherein:
$R^1$-$R^2$ are independently selected from the group consisting of H, optionally substituted FG, optionally substituted ($C_1$-$C_6$)alkyl, optionally substituted ($C_1$-$C_6$)alkenyl, optionally substituted ($C_2$-$C_6$)alkynyl, optionally substituted hetero-($C_1$-$C_6$)alkyl, optionally substituted hetero-($C_1$-$C_6$)alkenyl, optionally substituted hetero-($C_2$-$C_6$)alkynyl, optionally substituted cycloalkyl, optionally substituted cycloalkenyl, optionally substituted aryl, optionally substituted heterocycle, optionally substituted mixed ring system, —$C(R^7)_3$, —$CH(R^7)_2$, —$CH_2R^7$, —$C(R^8)_3$, —$CH(R^8)_2$, —$CH_2R^8$, —$OC(R^7)_3$, —$OCH(R^7)_2$, —$OCH_2R^7$, —$OC(R^8)_3$, —$OCH(R^8)_2$, —$OCH_2R^8$,

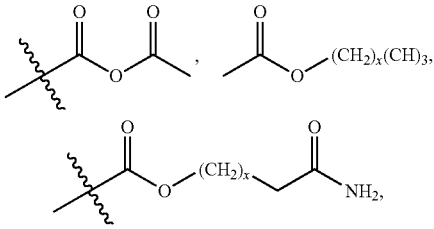

and wherein $R^1$ and $R^2$ can be linked together as ring atoms of a substituted or unsubstituted ring selected from the group consisting of cycloalkyl, cycloalkenyl, heterocycle, aryl and mixed ring system;
$R^3$-$R^5$ are independently H, D or are absent when bound to a N atom that is doubly bonded to another atom;
$R^7$ is selected from the group consisting of halo, hydroxyl, amine, thiol, cyano, carboxyl, optionally substituted ($C_1$-$C_6$)alkyl, optionally substituted ($C_1$-$C_6$)alkenyl, optionally substituted ($C_2$-$C_6$)alkynyl, optionally substituted hetero-($C_1$-$C_6$)alkyl, optionally substituted hetero-($C_1$-$C_6$)alkenyl, optionally substituted hetero-($C_2$-$C_6$)alkynyl, hemiacetal, hemiketal, acetal, ketal, and orthoester;
$R^8$ is one or more substituted or unsubstituted rings selected from the group consisting of cycloalkyl, cycloalkenyl, aryl, heterocycle, and mixed ring system; and
X is a number from 0 to 3.

8. The MET framework of claim 7, wherein the cores are produced by reacting metal or metal ions with one or more linking moieties having structural Formula II, wherein:
$R^1$-$R^2$ are independently selected from the group consisting of H, halo, amine, cyano, $CO_2H$, $NO_2$, $SO_3H$, $PO_3H$, optionally substituted ($C_1$-$C_4$)alkyl, optionally substituted ($C_1$-$C_4$)alkenyl, optionally substituted ($C_2$-$C_4$) alkynyl, optionally substituted hetero-($C_1$-$C_4$)alkyl, optionally substituted hetero-($C_1$-$C_4$)alkenyl, and optionally substituted hetero-($C_2$-$C_4$)alkynyl; and
$R^3$-$R^5$ are independently H, D or are absent when bound to a N atom that is doubly bonded to another atom.

9. The MET framework of claim 7, wherein the cores are produced by reacting metal or metal ions with one or more linking moieties selected from the group consisting of 2H-[1, 2,3]triazole, 1H-[1,2,3]triazole, 4-chloro-2H-[1,2,3]triazole, 4-chloro-1H-[1,2,3]triazole, 4,5-dichloro-2H-[1,2,3]triazole, 4,5-dichloro-1H-[1,2,3]triazole, 4-bromo-2H-[1,2,3] triazole, 4-bromo-1H-[1,2,3]triazole, 4,5-dibromo-2H-[1,2, 3]triazole, 4,5-dibromo-1H-[1,2,3]triazole, 4-fluoro-2H-[1, 2,3]triazole, 4-fluoro-1H-[1,2,3]triazole, 4,5-difluoro-2H-[1, 2,3]triazole, 4,5-difluoro-1H-[1,2,3]triazole, 4-iodo-2H-[1, 2,3]triazole, 4-iodo-1H-[1,2,3]triazole, 4,5-diiodo-2H-[1,2, 3]triazole, 4,5-diiodo-1H-[1,2,3]triazole, 5-trifluoromethyl-2H-[1,2,3]triazole, 5-trifluoromethyl-1H-[1,2,3]triazole, 4,5-bis-trifluoromethyl-2H-[1,2,3]triazole, 4,5-bis-trifluoromethyl-1H-[1,2,3]triazole, 2H-[1,2,3]triazole-4-ol, 1H-[1, 2,3]triazole-4-ol, 2H-[1,2,3]triazole-4,5-diol, 1H-[1,2,3]triazole-4,5-diol, 2H-[1,2,3]triazole-4-carbonitrile, 1H-[1,2,3] triazole-4-carbonitrile, 2H-[1,2,3]triazole-4,5-dicarbonitrile, 1H-[1,2,3]triazole-4,5-dicarbonitrile, 2H-[1,2,3]triazole-4-ylamine, 1H-[1,2,3]triazole-4-ylamine, 2H-[1,2,3]triazole-4, 5-diamine, 1H-[1,2,3]triazole-4,5-diamine, 4-methyl-2H-[1, 2,3]triazole, 4-methyl-1H-[1,2,3]triazole, 4-ethyl-2H-[1,2,3] triazole, 4-ethyl-1H-[1,2,3]triazole, 4-propyl-2H-[1,2,3] triazole, 4-propyl-1H-[1,2,3]triazole, 4-butyl-2H-[1,2,3] triazole, 4-butyl-1H-[1,2,3]triazole, 4-isopropyl-2H-[1,2,3] triazole, 4-isopropyl-1H-[1,2,3]triazole, 4,5-diisopropyl-2H-[1,2,3]triazole, 4,5-diisopropyl-1H-[1,2,3]triazole, 4-tert-butyl-2H-[1,2,3]triazole, 4-tert-butyl-1H-[1,2,3]triazole, 4,5-di-tert-butyl-2H-[1,2,3]triazole, 4,5-di-tert-butyl-1H-[1, 2,3]triazole, 2H-[1,2,3]triazole-4-carboxylic acid, 1H-[1,2, 3]triazole-4-carboxylic acid, 2H-[1,2,3]triazole-4,5-dicarboxylic acid, 1H-[1,2,3]triazole-4,5-dicarboxylic acid, 2H-[1,2,3]triazole-4-carbaldehyde, 1H-[1,2,3]triazole-4-carbaldehyde, 2H-[1,2,3]triazole-4,5-dicarbaldehyde, 1H-[1, 2,3]triazole-4,5-dicarbaldehyde, 1-(2H-[1,2,3]triazole-4-yl)-ethanone, 1-(1H-[1,2,3]triazole-4-yl)-ethanone, 1-(5-acetyl-2H-[1,2,3]triazole-4-yl)-ethanone, 1-(5-acetyl-1H-[1,2,3] triazole-4yl)-ethanone, 2H-[1,2,3]triazole-4-thiol, 1H-[1,2, 3]triazole-4-thiol, 2H-[1,2,3]triazole-4,5-dithiol, 1H-[1,2,3] triazole-4,5-dithiol, 5-mercaptomethyl-2H-[1,2,3]triazole-4-thiol, 5-mercaptomethyl-1H-[1,2,3]triazole-4-thiol, (5-mercaptomethyl-2H-[1,2,3]triazole-4-yl)-methanethiol, (5-mercaptomethyl-1H-[1,2,3]triazole-4-yl)-methanethiol, 4-nitro-2H-[1,2,3]triazole, 4-nitro-1H-[1,2,3]triazole, 4,5-dinitro-2H-[1,2,3]triazole, 4,5-dinitro-1H-[1,2,3]triazole, 4-vinyl-2H-[1,2,3]triazole, 4-vinyl-1H-[1,2,3]triazole, 4,5-divinyl-2H-[1,2,3]triazole, 4,5-divinyl-1H-[1,2,3]triazole, 2H-[1,2,3]triazolo[4,5-c]pyridine, 3H-[1,2,3]triazolo[4,5-c] pyridine, 2H-[1,2,3]triazolo[4,5-b]pyridine, 3H-[1,2,3]triazolo[4,5-b]pyridine, 2H-[1,2,3]triazolo[4,5-d]pyrimidine, 3H-[1,2,3]triazolo[4,5-d]pyrimidine, 2H-[1,2,3]triazolo[4,5-b]pyrazine, 3H-[1,2,3]triazolo[4,5-b]pyrazine, dimethyl-(2H-[1,2,3]triazol-4-yl)-amine, dimethyl-(1H-[1,2,3]triazol-4-yl)-amine, N,N,N',N'-tetramethyl-2H-[1,2,3]triazol-4,5-diamine, and N,N,N',N'-tetramethyl-1H-[1,2,3]triazol-4,5-diamine.

10. The MET framework of claim 1, wherein the cores comprise one or more linking moieties of structural Formula II:

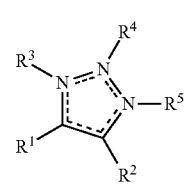

(II)

wherein:
$R^1$-$R^2$ are independently selected so as to either interact with one or more particular gases, to modulate the pore size of the MET framework, or a combination thereof; and
$R^3$-$R^5$ are independently H, D or are absent when bound to a N atom that is doubly bonded to another atom.

11. The MET framework of claim 1, wherein the MET framework is reacted with one or more post framework reactants.

12. The MET framework of claim 11, wherein one or more post framework reactants adds at least one effect to the MET framework selected from the group consisting of:
modulates the gas storage ability of the MET framework;
modulates the sorption properties of the MET framework;
modulates the pore size of the MET framework;
modulates the catalytic activity of the MET framework;
modulates the conductivity of the MET framework; and
modulates the sensitivity of the MET framework to the presence of an analyte of interest.

13. The MET framework of claim 1, further comprising a one or more guest species.

14. The MET framework of claim 1, further comprising one or more absorbed or adsorbed chemical species.

15. The MET framework of claim 14, wherein the adsorbed or absorbed chemical species is selected from the group consisting of argon, ammonia, carbon dioxide, carbon monoxide, hydrogen, amines, oxygen, ozone, nitrogen, nitrous oxide, organic dyes, polycyclic organic molecules, hydrogen sulfide, carbonyl sulfide, carbon disulfide, mercaptans, hydrocarbons, formaldehyde, diisocyanates, trichloroethylene, fluorocarbons, and combinations thereof.

16. A method to separate or store one or more gases from a mixed gas mixture comprising contacting the gas mixture with a MET framework comprising one or more cores of structural Formula I:

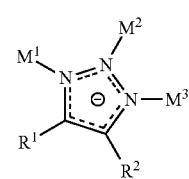

(I)

wherein,
$M^1$, $M^2$ and $M^3$ are independently selected metal, metals ions or absent, and wherein at least two of $M^1$, $M^2$ and $M^3$ are metal or metal ions;
$R^1$-$R^2$ are independently selected from the group consisting of H, optionally substituted FG, optionally substituted ($C_1$-$C_6$)alkyl, optionally substituted ($C_1$-$C_6$)alkenyl, optionally substituted ($C_2$-$C_6$)alkynyl, optionally substituted hetero-($C_1$-$C_6$)alkyl, optionally substituted hetero-($C_1$-$C_6$)alkenyl, optionally substituted hetero- ($C_2$-$C_6$)alkynyl, optionally substituted cycloalkyl, optionally substituted cycloalkenyl, optionally substituted aryl, optionally substituted heterocycle, optionally substituted mixed ring system, —C($R^7$)$_3$, —CH($R^7$)$_2$, —CH$_2$$R^7$, —C($R^8$)$_3$, —CH($R^8$)$_2$, —CH$_2$$R^8$, —OC($R^7$)$_3$, —OCH($R^7$)$_2$, —OCH$_2$$R^7$, —OC($R^8$)$_3$, —OCH($R^8$)$_2$, —OCH$_2$$R^8$;

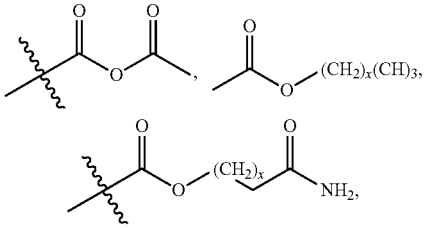

and wherein $R^1$ and $R^2$ can be linked together as ring atoms of a substituted or unsubstituted ring selected from the group consisting of cycloalkyl, cycloalkenyl, heterocycle, aryl and mixed ring system;

$R^7$ is selected from the group consisting of halo, hydroxyl, amine, thiol, cyano, carboxyl, optionally substituted ($C_1$-$C_6$)alkyl, optionally substituted ($C_1$-$C_6$)alkenyl, optionally substituted ($C_2$-$C_6$)alkynyl, optionally substituted hetero-($C_1$-$C_6$)alkyl, optionally substituted hetero-($C_1$-$C_6$)alkenyl, optionally substituted hetero-($C_2$-$C_6$)alkynyl, hemiacetal, hemiketal, acetal, ketal, and orthoester;

$R^8$ is one or more substituted or unsubstituted rings selected from the group consisting of cycloalkyl, cycloalkenyl, aryl, heterocycle, and mixed ring system; and X is a number from 0 to 3.

17. The method of claim 16, wherein the one or more gases separated and stored are selected from ammonia, argon, hydrogen sulfide, carbon dioxide, hydrogen sulfide, carbonyl sulfide, carbon disulfide, mercaptans, carbon monoxide, and hydrogen.

18. The method of claim 16, wherein the mixed gas mixture comprises a fuel gas stream.

19. The method of claim 18, wherein the fuel gas stream is a natural gas stream and wherein one or more acid gases are separated from the natural gas stream.

20. The method of claim 16, wherein the mixed gas mixture comprises exhaust from a combustion engine.

21. A gas storage, gas detector or gas separation device comprising the MET framework of claim 1.

22. The device of claim 21, wherein the gas storage, gas detector or gas separation device is selected from the group consisting of purifiers, filters, scrubbers, pressure swing adsorption devices, molecular sieves, hollow fiber membranes, ceramic membranes, cryogenic air separation devices, carbon monoxide detector, car emissions detector and hybrid gas separation devices.

23. An electrical conductor comprising the MET framework of claim 1.

24. A catalyst comprising the MET framework of claim 1.

25. A chemical sensor comprising the MET framework of claim 1.

26. The method of claim 16, wherein the metal or metal ions are selected from $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, and $Lu^{3+}$.

* * * * *